US012569538B2

(12) United States Patent
Robbins et al.

(10) Patent No.: US 12,569,538 B2
(45) **Date of Patent: *Mar. 10, 2026**

(54) DPEP-1 BINDING COMPOSITIONS AND METHODS OF USE

(71) Applicant: Arch Biopartners, Inc., Toronto (CA)

(72) Inventors: Stephen Mark Robbins, Calgary (CA); Donna Lorraine Senger, Calgary (CA); Jennifer Joy Rahn, Calgary (CA); Arthur Wing Sze Lau, Calgary (CA); Daniel Abraham Muruve, Calgary (CA); Saurav Roy Choudhury, Calgary (CA); Liane Babes, Calgary (CA); Paul Kubes, Calgary (CA)

(73) Assignee: Arch Biopartners, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,345

(22) Filed: Jun. 5, 2023

(65) Prior Publication Data

US 2024/0108686 A1 Apr. 4, 2024

Related U.S. Application Data

(63) Continuation of application No. 16/504,909, filed on Jul. 8, 2019, now Pat. No. 11,666,631, which is a continuation of application No. 15/234,521, filed on Aug. 11, 2016, now Pat. No. 10,493,127.

(60) Provisional application No. 62/264,032, filed on Dec. 7, 2015, provisional application No. 62/203,704, filed on Aug. 11, 2015.

(51) Int. Cl.

| | |
|---|---|
| ***A61K 38/17*** | (2006.01) |
| ***A61K 9/00*** | (2006.01) |
| ***A61K 31/662*** | (2006.01) |
| ***A61K 31/664*** | (2006.01) |
| ***A61K 38/08*** | (2019.01) |
| ***A61K 38/10*** | (2006.01) |
| ***A61K 38/55*** | (2006.01) |
| ***A61P 13/12*** | (2006.01) |
| ***A61P 29/00*** | (2006.01) |
| ***A61P 35/04*** | (2006.01) |
| ***A61P 37/06*** | (2006.01) |
| ***A61P 43/00*** | (2006.01) |
| ***C07C 323/58*** | (2006.01) |
| ***C07F 9/30*** | (2006.01) |
| ***C07K 16/40*** | (2006.01) |
| ***C12N 9/48*** | (2006.01) |

(52) U.S. Cl.

CPC ........ *A61K 38/1709* (2013.01); *A61K 9/0019* (2013.01); *A61K 31/662* (2013.01); *A61K 31/664* (2013.01); *A61K 38/08* (2013.01); *A61K 38/10* (2013.01); *A61K 38/55* (2013.01); *A61P 13/12* (2018.01); *A61P 29/00* (2018.01); *A61P 35/04* (2018.01); *A61P 37/06* (2018.01); *A61P 43/00* (2018.01); *C07C 323/58* (2013.01); *C07F 9/302* (2013.01); *C07K 16/40* (2013.01); *C12N 9/485* (2013.01); *C12Y 304/13019* (2013.01); *C07K 2317/76* (2013.01)

(58) Field of Classification Search

CPC .............. A61K 38/1709; A61K 31/662; A61K 9/0019; A61K 31/664; A61K 38/08; A61K 38/10; A61K 38/55; A61P 43/00; A61P 37/06; A61P 13/12; A61P 29/00; A61P 35/04; C07C 323/58; C07F 9/302; C07K 16/40; C07K 2317/76; C12N 9/485; C12Y 304/13019

USPC ...................................................... 424/158.1

See application file for complete search history.

(56) References Cited

U.S. PATENT DOCUMENTS

| | | | | |
|---|---|---|---|---|
| 4,244,946 | A | 1/1981 | Rivier | |
| 4,305,872 | A | 12/1981 | Johnston | |
| 4,316,891 | A | 2/1982 | Guillemin | |
| 5,223,409 | A | 6/1993 | Ladner | |
| 5,403,484 | A | 4/1995 | Ladner | |
| 5,571,698 | A | 11/1996 | Ladner | |
| 5,629,179 | A | 5/1997 | Mierendorf | |
| 5,766,905 | A | 6/1998 | Studier | |
| 6,174,687 | B1 | 1/2001 | Rajotte et al. | |
| 9,464,114 | B2 * | 10/2016 | Robbins | A61K 38/10 |
| 10,493,127 | B2 * | 12/2019 | Robbins | A61K 31/662 |
| 11,083,773 | B2 * | 8/2021 | Robbins | A61P 31/12 |
| 11,666,631 | B2 * | 6/2023 | Robbins | A61K 38/1709 514/21.4 |
| 2008/0051428 | A1 | 2/2008 | Davis | |
| 2010/0324469 | A1 | 12/2010 | Mori et al. | |
| 2011/0165264 | A1 | 7/2011 | Tejedor Jorge | |
| 2012/0023611 | A1 | 1/2012 | Cao | |

(Continued)

FOREIGN PATENT DOCUMENTS

| | | |
|---|---|---|
| EP | 2143429 | 1/2010 |
| WO | WO 99/46284 | 9/1999 |

(Continued)

OTHER PUBLICATIONS

Toyoguchi et al., Antimicrobial Agents and Chemotherapy, 1997, 1985-1990. (Year: 1997).

(Continued)

*Primary Examiner* — Kristin A Vajda

(74) *Attorney, Agent, or Firm* — King & Spalding

(57) ABSTRACT

Pharmaceutical compositions and methods of their use are provided for reducing inflammation in a subject, blocking leukocyte recruitment, inhibiting tumor metastasis, treating sepsis and preventing/reducing acute kidney injury.

13 Claims, 23 Drawing Sheets

Specification includes a Sequence Listing.

(56) References Cited

U.S. PATENT DOCUMENTS

2015/0225459 A1 8/2015 Robbins et al.
2017/0072006 A1* 3/2017 Robbins .................. A61P 35/04
2020/0069623 A1 3/2020 Tejedor Jorge

FOREIGN PATENT DOCUMENTS

WO WO 2004/010846 2/2004
WO WO 2006010496 2/2006
WO WO 2007/146188 12/2007
WO WO 2011/112435 9/2011
WO WO 2011/119484 9/2011
WO WO 2015-120536 8/2015
WO WO 2017/220810 12/2017

OTHER PUBLICATIONS

Gurulingappa, H. et al., "Synthesis and Evaluation of Aminophosphinic Acid Derivatives as Inhibitors of Renal Dipeptidase," Bioorganic & Medicinal Chemistry Letters 14, (2004) 3531-3533 (3 pages).
International Search Report and Written Opinion form Corresponding International Application PCT/IB2016/001244, mailed Jan. 19, 2017 (16 pages).
Paget S (1989) The distribution of secondary growths in cancer of the breast. 1889. Cancer Metastasis Rev 8(2):98-101.
Chiang AC & Massague J (2008) Molecular basis of metastasis. N Engl J Med 359(26):2814-2823.
Nguyen DX, Bos PD, & Massague J (2009) Metastasis: from dissemination to organ-specific coloniza-tion. Nat Rev Cancer 9(4):274-284.
Bakalian S, Marshall JC, Logan P, Faingold D, Maloney S, Di Cesare S, Martins C, Fernandes BF, & Burnier MN, Jr. (2008) Molecular pathways mediating liver metastasis in patients with uveal melanoma. Clin Cancer Res 14(4):951-956.
Sato T (2010) Locoregional management of hepatic metastasis from primary uveal melanoma. Semin Oncol 37(2):127-138.
Scharffetter-Kochanek K, Lu H, Norman K, van Nood N, Munoz F, Grabbe S, McArthur M, Lorenzo I, Kaplan S, Ley K, Smith CW, Montgomery CA, Rich S, & Beaudet AL (1998) Spontaneous skin ulceration and defective T cell function in CD18 null mice. J Exp Med 188(1):119-131.
Hess KR, Varadhachary GR, Taylor SH, Wei W, Raber MN, Lenzi R, & Abbruzzese JL (2006) Metastatic patterns in adenocarcinoma. Cancer 106(7):1624-1633.
Jones S, Chen WD, Parmigiani G, Diehl F, Beerenwinkel N, Antal T, Traulsen A, Nowak MA, Siegel C, Velculescu VE, Kinzler KW, Vogelstein B, Willis J, & Markowitz SD (2008) Comparative lesion sequencing provides insights into tumor evolution. Proc Natl Acad Sci U S A 105(11):4283-4288.
Roberge D, Hickeson M, Charest M, & Turcotte RE (2010) Initial McGill experience with fluorodeoxy-glucose pet/ct staging of soft-tissue sarcoma. Curr Oncol 17(6):18-22.
Du YC, Chou CK, Klimstra DS, & Varmus H (2011) Receptor for hyaluronan-mediated motility isoform B promotes liver metastasis in a mouse model of multistep tumorigenesis and a tail vein assay for metastasis. Proc Natl Acad Sci U S A 108(40):16753-16758.
Bemmo A, Dias C, Rose AA, Russo C, Siegel P, & Majewski J (2010) Exon-level transcriptome profil-ing in murine breast cancer reveals splicing changes specific to tumors with different metastatic abilities. PLoS One 5(8):e11981.
Tabaries S, Dong Z, Annis MG, Omeroglu A, Pepin F, Ouellet V, Russo C, Hassanain M, Metrakos P, Diaz Z, Basik M, Bertos N, Park M, Guettier C, Adam R, Hallett M, & Siegel PM (2011) Claudin-2 is selectively enriched in and promotes the formation of breast cancer liver metastases through engagement of integrin complexes. Oncogene 30(11):1318-1328.
Tabaries S, Dupuy F, Dong Z, Monast A, Annis MG, Spicer J, Ferri LE, Omeroglu A, Basik M, Amir E, Clemons M, & Siegel PM (2012) Claudin-2 promotes breast cancer liver metastasis by facilitating tumor cell interactions with hepatocytes. Mol Cell Biol.
Kang Y, Siegel PM, Shu W, Drobnjak M, Kakonen SM, Cordon-Cardo C, Guise TA, & Massague J (2003) A multigenic program mediating breast cancer metastasis to bone. Cancer Cell 3(6):537-549.
Minn AJ, Gupta GP, Siegel PM, Bos PD, Shu W, Giri DD, Viale A, Olshen AB, Gerald WI, & Mas-sague J (2005) Genes that mediate breast cancer metastasis to lung. Nature 436(7050):518-524.
Bos PD, Zhang XH, Nadal C, Shu W, Gomis RR, Nguyen DX, Minn AJ, van de Vijver MJ, Gerald WI, Foekens JA, & Massague J (2009) Genes that mediate breast cancer metastasis to the brain. Nature 459(7249):1005-1009.
Landemaine T, Jackson A, Bellahcene A, Rucci N, Sin S, Abad BM, Sierra A, Boudinet A, Guinebretiere JM, Ricevuto E, Nogues C, Briffod M, Bieche I, Cherel P, Garcia T, Castronovo V, Teti A, Lidereau R, & Driouch K (2008) A six-gene signature predicting breast cancer lung metastasis. Cancer Res 68(15):6092-6099.
Minn AJ, Kang Y, Serganova I, Gupta GP, Giri DD, Doubrovin M, Ponomarev V, Gerald WI, Blasberg R, & Massague J (2005) Distinct organ-specific metastatic potential of individual breast cancer cells and primary tumors. J Clin Invest 115(1):44-55.
Zhang XH, Wang Q, Gerald W, Hudis CA, Norton L, Smid M, Foekens JA, & Massague J (2009) Latent bone metastasis in breast cancer tied to Src-dependent survival signals. Cancer Cell 16(1):67-78.
Massague J (2007) Sorting out breast-cancer gene signatures. N Engl J Med 356(3):294-297.
Ruoslahti E (2004) Vascular zip codes in angiogenesis and metastasis. Biochem Soc Trans 32(Pt3):397-402.
Teesalu T, Sugahara KN, & Ruoslahti E (2012) Mapping of Vascular ZIP Codes by Phage Display. Methods Enzymol 503:35-56.
Powell et al., Peptide stability in drug development. II. Effect of single amino acid substitution and glycosylation on peptide reactivity in human serum. Pharm. Res. 10:1268-1273 (1993).
Brady and Dodson, Drug design. Reflections on a peptide. Nature 368:692-693 (1994).
Jameson et al., A rationally designed CD4 analogue inhibits experimental allergic encephalomyelitis. Nature 368:744-746 (1994)).
Andonegui G, et al., Mice that exclusively express TLR4 on endothelial cells can efficiently clear a lethal systemic Gram-negative bacterial infection., J Clin Invest. Jul. 2009;119(7):1921-30.
Yipp BG, et al,. Profound differences in leukocyte-endothelial cell responses to lipopolysaccharide ver-sus lipoteichoic acid., J Immunol. May 1, 2002;168(9):4650-8.
Fauchere et al., Infect. Immun. 54:283-287 (1986).
Evans et al., J. Med. Chem. 30:1229-1239 (1987).
Spatola et al. Life Sci. 38:1243-1249 (1986).
Vale et al., Science 213:1394-1397 (1981).
R Nagano et al: "Therapeutic Efficacy of BO-3482, A Novel Dithiocarbamate Carbapenem, in Mice Infected with Methicillin-Resistant *Staphylococcus aureus*", Antimicrobial Agents and Chemotherapy, Oct. 1, 1997 (Oct. 1, 1997), pp. 2278-2281.
Mummert M E et al: "Development of a Peptide Inhibitor of Hyaluronan-Mediated Leukocyte Trafficking", The Journal of Experimental Med1, Rockefeller University Press, US, vol. 192, No. 6, Sep. 18, 2000. (Sep. 18, 2000), pp. 769-779.
Del Valle et al., "Efficacy and Safety oflmipenem/Cilastatin in the Empirical Treatment of Septicemia," Scand J Infect Dis Suppl. 52:20-25, 1987.
Kabbara et al., "Evaluation of the appropriateness of imipenem/cilastatin prescription and dosing in a tertiary care hospital," Infection and Druz Resistance 8:31-38, 2015.
A. Zarjou et al., "Sepsis and Acute Kidney Injury," Journal of the American Society of Nephrology., vol. 22, No. 6, May 12, 2011 (May 12, 2011), pp. 999-1006.
Miller, Ronald et al., Mechanisms of Cisplatin Nephrotoxicity11 , Toxins, vol. 2, No. 11, Oct. 26, 2010, pp. 2490-2518.
Database Medline [Online] US National Library of Medicine (NLM), Bethesda, MD, US; Jun. 2004 (Jun. 2004), Cao Yong-Qian et al: [Clinical analysis of severe burn patients with sepsis during shock stage].

(56) References Cited

OTHER PUBLICATIONS

Dyson A, Singer M. Animal models of sepsis: Why does preclinical efficacy fail to translate to the clinical setting? Crit Care Med. 2009;37(1 Suppl): S30-S37.
Rittirsch D, Hoesel LM, Ward PA. The disconnect between animal models of sepsis and human sepsis. J Leukoc Biol. 2007;81(1):137-143.
Remick DG, Newcomb DE, Bolgos GL, Call DR. Comparison of the mortality and inflammatory response of two models of sepsis: lipopolysaccharide vs. cecal ligation and puncture. Shock. 2000;13(2):110-116.
Response to Third Party Observations filed for European Patent Application No. 17731188.3 on May 27, 2020.
Lee Hing-Chung et al: "Treatment of Tularemia With Imipenem/Cilastatin Sodium", Southern Medical Journal, vol. 84, No. 10, Oct. 1, 1991 (Oct. 1, 1991), pp. 1277-1278.
Hase Isano et al: "[Legionnaires' disease with acute renal failure caused by Legionella pneumophilla serogroup 4]—PubMed", Jan. 1, 2005 (Jan. 1, 2005), pp. 1-1.
Park Sung Wook et al: "Stability of New Carbapenem DA-1131 to Renal Dipeptidase (Dehydropeptidase I)", Antimicrobial Agents and Chemotherapy, vol. 46, No. 2, Feb. 1, 2002 (Feb. 1, 2002), pp. 575-577.

* cited by examiner

Rat DPEP1 Transfected Cos-1

DPEP1 (Human) Transfected Cos-1

Control- Mock Transfected Cos-1 (LF2000)
CL – Cilastatin
Pen – L-Penicillamine

DPEP-1 BINDING COMPOSITIONS AND METHODS OF USE

CROSS REFERENCE TO RELATED APPLICATIONS

This application is a continuation of U.S. patent application Ser. No. 16/504,909, filed Jul. 8, 2019, which is a continuation of U.S. patent application Ser. No. 15/234,521, filed Aug. 11, 2016, which claims the benefit of U.S. provisional patent application 62/203,704 filed Aug. 11, 2015 and U.S. provisional patent application 62/264,032 filed Dec. 7, 2015. The contents of each of the above-identified applications is fully incorporated herein by reference.

SEQUENCE LISTING

The instant application contains a Sequence Listing which has been filed electronically in XML format and is hereby incorporated by reference in its entirety. Said XML copy, created on Sep. 19, 2023, is named 16143_105068_CON2_8013_US03_SL.xml and is 59,362 bytes in size.

FIELD OF THE INVENTION

The present invention relates to pharmaceutical compositions and methods of their use for reducing inflammation in a subject, blocking leukocyte recruitment, inhibiting tumor metastasis, treating sepsis and preventing/reducing acute kidney injury.

BACKGROUND OF THE INVENTION

Inflammation is a host defense reaction to harmful stimuli. Acute inflammation is characterized by redness, heat, swelling, and pain. The primary objectives of inflammation are to localize and eradicate the irritant and promote repair of the surrounding tissue. In most instances, inflammation is a necessary and beneficial process.

The inflammatory response involves three major stages: first, dilation of arterioles to increase blood flow; second, microvascular structural changes and escape of plasma proteins from the bloodstream; and third, leukocyte transmigration through endothelium and accumulation at the site of injury. Leukocyte transendothelial migration (TEM) is a key step in their recruitment to sites of inflammation, injury, and immune reactions. The emigration of neutrophils to sites of inflammation is thought to require intercellular adhesion.

Inflammation can be acute or chronic. Failure to resolve the harmful stimuli prompting acute inflammation can lead to chronic inflammation but some stimuli are just more likely to prompt chronic inflammation. In some instances, inflammation results in secondary or chronic damage. Inflammation in a tumor microenvironment has also been implicated in cancer acceleration and tumor metastasis (Wu et al., Cell Cycle. 2009 Oct. 15; 8(20):3267-73, Geng et al., PLOS One. 2013; 8(1) e54959). The presence of pro-inflammatory molecules enable malignant cancer cells to adhere to the endothelial wall, leading to metastasis. Pro-inflammatory cytokines induce proliferation and aggregation of cancer cells, triggering other cancer cells to secrete more cytokines, resulting in a positive feedback loop. The role of adhesion molecules in acute and chronic inflammation is an area of study to develop methods of controlling inflammation by modulating or blocking leukocyte adhesion to the endothelium.

Anti-inflammatory agents function as blockers, suppressors, or modulators of the inflammatory response. Tissue-specific control of inflammation is sometimes desirable to modulate inflammation in one tissue while maintaining the response in other tissues. Anti-inflammatory agents are used to treat various acute and chronic conditions. Most people have no trouble taking these agents, however some people develop side-effects which can be serious. In some groups, these medicines are prescribed with caution and only where there are no alternatives and at the lowest doses and durations necessary.

Recognition of non-self-molecular patterns by pattern recognition receptors is a cornerstone of innate immunity. Study of the innate immune system has also revealed the existence of dinucleotide receptors for sensory and signaling that activate inflammatory responses (Cai et al., 2014). The dinucleotide receptor STING is used to induce type I IFNs (Ishikawa 2009). These systems are pervasive in mammals and other animals. If there are dinucleotide receptors, there are likely dipeptide receptors that function in a similar manner. Pro-inflammatory dipeptide receptor cellular signaling systems provide another therapeutic approach to modulate inflammation and treat acute and chronic inflammation-mediated diseases.

There remains a need for additional therapeutic compounds for reducing or blocking inflammation. What is therefore needed are compositions to function as blockers, suppressors, or modulators of the inflammatory response. What is also needed are novel targets and methods of modulating inflammation via these targets.

SUMMARY OF THE INVENTION

The DPEP-1 pathway is a novel pathway for modulating inflammation, leukocyte recruitment and tumor metastasis. The compositions and methods provided herein provide a novel and unique approach to the modulation of inflammation, tumor metastasis and treatment of related conditions.

In a first aspect, the invention provides DPEP-1 binding compositions comprising an effective amount of a compound that binds to DPEP-1.

In one embodiment, the compound is selected from a competitive antagonist, a non-competitive antagonist, and uncompetitive antagonist, or a silent antagonist of DPEP-1.

In one embodiment, the compound comprises a peptide.

In one embodiment, the peptide comprises an LSALT sequence (LSALTPSPSWLKYKAL) (SEQ ID NO:1).

In one embodiment, the peptide comprises an LSALT sequence and 1, 2, 3, 4, or 5 amino acid residues at the N-terminus and/or C-terminus of the LSALT sequence.

In one embodiment, the LSALT sequence is modified by pegylation, acetylation, glycosylation, biotinylation, or substitution with one or more D-amino acid and/or un-natural amino acid and combinations thereof.

In one embodiment, the LSALT sequence or additional residues at the N-terminus or C-terminus comprises one or more modified amino acid residues or amino acid analogs.

In one embodiment, the amino acid analogs are selected from P-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine.

In one embodiment, the modified amino acid residues are modified by methylation, amidation, acetylation, and/or substitution with other chemical groups.

In one embodiment, the peptide comprises a GFE tripeptide sequence.

In one embodiment, the peptide comprises the sequence: X1-G-F-E-X2, wherein X1 and X2 each is 1 to 10 independently selected amino acids. In one embodiment, the GFE peptide comprises the sequence CGFECVRQCPERC (GFE-1) (SEQ ID NO:2) or CGFELETC (GFE-2) (SEQ ID NO:3).

In one embodiment, the GFE-1 or GFE-2 peptide further comprises at least 1 to 5 additional amino acids on the N- and C-terminus of the peptide.

In one embodiment, the GFE-1 or GFE-2 peptide further comprises at least 1 to 5 additional amino acids on the N- or C-terminus of the peptide.

In one embodiment, the GFE-1 or GFE-2 peptide is not conjugated to cilastatin.

In one embodiment, the GFE peptide is modified by pegylation, acetylation, glycosylation, biotinylation, or substitution with one or more D-amino acid and/or un-natural amino acid.

In one embodiment, the GFE peptide or additional residues at the N-terminus or C-terminus comprise one or more modified amino acid residues or amino acid analogs.

In one embodiment, the amino acid analogs are selected from P-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine.

In one embodiment, the modified amino acid residues are modified by methylation, amidation, acetylation, and/or substitution with other chemical groups.

In one embodiment, the compound comprises a blocking antibody.

In one embodiment, the blocking antibody reduces, antagonizes, or blocks DPEP-1 activity.

In one embodiment, the compound comprises a small molecule.

In one embodiment, the small molecule reduces, antagonizes, or blocks DPEP-1 activity.

In one embodiment, the small molecule is cilastatin.

In one embodiment, the small molecule is an aminophosphinic acid derivative.

In one embodiment, the aminophosphinic acid derivative has the formula.

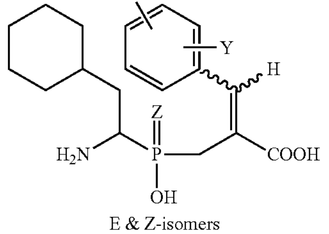

E & Z-isomers wherein X is selected from the group consisting of any halogen or C1 to C6 haloalkyl or C1 to C6 di- or trihaloalkyl or C1 to C6 alkyl, $CF_3NR'$, or F, Cl, Br, $I^{125}$, I, $CF_3NR'$. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, $N(C1\text{ to }C6\text{ alkyl})_2$, and NH(C1 to C6 alkyl); Z can be either O or S. X and Y can also be an amine selected from $NH_2$, $N(C1\text{ to }C6\text{ alkyl})_2$, and NH(C1 to C6 alkyl).

In one embodiment, a pharmaceutical composition is provided comprising the compound and pharmaceutically acceptable carrier.

In one embodiment, the carrier is selected from water, saline, phosphate buffered saline, Ringer's solution, dextrose solution, serum-containing solutions, Hank's solution, oils, esters and glycols.

In one embodiment, the pharmaceutical composition is suitable for parenteral administration.

In one embodiment, the pharmaceutical composition is suitable for intravenous administration.

In one embodiment, the compound is administered at a dosage between about 0.01 mg/kg and about 100 mg/kg.

In a second aspect, the invention provides a method for treating inflammation in a subject in need thereof, comprising administering an effective amount of a composition that binds to DPEP-1 to the subject, thereby treating inflammation. In one embodiment, the inflammation is associated with acute kidney injury.

In one embodiment, inflammation is characterized by a profile of inflammatory markers selected from IL-12, IP-10, IL-1b, IL-5, GM-CSF, IFN Gamma, or IL-1a.

In one embodiment, the method further comprises identifying the subject in need of treatment by performing a diagnostic test to determine a need for reduction in inflammation. Indications for treatment include, but are not limited to, clinical signs and symptoms in any patient that is at risk for acute kidney injury (pre-operatively or before administering intravenous contrast) or in any patient having decreasing urine output or increasing serum creatinine, such as in a patient with a systemic infection or low blood pressure.

In a third aspect, the invention provides a method for blocking leukocyte recruitment in a subject in need thereof, comprising administering an effective amount of a composition that binds to DPEP-1 to the subject, thereby blocking leukocyte recruitment.

In one embodiment, the method further comprises identifying the subject in need of treatment by performing a diagnostic test for to determine a need for blocking leukocyte recruitment Indications for treatment include, but are not limited to, clinical signs and symptoms in any patient that is at risk of increasing leukocyte recruitment.

In a fourth aspect, the invention provides a method for reducing or preventing tumor metastasis in a subject in need thereof, comprising administering an effective amount of a composition that binds to DPEP-1 to the subject, thereby reducing or preventing tumor metastasis.

In one embodiment, the method further comprises identifying the subject in need of treatment by detecting DPEP-1 is a tumor sample from the subject.

In a fifth aspect, the invention provides a method for treating or preventing leukocyte recruitment and inflammation during sepsis in a subject in need thereof, comprising administering an effective amount of a composition that binds to DPEP-1 to the subject, thereby reducing or preventing the organ complications of sepsis such as acute kidney, lung or liver injury. In one embodiment, the method reduces or prevents organ damage associated with sepsis.

In one embodiment, the invention provides a method for treating or preventing leukocyte recruitment and inflammation during sepsis.

In another embodiment, binding DPEP-1 reduces or prevents organ complications of sepsis such as acute kidney, lung or liver injury.

In one embodiment, the method further comprises identifying a subject in need of treatment by performing a diagnostic test to determine a need for reduction or prevention of sepsis. In one embodiment, the method further comprises reduction or prevention of leukocyte recruitment and inflammation during sepsis. Indications for treatment include, but are not limited to, clinical signs and symptoms of sepsis, pneumonia, a rising neutrophil count or positive blood cultures for bacteria.

In one embodiment, the sepsis is caused by a bacterial, viral, fungal or parasite infection.

In one embodiment, the sepsis is caused by bacterial infection, i.e., bacterial sepsis.

In one embodiment, the invention includes a method of treating a symptom of sepsis in a patient comprising administering to the patient an effective amount of a composition comprising an antagonist compound of DPEP-1.

In one embodiment, the composition is administered until symptoms of sepsis are reduced or ameliorated.

In a sixth aspect, the invention provides a method for treating or preventing acute kidney injury in a subject in need thereof, comprising administering an effective amount of a composition that binds to DPEP-1 to the subject, thereby reducing or preventing acute kidney injury. In one embodiment, the method reduces or prevents the leukocyte recruitment and inflammation that is associated with acute kidney injury.

In one embodiment, the method further comprises identifying the subject in need of treatment by performing a diagnostic test to determine a need for prevention of acute kidney injury.

In exemplary embodiments, the acute kidney injury is caused by ischemia/reperfusion, shock, sepsis, or by toxic agents such as antibiotics or intravenous radiographic contrast. In one embodiment, the composition is used to reduce kidney inflammation during sepsis, allergy or environmental hypersensitivity.

In one embodiment, the acute kidney injury is associated with sepsis.

In one embodiment, the acute kidney injury is associated with ischemia reperfusion.

In a seventh aspect, the invention a method for treating or preventing ischemia reperfusion injury in a subject in need thereof, comprising administering an effective amount of a composition that binds to DPEP-1 to the subject, thereby reducing or preventing ischemia-reperfusion injury. In one embodiment, the method reduces or prevents the leukocyte recruitment and inflammation that is associated with ischemia-reperfusion injury.

In one embodiment, the method further comprises identifying the subject in need of treatment by performing a diagnostic test to determine a need for reduction or prevention of ischemiareperfusion injury. Indications for treatment include, but are not limited to, clinical signs and symptoms of ischemia-reperfusion injury, or potential or risk for a subject to have an ischemiareperfusion injury.

In an eight aspect, the invention provides a method for reducing or preventing ischemia-reperfusion injury related disorders in a subject in need thereof, comprising administering an effective amount of a composition that binds to DPEP-1 to the subject, thereby reducing or preventing ischemia-reperfusion injury.

In one embodiment, the ischemia-reperfusion injury related disorder is associated with ischemic and post-ischemic events in organs and tissues, and the disorder is selected from a group consisting of thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure (including heart failure, liver failure, kidney failure and the like); restenosis; atherosclerosis; thrombosis; platelet aggregation; shock liver; spinal cord injury; brain injury or following conditions selected from a list comprising of procedures such as peri-operative procedures, cardiac surgery; organ surgery; organ transplantation; angiography; cardiopulmonary and cerebral resuscitation.

In one embodiment, the ischemia-reperfusion injury is associated with harvesting donor organs for transplantation.

In one embodiment, the ischemia-reperfusion injury is associated with allograft organs during donor procurement, ex vivo handling or implantation into a transplant recipient.

In various embodiments, the composition can be administered (i) prior to, during or following harvesting a donor organ which will be transplanted or (ii) prior to or during a surgical procedure in which ischemia is expected.

In a ninth aspect, the invention provides a method for screening for compounds that bind to DPEP-1.

In one embodiment, the screening method comprises a competitive binding assay using an LSALT or GFE peptide.

In one embodiment, the screening method comprises identifying a compound effective to decrease inflammation in a tissue of a patient comprising: (a) screening a library of test compounds for their ability to bind to DPEP-1 in the tissue; (b) selecting candidate test compounds that show selective binding affinity; (c) testing the candidate compounds for inflammation reducing activity, and (d) selecting a candidate compound if it decrease inflammation, thereby providing a compound effective to decrease inflammation.

In one embodiment, the tissue is lung tissue or liver tissue.

In one embodiment, the method further comprises the steps of (e) further testing the compound for its ability to inhibit tumor metastasis in a patient bearing a solid tumor; and (f) selecting the compound if it inhibits tumor metastasis in step (e).

In one embodiment, the method further comprises the steps of (e) further testing the compound for its ability to inhibit tumor metastasis to the lungs and liver in a patient bearing a solid tumor known to metastasize the lungs or liver; and (f) selecting the compound if it inhibits tumor metastasis in step (e).

In one embodiment, the method further comprises the steps of (e) further testing the compound for its ability to treat bacterial sepsis in a patient, and (f) selecting the compound if it treats sepsis in step (e).

In one embodiment, the method further comprises the steps of (e) further testing the compound for its ability to treat acute kidney damage in a patient; and (f) selecting the compound if it treats acute kidney damage in step (e).

Any of the compositions of the present invention described herein may be used with these methods.

These and other objects and features of the invention will become more fully apparent when the following detailed description of the invention is read in conjunction with the accompanying drawings.

BRIEF DESCRIPTION OF THE DRAWINGS

FIG. 11B provides photomicrographic images of kidney after LPS (90 min), alone and with inhibitors. Neutrophils were quantified over a 90 min. time course after LPS injection with various DPEP-1 inhibitors and are shown graphically in FIG. 11C.

DETAILED DESCRIPTION

I. Definitions

Figure 1A:
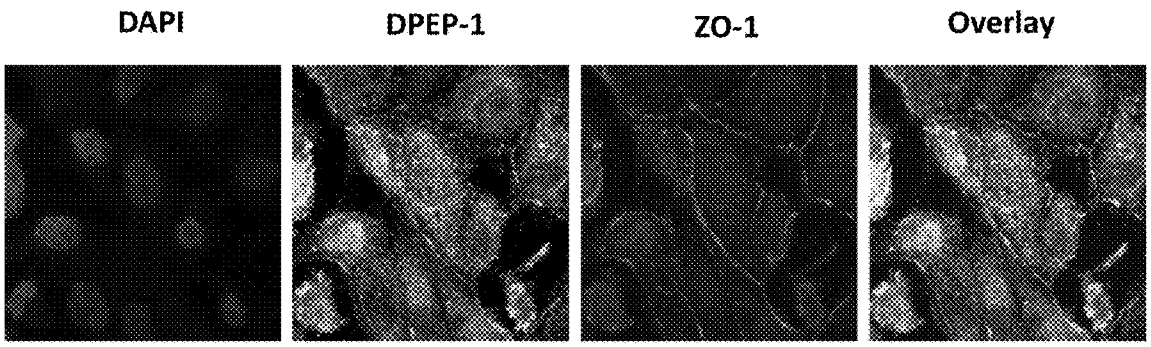
FIG. 1A provides representative photomicrographs of renal tubular epithelial cells (TEC) isolated and cultured from human kidney nephrectomies and labeled with DPEP-1 and ZO-1 (a TEC surface marker).

Where a term is provided in the singular, the inventors also contemplate aspects of the invention described by the plural of that term. As used in this specification and in the appended claims, the singular forms “a”, “an” and “the” include plural references unless the context clearly dictates otherwise, e.g., “a peptide” includes a plurality of peptides. Thus, for example, a reference to “a method” includes one or more methods, and/or steps of the type described herein and/or which will become apparent to those persons skilled in the art upon reading this disclosure.

The term “administer”, “administering” or “administered” means the act of giving an agent or therapeutic treatment to a physiological system (e.g., a subject or in vivo, in vitro, or ex vivo cells, tissues, and organs).

The term “diagnosed”, “diagnostic” or “diagnosed” means identifying the presence or nature of a pathologic condition. Diagnostic methods include observations and assays, and differ in their sensitivity and specificity. The “sensitivity” of a diagnostic observation or assay is the percentage of diseased individuals who test positive (percent of “true positives”). Diseased individuals not detected by the observation or assay are “false negatives.” Subjects who are not diseased and who test negative in the observation or assay are termed “true negatives.” The “specificity” of a diagnostic observation or assay is 1 minus the false positive rate, where the “false positive” rate is defined as the proportion of those without the disease who test positive. While a particular diagnostic method may not provide a definitive diagnosis of a condition, it suffices if the method provides a positive indication that aids in diagnosis.

As used herein, the terms "treat", "treatment" and "treating" refer to the prevention, reduction or amelioration of the progression, severity, and/or duration of at least one symptom of any condition or disease. The term "treatment" or "treating" refers to any administration of a compound of the present invention and includes (i) inhibiting the disease, or the disease state in an individual that is experiencing or displaying the pathology or symptomatology of the disease, or the disease state (i.e., arresting further development of the pathology and/or symptomatology) or (ii) ameliorating the disease in an individual that is experiencing or displaying the pathology or symptomatology of the disease, or the disease state (i.e., reversing the pathology and/or symptomatology). The term "controlling" includes preventing, treating, eradicating, ameliorating or otherwise reducing the severity of symptoms of the disease, or the disease state.

As is relates to cancer, the terms "treat", "treatment" and "treating" refer to the reduction or amelioration of the progression, severity, and/or duration of cancer, particularly a solid tumor, or one or more symptoms thereof that results from the administration of one or more therapies (e.g., one or more prophylactic and/or therapeutic agents). In exemplary embodiments, treatment of a solid tumor refers to one or more of (i) reducing the number of cancer cells; (ii) increasing tumor cell apoptosis, (iii) reducing tumor size; (iv) reducing tumor volume; (v) inhibiting, retarding, slowing to some extent, and preferably stopping cancer cell infiltration into peripheral organs; (vi) inhibiting (e.g., slowing to some extent and preferably stopping) tumor metastasis; (vii) inhibiting tumor growth, (viii) preventing or delaying occurrence and/or recurrence of a tumor; (ix) reduction of a cancer marker that is associated with the presence of cancer; and/or (ix) relieving to some extent one or more of the symptoms associated with the cancer. "Treatment" can also mean prolonging survival as compared to expected survival if not receiving treatment Standard methods can be used to measure the magnitude of this effect, such as in vitro assays with purified enzyme, cell-based assays, animal models, or human testing. For example, an immunohistochemical analysis of a cancer tumor of the patient may show a significant increase in tumor cell apoptosis when the present invention is administered to the patient. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, the term "effective amount" refers to the amount of a therapy (e.g. a prophylactic or therapeutic agent) which is sufficient to effect beneficial or desired results, including clinical results. An effective amount can be administered in one or more administrations.

As used herein, the term "inflammatory disease" refers to diseases (treatable or preventable with compounds described herein) including, but not limited to, a. leukocyte recruitment, adhesion or activation and other disorders that involve neutrophils, monocytes, lymphocytes or macrophages, b. diseases involving the pathological production of inflammatory cytokines (e.g. TNF-a, interleukin (IL)-Ip, IL-2, IL-6) c. activation of nuclear factors that promote transcription of genes encoding inflammatory cytokines. Examples of these nuclear transcription factors include but are not restricted to: nuclear factor-KB (NF-B), activated protein-1 (AP-1), nuclear factor of activated T cells (NFAT).

The term "subject" or "patient" or synonym thereto, as used herein includes all members of the animal kingdom, especially mammals, including human. The subject or patient is suitably a human.

The term "pharmaceutically acceptable carrier" refers to any such carriers known to those skilled in the art to be suitable for the particular mode of administration. For example, the term "pharmaceutically acceptable carrier" includes any and all solvents, dispersion media, coatings, antibacterial and antifungal agents, isotonic and absorption delaying agents and the like, that may be used as a media for a pharmaceutically acceptable substance. In addition, the active materials can also be mixed with other active materials that do not impair the desired action, or with materials that supplement the desired action, or have another action.

The term "pharmaceutically acceptable salt" as used herein refers to salts which are known to be non-toxic and are commonly used in the pharmaceutical literature. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, betahydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

II. DPEP-1

DPEP-1, also known as renal dipeptidase, microsomal dipeptidase, or dehydropeptidase-1 and currently classified as EC 3.4.13.19 (previously EC 3.4.13.11), is a plasma membrane glycosyl phosphatidylinositol-anchored glycoprotein (Keynan et al., in Hooper (Ed) Zinc Metalloproteases in Health and Disease Taylor and Francis, London pages 285-309 (1996), which is incorporated herein by reference). This zinc metalloprotease, which is expressed mainly in lung and kidney brush border, is involved in vivo in renal metabolism of glutathione and in pulmonary metabolism of peptidyl leukotrienes. In addition, DPEP-1 is the only known example of a mammalian beta-lactamase and is also involved in the metabolism of glutathione, leukotriene and D4. DPEP-1 forms a disulfide-linked homodimer, with the molecular weight of the monomer ranging from about 48 to 59 kDa depending on the species of origin (Keynan et al., Biochem. 35:12511-12517 (1996), which is herein incorporated by reference, see, also, Example IVB).

Dipeptidase expression has been detected in several tissues although it is expressed mainly in lung and kidney There have been reports of low levels of DPEP-1 activity in total extracts from liver, spleen, small intestine and brain, while others have found no detectable activity in these organs. In the mouse, four distinct DPEP-1 mRNAs are present, and they are differentially expressed in several organs (Habib et al., J Biol. Chem 271:16273-16280 (1996)). Organ-specific differences in the nature and extent of pig DPEP-1 N-linked glycosylation also have been reported (Hooper et al., Biochem. J. 324:151-157 (1997)).

In the kidney, DPEP-1 expression is restricted to epithelial cells in the brush border region of the proximal tubules. In the lung, DPEP-1 expression has been detected in many cell types including endothelial cells as well as epithelial cells of the conducting airways, alveolar ducts, capillaries, and the basement membrane of alveoli and terminal bronchioles (Habib et al., supra, 1996); Inamura et al., Prostaglandins Leukotrienes and Essential Fatty Acids 50:85-92 (1994)). DPEP-1 expression also has been observed on endothelial cells of submucosal microvessels in the human trachea (Yamaya et al., Resp. Physiol. 111:101-109 (1998)) The level of DPEP-1 activity is highest in lung (Hirota et al., Eur. J. Biochem. 160:521-525 (1986); Habib et al., Proc. Natl. Acad. Sci. USA 95:4859-4863 (1998)). This expression pattern correlates with the strong lung homing of molecules such as GFE-1.

While not to be bound by a particular theory, it is believed that the DPEP-1 receptor functions as a leukocyte adhesion molecule or a tumor cell adhesion molecule expressed on vascular endothelium, or other parenchymal cells such as the kidney tubular epithelium Adhesion molecules are involved in the recruitment process, which are surface bound glycoprotein molecules expressed on leukocytes and/or endothelial cells. A key step in leukocyte recruitment is firm adhesion of leukocyte on the surface of the endothelium, which positions the leukocyte to migrate into the vessel wall through a sequence of adhesion and activation events to exerts its effects on the inflamed site. DPEP-1 could also function as a peptide detection system during organ injury or infection. One such peptide detection system is the so-called pattern recognition receptors (PRR) to detect key molecular signatures of invading pathogens, i.e., pathogen-associated molecular patterns (PAMPS), thereby triggering the innate immune system (Janeway, C, et al., Annu. Rev. Immunol, 20 (2002), pp. 197216). Examples of PRR are (toll-like receptors) TLRs, which detect bacterial or viral products such as LPS (TLR4) (Bell, J. K. et al., Trends Immunol, 24 (2003), pp. 528-533).

TLRs are transmembrane receptors that recognize pathogen-associated molecular patterns (PAMPs) through leucine-rich repeats (LRRs) in their extracellular domains that are implicated in ligand binding and auto-regulation (Kawai et al, Cell Death Differ. 13, 816-825, 2006). TLRs recognize microbial structures in the earliest phase of the host defense response, and induce the expression of many immune and inflammatory genes, the products of which are tailored to drive the immune mechanisms necessary for eliminating the invading pathogen. TLRs have also been implicated in the recognition of damage-associated molecular patterns (DAMPs) and are becoming increasingly recognized as regulators of tumor-promoting inflammation and promoters of tumor survival signals. Other activators of such cellular pathways may provide effective therapeutic targets to treat pathogen and damage-associated cellular inflammation.

As used herein, the terms "dipeptidase", and "membrane dipeptidase" are synonymous with "DPEP-1" and refers to the enzyme currently classified as BC 3.4.13.19 (previously EC 3.4.13.11) and also known as renal or microsomal dipeptidase or dehydropeptidase-1.

The term "selectively inhibits", as used herein in reference to a DPEP-1 enzymatic activity, means that the binding agent decreases DPEP-J activity in a manner that is selective for the DPEP-1 enzyme as compared to related but different enzymes such as other proteases. Thus, an DPEP-1 binding agent is distinct from a non-specific inhibitor of, for example, zinc metalloproteases. Thus, an DPEP-1 binding agent can selectively decrease DPEP-1 activity while having little or no effect on the activity of, for example, dipeptidyl peptidase IV. In one embodiment, the binding agent is a competitive inhibitor to prevent binding to DPEP-1.

The term "selectively binds", as used herein in reference to a DPEP-1 binding agent, means that the binding agent decreases DPEP-1-mediated leukocyte recruitment in a manner that is selective for the DPEP-1 receptor as compared to related but different receptors. DPEP-1 binding agent also refers to decreasing DPEP-1-mediated leukocyte recruitment where the DPEP-1 acts as an adhesion molecule for leukocytes or tumor cells independent of its enzymatic activity. Thus, an DPEP-1 binding agent can selectively decrease DPEP-1-mediated leukocyte recruitment while having little or no effect on the activity of, for example, dipeptidyl peptidase IV In one embodiment, the binding agent is a competitive inhibitor to prevent binding to DPEP-1.

The term specific binding, as used herein, includes both low and high affinity specific binding. Specific binding can be exhibited, for example, by a low affinity DPEP-1-binding molecule having a Kd for membrane dipeptidase of about $10^{-4}$ M to about $10^{-7}$ M. Specific binding also can be exhibited by a high affinity DPEP-1-binding molecule, for example, a DPEP-1-binding molecule having a Kd for membrane dipeptidase of at least about $10^{-7}$ M, at least about $10^{-8}$ M, at least about $10^{-9}$ M, at least about $10^{-10}$ M, or at least about $10^{-11}$ M or $10^{-12}$ M or greater. A DPEP-1-binding peptide including an LSALT or GFE peptide, where $X_1$ and $X_2$ each is 1 to 10 independently selected amino acids, can have, for example, a Kd for membrane dipeptidase of about $2\times10^{-5}$ M to $10^{-7}$ M, for example, a Kd of about $10^{-6}$ to $10^{-7}$ M. Both low and high affinity DPEP-1-binding molecules that selectively bind to lung or kidney endothelium can be useful in the methods described herein.

III. DPEP-1 Binding Agents

The present invention is based on the discovery that binding or blocking DPEP-1 has utility for reducing inflammation-mediated diseases in lung and kidney, for example, during sepsis or acute kidney injury. The present invention is also based on the observation that binding to or blocking DPEP-1 also has utility for reducing tumor metastasis. Agents that bind to DPEP-1 are particularly useful in the methods described herein. Such agents may include but are not limited to peptides, antibodies and small molecule agents. Variants and modified embodiments of these binding agents that are capable of being used in these methods are also provided.

A. LSALT Peptide

Using an unbiased combinatorial phage in vivo biopanning approach, a specific peptide-displaying-phage was isolated that localized to the liver and lungs of animals treated with a pro-inflammatory stimulus and blocks leukocyte recruitment. This phage and its corresponding displayed peptide (N-LSALTPSPSWLKYKAL called LSALT or Metablok™,) (SEQ ID NO: 1) were also found to dramatically reduce tumor burden in the livers or lungs of animals injected with a tumor cell line LSALT is capable of binding to DPEP-1 and reducing the inflammatory profile of a tissue thereby providing several therapeutically useful actions. The peptide also reduced neutrophil recruitment to the liver in a mouse model of sepsis.

The LSALT peptide, as well as variants and modified versions thereof are described herein. Also described are pharmaceutical compositions comprising these peptides.

In some embodiments, the LSALT peptide contains one or more modifications to increase protease resistance, serum stability and/or bioavailability. In some embodiments, the modification is selected from pegylation, acetylation, glycosylation, biotinylation, substitution with D-amino acid and/or un-natural amino acid, and/or cyclization of the peptide.

In certain embodiments, the LSALT peptide contains one or more L-amino acids, D-amino acids, and/or non-standard amino acids.

In various embodiments, the LSALT peptide further comprises amino acid residues or analogues at the C-terminus, the N-terminus or both the C-terminus and the N-terminus Preferably the activity bearing sequence of the LSALT peptide is not appreciably impacted by the addition of these additional amino acid.

In one embodiment, the LSALT peptide, further comprises 1, 2, 3, 4, or 5 amino acid residues at the N-terminus and C-terminus of the LSALT peptide.

In another embodiment, the LSALT peptide, further comprises 1, 2, 3, 4, or 5 amino acid residues at the N-terminus of the LSALTPSPSWLKYKAL (SEQ ID NO.1) sequence.

In another embodiment, the LSALT peptide, further comprises 1, 2, 3, 4, or 5 amino acid residues at the C-terminus of the LSALTPSPSWLKYKAL (SEQ ID NO:1) sequence.

In various embodiments, the peptide is selected from XLSALTPSPSWLKYKAL (SEQ ID NO:4), XXLSALTPSPSWLKYKAL (SEQ ID NO:5), XXXLSALTPSPSWLKYKAL (SEQ ID NO:6), XXXXLSALTPSPSWLKYKAL (SEQ ID NO.7), or XXXXLSALTPSPSWLKYKAL (SEQ ID NO.7), where X is any naturally-occurring amino acid or where X is an unconventional amino acid or amino acid analog as described herein and known to those of skill in the art.

In various embodiments, the peptide is selected from LSALTPSPSWLKYKALX (SEQ ID NO:8), LSALTPSPSWLKYKALXX (SEQ ID NO:9), LSALTPSPSWLKYKALXXX (SEQ ID NO:10), LSALTPSPSWLKYKALXXXX (SEQ ID NO.11), or LSALTPSPSWLKYKALXXXX (SEQ ID NO.11), where X is any naturally-occurring amino acid or where X is an unconventional amino acid or amino acid analog as described herein and known to those of skill in the art.

In various embodiments, the peptide is selected from XLSALTPSPSWLKYKALX (SEQ ID NO:12), XLSALTPSPSWLKYKALXX (SEQ ID NO:13), XLSALTPSPSWLKYKALXXX (SEQ ID NO.14), XLSALTPSPSWLKYKALXXXX (SEQ ID NO:15), XLSALTPSPSWLKYKALXXXXX (SEQ ID NO:16), XXLSALTPSPSWLKYKALX (SEQ ID NO:17). XXLSALTPSPSWLKYKAXX (SEQ ID NO: 18), XXLSALTPSPSWLKYKALXXX (SEQ ID NO.19), XXLSALTPSPSWLKYKALXXXX (SEQ ID NO:20), XXLSALTPSPSWLKYKALXXXXX (SEQ ID NO:21), XXXLSALTPSPSWLKYKALX (SEQ ID NO:22), XXXLSALTPSPSWLKYKALXX (SEQ ID NO:23), XXXLSALTPSPSWLKYKALXXX (SEQ ID NO:24), XXXLSALTPSPSWLKYKALXXXX (SEQ ID NO:25), XXXLSALTPSPSWLKYKALXXXXX (SEQ ID NO:26), XXXXLSALTPSPSWLKYKALX (SEQ ID NO:27), XXXXLSALTPSPSWLKYKALXX (SEQ ID NO:28). XXXXLSALTPSPSWLKYKALXXX (SEQ ID NO:29), XXXXLSALTPSPSWLKYKALXXXX (SEQ ID NO.30), XXXXLSALTPSPSWLKYKALXXXXX (SEQ ID NO:31), XXXXXLSALTPSPSWLKYKALX (SEQ ID NO:32), XXXXXLSALTPSPSWLKYKALXX (SEQ ID NO:33), XXXXXLSALTPSPSWLKYKALXXX(SEQ ID NO:34), XXXXXLSALTPSPSWLKYKALXXXX (SEQ ID NO.35), or XXXXXLSALTPSPSWLKYKALXXXXX (SEQ ID NO:36), where X is any naturally-occurring amino acid or where X is an unconventional amino acid or amino acid analog as described herein and known to those of skill in the art.

B. GFE Peptides

The tripeptide GFE motif is associated with DPEP-1 binding. GFE-1 is a 13 amino acid peptide that binds DPEP-1 has been suggested for use as a lung-targeting peptide for drug delivery (Rajotte, D., et al., J. Biol Chem. 274(17): 11593-11598 (1999); U.S. Pat. No. 6,784,153). Specific peptides having this tripeptide "GFE" motive have been identified as having DPEP-1 binding activity in lung microvasculature including GFE-1: CGFECVRQCPERC (SEQ ID NO:2) and GFE-2: CGFELETC (SEQ ID NO.3)

Notably, the use of these peptides was reported only for homing to lung and kidney and therapeutic use of these peptides was not contemplated by Rajotte et al unless conjugated with additional therapeutic agents.

C. Modified Peptides and Peptide Analogs

In various embodiments, the peptide comprises amino acids, including carboxy- and/or amino-terminal amino acids in peptides, or can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4(R)-methyl-N-methylthreonine (MeBmt), N-methyl-leucine (MeLeu), aminoisobutyric acid, statine, and N-methyl-alanine (MeAla). Amino acids may participate in a disulfide bond. In certain embodiments, the amino acid has the general structure $H_2N$—C(H)(R)—COOH. In certain embodiments, the amino acid is a naturally-occurring amino acid. In certain embodiments, the amino acid is a synthetic or un-natural amino acid (e.g., a,a-disubstituted amino acids, N-alkyl amino acids); in some embodiments, the amino acid is a d-amino acid, in certain embodiments, the amino acid is an 1-amino acid.

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., Current Protocols in Molecular Biology, Wiley Interscience, New York, 2001; and Sambrook et al., Molecular Cloning: A Laboratory Manual, 3rd edition, Cold Spring Harbor Laboratory Press, N.Y., 2001.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., Pharm. Res. 10:1268-1273 (1993)). In light of this, it is often advantageous to use modified versions of peptides. The modified peptides retain the structural characteristics of the original L-amino acid peptides that confer the desired biological activity of LSALT but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides Thus, a peptide derivative or peptidomimetic of the present invention may be all L, all D or mixed D. L peptide, in either forward or reverse order. The presence of an N-terminal or C-terminal D-amino acid increases the in vivo stability of a peptide since peptidases cannot utilize a D-amino acid as a substrate (Powell et al., Pharm. Res. 10:1268-1273 (1993). Reverse-D peptides are peptides containing D-amino acids, arranged in a reverse sequence relative to a peptide containing L-amino acids Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, Nature 368:692-693 (1994), Jameson et al., Nature 368:744-746 (1994)) Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

In one embodiment, the peptide is chemically modified to confer resistance to peptidases acting on the N-terminal or C-terminal residues of a peptide by adding chemical groups at the peptide termini, such that the modified peptide is no longer a substrate for the peptidase. In one embodiment, one such chemical modification is glycosylation of the peptides at either or both termini. In other embodiments, chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

In one embodiment, substitution of certain naturally-occurring amino acids for non-naturally amino acids in the peptides confers resistance to proteolysis. Such a substitution can, for instance, confer resistance to proteolysis by exopeptidases acting on the N-terminus without affecting biological activity. Examples of non-naturally-occurring amino acids include a,a-disubstituted amino acids, N-alkyl amino acids, C-a-methyl amino acids, P-amino acids, and P-methyl amino acids. Amino acids analogs useful in the present invention may include, but are not limited to, P-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is known in the art.

Peptide analogs are commonly used in the pharmaceutical industry as non-peptide drugs with properties analogous to those of the template peptide. The non-peptide compounds are termed "peptide mimetics" or peptidomimetics (Fauchere et al., Infect. Immun. 54:283-287 (1986); Evans et al., J. Med. Chem. 30-1229-1239 (1987)) Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as $—CH_2NH—$, $—CH_2S—$, $—CH_2—$, $—CH{=}CH—$ (cis and trans), $—CH_2SO—$, $—CH(OH)CH_2—$, $—COCH_2—$ etc., by methods well known in the art (Spatola, Peptide Backbone Modifications, Vega Data, 1(3):267 (1983); Spatola et al. Life Sci. 38:1243-1249 (1986); Hudson et al Int J. Pept. Res. 14:177-185 (1979); and Weinstein. B., 1983, Chemistry and Biochemistry, of Amino Acids, Peptides and Proteins, Weinstein eds, Marcel Dekker, New-York.). Such peptide mimetics may have significant advantages over naturally-occurring polypeptides including more economical production, greater chemical stability, enhanced pharmacological properties (e.g., halflife, absorption, potency, efficiency, etc.), reduced antigenicity and others.

Pharmaceutically acceptable salts retain the desired biological activity of the parent peptide without toxic side effects.

D. Antibodies to DPEP-1

In one embodiment, a DPEP-1 binding agent is an antibody that selectively binds to DPEP-1. In one embodiment, the antibody is a blocking antibody that prevents binding of the leukocytes to the DPEP-1 molecule expressed on the endothelium. As used herein, an antibody that "selectively reacts with DPEP-1" binds with substantially higher affinity to membrane dipeptidase than to an unrelated polypeptide such as another zine metalloprotease. The term "antibody" is used herein in its broadest sense to include polyclonal and monoclonal antibodies, as well as polypeptide fragments of antibodies that retain a selective affinity for membrane dipeptidase of at least about $1\times10_5$ $M^{-1}$. Antibody fragments such as Fab, F(ab')2 and Fy fragments can selectively react with membrane dipeptidase and, therefore, are included within the meaning of the term antibody as defined herein. The term antibody as used herein includes naturally occurring antibodies, as well as non-naturally occurring antibodies and fragments such as chimeric antibodies and humanized antibodies that are selectively reactive with membrane dipeptidase.

Methods for producing antibodies are routine in the art. Dipeptidase, which can be prepared from natural sources or produced recombinantly as described above, or a fragment thereof, such as a synthetic peptide, can be used as an immunogen. Non-immunogenic fragments or synthetic peptides can be made immunogenic by coupling the hapten to a carrier molecule such as bovine serum albumin (BSA) or keyhole limpet hemocyanin (KLH). In addition, various other carrier molecules and methods for coupling a bapten to a carrier molecule are well known in the art as described, for example, by Harlow and Lane, Antibodies: A Laboratory Manual (Cold Spring Harbor Laboratory Press, 1988), which is incorporated herein by reference Antibodies, including non-naturally occurring antibodies such as, chimeric and humanized antibodies, also can be constructed using solid phase peptide synthesis, produced recombinantly or obtained, for example, by screening combinatorial libraries consisting of variable heavy chains and variable light chains as described by Borrebaeck (Ed.), Antibody Engineering (Second edition) New York: Oxford University Press (1995), which is incorporated herein by reference.

In one embodiment, the antibody binds the cysteine residues at position Cys-361 of DPEP-1 to prevent dimerization of DPEP-1 monomers (Keynon, S., et al., Biochem, 35(38): 12511-12517 (1996)).

In one embodiment, the antibody binds to the catalytic site of DPEP-1 at positions His219, Glu125, His152, His20 or His198 (Keynon, S., et al., Biochem J., 326(1):47-51 (1997).

In one embodiment, the antibody binds to the dipeptide binding site of DPEP-1.

In one embodiment, the antibody binds to the dipeptide-sensing site of DPEP-1.

In one embodiment, the antibody binds to the leukocyte adhesion site of DPEP-1

E. Small Molecule Compounds

In another embodiment, the DPEP-1 antagonist compound is a small molecule compound. Such compounds are identified by screening combinatorial libraries of synthetic small molecule compounds, determining which compound (s) have the highest probability of providing an effective therapeutic and then optimizing the therapeutic properties of the identified small molecule compound(s) by synthesizing structurally related analogs and analyzing them for binding to the target molecule (Gallop et al., J. Med. Chem. 37:1233-1251 (1994), Gordon et al., J Med. Chem. 37:1385-1401 (1994), Czarnik and Ellman, Acc. Chem. Res. 29:112-170 (1996), Thompson and Ellman, Chem. Rev. 96:555-600 (1996) and Balkenhohl et al., Angew. Chem. Int. Ed. 35:2288-2337 (1996)).

Another recently reported approach for identifying high affinity ligands for molecular targets of interest is by determining structure-activity relationships from nuclear magnetic resonance analysis, i.e., "SAR by NMR" (Shuker et al., Science 274.1531-1534 (1996) and U.S. Pat. No. 5,698,401 by Fesik et al.). In this approach, the physical structure of a target protein is determined by NMR and then small molecule building blocks are identified that bind to the protein at nearby points on the protein surface. Adjacently binding small molecules are then coupled together with a linker in order to obtain compounds that bind to the target protein with higher affinity than the unlinked compounds alone. Thus, by having available the NMR structure of the target protein, the lengths of linkers for coupling two adjacently binding small molecules can be determined and small molecule ligands can be rationally designed.

Other methods such as those described in U.S. Pat. No. 6,344,330, provide a molecular approach for rapidly and efficiently identifying small molecule ligands that are capable of binding to a biomolecular target with high affinity, wherein ligand compounds identified by the subject method may find use, for example, as new small molecule drug leads. This methods allow a population of only the most favorable compounds to be assayed for binding to a target biomolecule without the need for screening all possible small molecule compounds and combinations thereof for binding to the target as is required in standard combinatorial library approaches.

In one embodiment, the small molecule binds the cysteine residues at position Cys-361 of DPEP-1 to prevent dimerization of DPEP-1 monomers (Keynon, S., et al., Biochem, 35(38): 12511-12517 (1996)).

In one embodiment, the antibody binds to the catalytic site of DPEP-1 at positions His219, Glu125, His152, His20 or His198 (Keynon, S., et al., Biochem J., 326(1):47-51 (1997).

In one embodiment, the small molecule binds to the dipeptide binding site of DPEP-1.

In one embodiment, the small molecule binds to the dipeptide-sensing site of DPEP-1.

In one embodiment, the small molecule binds to the leukocyte adhesion site of DPEP-1

In one embodiment, the small molecule is cilastatin ((Z)-7-[(2R)-2-Amino-3-hydroxy-3-oxopropyl]sulfanyl-2-{[(1S)-2,2-dimethylcyclopropanecarbonyl]amino}hept-2-enoic acid) (CAS Registry #82009-34-5). Cilastatin is commonly prescribed with imipenem to inhibit the dipeptidase enzyme that degrades the imipenem antibiotic in order to prolong the antibiotic half-life. Cilastatin/imipenem has been suggested to cause mucosal inflammation as a side effect. This is contrary to the anti-inflammatory actions on leukocyte recruitment by blocking DPEP-1 described and exemplified herein.

In one embodiment, the small molecule is a cilastatin derivative.

In certain embodiments, the small molecule is an aminophosphinic acid derivative. Examples of these aminophosphinic acid derivatives are known in the art (See Gurulingappa, H. et al., Bioorganic & Medicinal Chemistry Letters 14 (2004) 3531-3533, 2004; U.S. Pat. Nos. 7,785,564 and 6,927,212 the contents of which are hereby incorporated by reference).

In one embodiment, the aminophosphinic acid derivative has the formula:

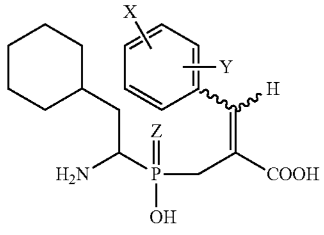

E & Z-isomers wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR'. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O) or S. X and Y can also be an amine selected from $NH_2$, N(C1 to C6 alkyl)$_2$, and NH(C1 to C6 alkyl). The benzene ring may reside on the same or the opposite side of the double bond from the carboxylic acid group. Either isomer is active in the methods described herein.

In specific embodiments, the aminophosphinic acid compound is selected from a compound having the formula:

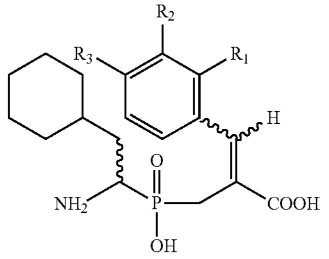

where R1 is H, R2 is H and R3 is F; R1 is H, R2 is H and R3 is Br; or R1 is H, R2 is H and R3 is I, in Z or E configuration.

IV. Pharmaceutical Formulations and Medicaments

I. In another aspect, the compounds or agents described herein, as well as variants and modifications thereof, are provided as a pharmaceutical composition for therapeutic use. In one embodiment, the pharmaceutical formulation comprises an isolated peptide containing the sequence LSALTPSPSWLKYKAL, and designated herein "LSALT". In another embodiment, the pharmaceutical formulation comprises an isolated peptide contained as an insert in a phage virus, and/or may further comprise 1, 2, 3, 4, 5 additional amino acid residues at the N-terminus and/or C-terminus of the LSALTPSPSWLKYKAL (SEQ ID NO:1) sequence.

In one embodiment, the pharmaceutical formulation comprises an isolated peptide designated herein "GFE-1". In another embodiment, the pharmaceutical formulation comprises an isolated peptide contained as an insert in a phage virus, and/or may further comprise 1, 2, 3, 4, 5 additional amino acid residues at the N-terminus and/or C-terminus of the LSALTPSPSWLKYKAL (SEQ ID NO.1) sequence.

In one embodiment, the pharmaceutical formulation comprises an isolated peptide designated herein "GFE-2". In another embodiment, the pharmaceutical formulation comprises an isolated peptide contained as an insert in a phage virus, and/or may further comprise 1, 2, 3, 4, 5 additional amino acid residues at the N-terminus and/or C-terminus of the LSALTPSPSWLKYKAL (SEQ ID NO.1) sequence.

Representative delivery regimens include oral, parenteral (including subcutaneous, intramuscular and intravenous injection), rectal, buccal (including sublingual), transdermal, inhalation ocular and intranasal. In one embodiment, delivery of compounds entails subcutaneous injection of a controlled-release injectable formulation. In some embodiments, compounds described herein are useful for subcutaneous, intranasal and inhalation administration.

The selection of the exact dose and composition and the most appropriate delivery regimen will be influenced by, inter alia, the pharmacological properties of the selected peptide, the nature and severity of the condition being treated, and the physical condition and mental acuity of the recipient. Additionally, the route of administration will result in differential amounts of absorbed material. Bioavailabilities for administration of compounds through different routes are particularly variable, with amounts from less than 1% to near 100% being seen. Typically, bioavailability from routes other than intravenous, intraperitoneal or subcutaneous injection are 50% or less.

The pharmaceutical compositions or formulations of the present invention can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include, but are not limited to, water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, the pharmaceutical composition comprise a liquid carrier such as, but not limited to, water, saline, phosphate buffered saline, Ringer's solution, dextrose solution, serum-containing solutions, Hank's solution, other aqueous physiologically balanced solutions, oils, esters and glycols.

The compounds as described herein can be formulated as neutral or salt forms. As stated above, pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The pharmaceutical formulations of the present invention contain, as the active ingredient, an binding agent, which may be mixed with an excipient, diluted by an excipient or enclosed within a carrier, which can be in the form of a capsule, sachet, paper or other container, according to well-known methods and pharmaceutical compositions. The composition may be administered by any route suitable for peptide administration, including parenteral, intravenous, subcutaneous, or intramuscular administration. Typically, the peptide is dissolved or suspended in a sterile injectable solution, at a concentration sufficient to provide the required dose in 0.5 to 2 ml or less. Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable materials can be sterilized for example, by filtration through a bacterial-retaining filter.

The pharmaceutical compositions may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

V. Methods of Treatment

Methods of treatment are contemplated for diseases and conditions associated with inflammation including particularly diseases and conditions where inflammation is caused by ischemia/reperfusion injury to a tissue or organ. Ischemia followed by reperfusion in an organ produces structural and functional abnormalities in the tissue of that organ and others. Neutrophil infiltration, hemorrhage, edema and necrosis are all observed in tissues following an ischemia/reperfusion injury. The DPEP-1 target represents a previously undescribed pathway for inflammation which opens up the opportunity for dipeptidase inhibitors such as those described herein to be used to treat or prevent diseases and conditions mediated by inflammation.

A non-limiting list of common diseases and medical problems that are directly associated with inflammation include: arthritis, kidney failure, lupus, asthma, psoriasis, pancreatitis, allergy, fibrosis, surgical complications, anemia, and fibromyalgia. Other diseases associated with chronic inflammation include cancer, which is caused by chronic inflammation, heart attack where chronic inflammation contributes to coronary atherosclerosis; Alzheimer's disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis. Parkinson's disease, infection, inflammatory bowel disease including Crohn's disease and ulcerative colitis as well as multiple sclerosis.

In particular embodiments, the methods described herein are useful for protecting tissues and organs from damage associated with conditions such as, but not limited to sepsis-induced injury, acute organ injury (for example acute kidney injury in the setting of low blood pressure).

In other embodiments, the methods described herein are useful for protecting tissues and organs from damage associated with sepsis-induced conditions such as respiratory distress syndrome, encephalopathy, sepsis-induced liver failure, sepsis-induced kidney failure or sepsis-induced heart failure.

In other embodiments, the methods described herein are useful for protecting tissues and organs from damage associated with ischemia-reperfusion injury such as, but not limited to peri-operative procedures, heart failure, liver failure, stroke, myocardial infarct, shock liver, spinal cord injury, brain injury, and the like. These compositions can also be used to prevent or treat ischemia-reperfusion injury in high risk patients.

In other embodiments, the methods are also useful prior to angioplasty or thrombolytic therapy, or after transplantation or reperfusion of an ischemic organ following surgery, angioplasty or thrombolytic therapy.

Other examples of surgical procedures and organs at risk of ischemia reperfusion injury during these procedures include, but are not limited, brain injury during carotid artery surgery, cerebral vascular surgery and surgery of the heart and aorta; brain, spinal cord, intestine and kidney injury; lung injury following thromboembolectomy or the use of cardiopulmonary bypass during lung and heart surgery; heart injury following revascularization (coronary artery bypass graft surgery), intestinal injury following surgery on the mesenteric arteries; and skin injury following harvesting of a skin graft.

Additional surgical procedures for which this method is useful include harvesting donor organs for transplantation. In other embodiments, the methods are also useful for the protection of allograft organs during donor procurement, ex vivo handling and implantation into a transplant recipient. Compositions of the present invention can be administered prior to, during or following harvesting a donor organ which will be transplanted, prior to or during a surgical procedure in which ischemia is expected.

Hence, the invention relates to a method for preventing, limiting, or treating ischemia reperfusion injury in a subject, comprising the steps of identifying a subject that has undergone an ischemic event, or in which an ischemic event is imminent or is at risk for having an ischemic event and administering a therapeutically effective or prophylactically effective amount of the compositions described herein.

While not to be bound by any particular mechanism, the protective effects of the compositions provided herein are mediated through binding at the DPEP-1 target and a direct reduction in DPEP-1-regulated leukocyte recruitment, inflammation and tumor cell adhesion. These effects described herein on inflammation-mediated disease and tumor metastasis occur independent of DPEP-1 dipeptidase activity or its role in regulating tubular transport Previous studies have required combination of a DPEP-1 antagonists to prolong the half-life of an antibiotic compound to treat bacterial infection. Other studies have used a DPEP-1 antagonist cilastatin to prevent or treat organ damage by preventing the renal tubular uptake of chemotherapeutic agents, or other nephrotoxic agents (Humanes et al., Kidney Intl, 82:652-553 (2012); Koller et al., Biochem Biophys Res Comm 131(2):974-979 (1985)). The direct treatment of DPEP-1 regulated inflammation, inflammation-mediated disease or tumor metastasis by using DPEP-1 antagonists has not previously been identified.

As such, in certain embodiments, the compositions described herein are not used to treat or reduce tissue damage induced directly by toxic compounds such as nephrotoxic compounds, or chemotherapeutic agents. In other embodiments, the compositions described herein are not administered in combination with beta-lactam antibiotic compounds. In other embodiments, the compositions described herein are not administered in combination with carbapenem antibiotic compounds.

The invention provides a method to reduce or modulate inflammation comprising administering an effective amount of a compound that binds to DPEP-1 to reduce or modulate inflammation.

In one embodiment, inflammation is characterized by a profile of inflammatory markers selected from IL-12, IP-10, IL-1B, IL-5, GM-CSF, IFN Gamma, or IL-1a.

In one embodiment, the composition comprises a peptide, blocking antibody or a small molecule compound.

In one embodiment, the composition comprises cilastatin, a derivative thereof, or a pharmaceutically acceptable salt thereof.

In certain embodiments, the composition comprises an aminophosphinic acid derivative.

In one embodiment, the aminophosphinic acid derivative has the formula:

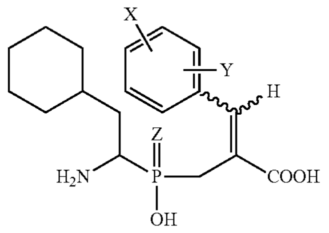

E & Z-isoiuers wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR'. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O or S. X and Y can also be an amine selected from $NH_2$, N(C1 to C6 alkyl)$_2$, and NH(C1 to C6 alkyl). The benzene ring may reside on the same or the opposite side of the double bond from the carboxylic acid group. Either isomer is active in the methods described herein.

In one embodiment, the inflammation is associated with an inflammatory disorder is selected from the group consisting of gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyperresponsiveness, vasculitis, septic shock, inflammatory skin disorders, psoriasis, atopic dermatitis, and eczema.

The invention provides a method to block leukocyte recruitment of a subject comprising administering an effective amount of a composition that binds to DPEP-1 to block leukocyte recruitment.

In one embodiment, the composition comprises a peptide, blocking antibody or a small molecule compound.

In one embodiment, the composition comprises cilastatin, a derivative thereof, or a pharmaceutically acceptable salt thereof.

In certain embodiments, the composition comprises an aminophosphinic acid derivative.

In one embodiment, the aminophosphinic acid derivative has the formula:

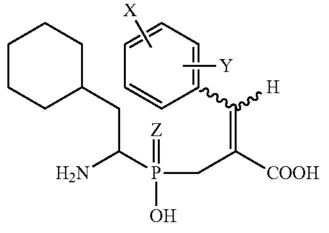

E & Z-isoiners wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR' Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O or S. X and Y can also be an amine selected from $NH_2$, N(C1 to C6 alkyl)$_2$, and NH(C1 to C6 alkyl). The benzene ring may reside on the same or the opposite side of the double bond from the carboxylic acid group. Either isomer is active in the methods described herein.

In one embodiment, the method further comprises identifying a subject in need of treatment by diagnostic test for needing reduction in inflammation. Indications for treatment include, but are not limited to, clinical signs and symptoms in any patient that is at risk for acute kidney injury (preoperatively or before administering intravenous contrast) or in any patient having decreasing urine output or increasing serum creatinine, such as in a patient with a systemic infection or low blood pressure.

The invention provides a method for reducing or preventing tumor metastasis in a subject comprising administering an effective amount of a composition that binds to DPEP-1 thereby reducing or preventing tumor metastasis. In one embodiment, DPEP-1 can acts as an adhesion molecule for leukocytes on tumor cells independent of its enzymatic activity and binding DPEP-1 by a selective DPEP-1 binding agent described herein may reduce or prevent tumor metastasis. In another embodiment, DPEP-1 contributes to inflammation which promotes tumor metastasis and binding of DPEP-1 by selective DPEP-1 binding agents reduces or prevents tumor metastasis.

In certain embodiments, the tumor is selected from those tumors known to cause cancer that have the potential to, or are presently capable of metastasis. For example, the cancer can be pancreatic cancer, kidney cancer, e.g., renal cell carcinoma (RCC), urogenital cancer, e g., urothelial carcinomas in urinary bladder, kidney, pelvic and ureter, melanoma, prostate carcinoma, lung carcinomas (non-small cell carcinoma, small cell carcinoma, neuroendocrine carcinoma and carcinoid tumor), breast carcinomas (ductal carcinoma, lobular carcinoma and mixed ductal and lobular carcinoma), thyroid carcinomas (papillary thyroid carcinoma, follicular carcinoma and medullary carcinoma), brain cancers (meningioma, astrocytoma, glioblastoma, cerebellum tumors, medulloblastoma, ependymoma), ovarian carcinomas (serous, mucinous and endometrioid types), cervical cancers (squamous cell carcinoma in situ, invasive squamous cell carcinoma and endocervical adenocarcinoma), uterine endometrial carcinoma (endometrioid, serous and mucinous types), primary peritoneal carcinoma, mesothelioma (pleura and peritoneum), eye cancer (retinoblastoma), muscle (rhapdosarcoma and leiomyosarcoma), lymphomas, esophageal cancer (adenocarcinoma and squamous cell carcinoma), gastric cancers (gastric adenocarcinoma and gastrointestinal stroma tumor), liver cancers (hepatocellular carcinoma and bile duct cancer), small intestinal tumors (small intestinal stromal tumor and carcinoid tumor) colon cancer (adenocarcinoma of the colon, colon high grade dysplasia and colon carcinoid tumor), testicular cancer, skin cancers (melanoma and squamous cell carcinoma) and adrenal carcinoma.

In one embodiment, the composition comprises a peptide, blocking antibody or a small molecule compound.

In one embodiment, the composition comprises cilastatin, a derivative thereof, or a pharmaceutically acceptable salt thereof.

In certain embodiments, the composition comprises an aminophosphinic acid derivative.

In one embodiment, the aminophosphinic acid derivative has the formula:

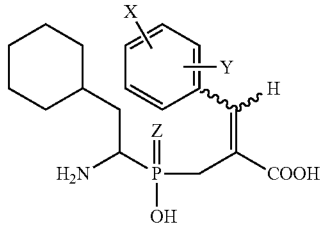

E & Z-isomers wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR'. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O or S. X and Y can also be an amine selected from $NH_2$. N(C1 to C6 alkyl)$_2$, and NH(C1 to C6 alkyl). The benzene ring may reside on the same or the opposite side of the double bond from the carboxylic acid group. Either isomer is active in the methods described herein.

In one embodiment, the method further comprises identifying a subject in need of treatment through diagnostic test to determine a need for reduction or prevention of tumor metastasis by determining the presence of a DPEP-1-binding molecule on a tumor of a patient.

The invention provides a method for reducing or preventing leukocyte recruitment and inflammation during sepsis in a subject comprising administering an effective amount of a composition that binds to DPEP-1 thereby reducing or preventing the organ complications of sepsis.

In one embodiment, the composition comprises a peptide, blocking antibody or a small molecule compound.

In one embodiment, the composition comprises cilastatin, a derivative thereof, or a pharmaceutically acceptable salt thereof.

In certain embodiments, the composition comprises an aminophosphinic acid derivative.

In one embodiment, the aminophosphinic acid derivative has the formula:

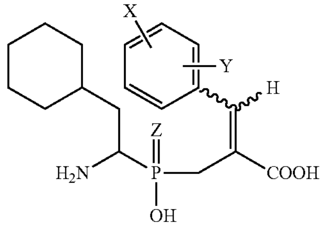

E & Z-isomers wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR'. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O or S. X and Y can also be an amine selected from $NH_2$. N(C1 to C6 alkyl)$_2$, and NH(C1 to C6 alkyl). The benzene ring may reside on the same or the opposite side of the double bond from the carboxylic acid group. Either isomer is active in the methods described herein.

In one embodiment, the method further comprises identifying a subject in need of treatment through diagnostic test to determine a need for reduction or prevention of ischemiareperfusion injury Indications for treatment include, but are not limited to, clinical signs and symptoms of ischemia-reperfusion injury or undergoing a surgical procedure with a high risk of ischemia-reperfusion injury.

The invention includes a method of treating a symptom of ischemia-reperfusion injury in a patient comprising administering to the patient a pharmaceutically effective amount of a composition comprising an antagonist compound of DPEP-1.

In one embodiment, the composition is administered until symptoms of ischemiareperfusion injury are reduced or ameliorated.

In one embodiment, the isolated peptide or variant thereof is administered at a dosage is between about 0.01 mg/kg to 100 mg/kg.

The invention provides a method for reducing or preventing ischemia-reperfusion injury related disorders in a subject comprising administering an effective amount of a composition that binds to DPEP-1 thereby reducing or preventing ischemia-reperfusion injury. In one embodiment, the method reduces or prevents the leukocyte recruitment and inflammation that is associated with ischemia-reperfusion injury.

In one embodiment, the composition comprises a peptide, blocking antibody or a small molecule compound.

In one embodiment, the composition comprises cilastatin, a derivative thereof, or a pharmaceutically acceptable salt thereof.

In certain embodiments, the composition comprises an aminophosphinic acid derivative.

In one embodiment, the aminophosphinic acid derivative has the formula:

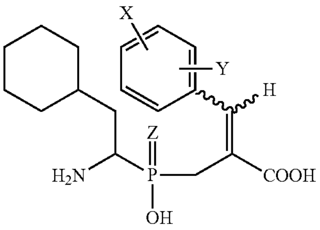

E & Z-isomers wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR'. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O or S. X and Y can also be an amine selected from $NH_2$, N(C1 to C6 alkyl)$_2$, and NH(C1 to C6 alkyl). The benzene ring may reside on the same or the opposite side of the double bond from the carboxylic acid group. Either isomer is active in the methods described herein.

In one embodiment, the ischemia-reperfusion injury related disorder is associated with ischemic and post-ischemic events in organs and tissues, and the disorder is selected from a group consisting of thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure (including heart failure, liver failure, kidney failure and the like); restenosis; atherosclerosis; thrombosis; platelet aggregation; shock liver; spinal cord injury; brain injury or following conditions selected from a list comprising of procedures such as peri-operative procedures, cardiac surgery; organ surgery; organ transplantation; angiography, cardiopulmonary and cerebral resuscitation.

In one embodiment, the ischemia-reperfusion injury is associated with harvesting donor organs for transplantation.

In one embodiment, the ischemia-reperfusion injury occurs to allograft organs during donor procurement, ex vivo handling or implantation into a transplant recipient.

In various embodiments, the compositions can be administered (i) prior to, during or following harvesting a donor organ which will be transplanted or (ii) prior to or during a surgical procedure in which ischemia is expected.

The invention provides a method for reducing or preventing acute kidney injury in a subject comprising administering an effective amount of a composition that binds to DPEP-1 thereby reducing or preventing acute kidney injury. In one embodiment, the method reduces or prevents the leukocyte recruitment and inflammation that is associated with acute kidney injury.

In one embodiment, the composition comprises a peptide, blocking antibody or a small molecule compound.

In one embodiment, the composition comprises cilastatin, a derivative thereof, or a pharmaceutically acceptable salt thereof.

In certain embodiments, the composition comprises an aminophosphinic acid derivative.

In one embodiment, the aminophosphinic acid derivative has the formula:

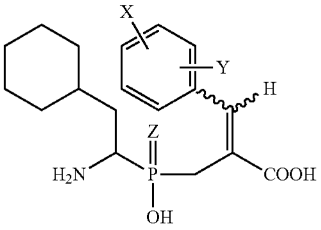

E & Z-isomers wherein X is selected from the group consisting of any halogen or C1 to C6 haloalkyl or C1 to C6 di- or trihaloalkyl or C1 to C6 alkyl, $CF_3$ NR', or F, Cl, Br, $I^{125}$, I, $CF_3$ NR'. Y is selected from the group consisting of any halogen, H, $CH_3$, $OCH_3$, NR' or C1 to C6 haloalkyl, or C1 to C6 alkoxy group or C1 to C6 di- or trihaloalkyl or C1 to C6 alkyl; NR' is selected from $NH_2$, N(C1 to C6 alkyl)$_2$, and NH(C1 to C6 alkyl); Z can be either O or S. X and Y can also be an amine selected from $NH_2$, N(C1 to C6 alkyl)$_2$, and NH(C1 to C6 alkyl). The benzene ring may reside on the same or the opposite side of the double bond from the carboxylic acid group. Either isomer is active in the methods described herein.

In one embodiment, the method comprises identifying a subject in need of treatment through diagnostic test to determine a need for reduction or prevention of acute kidney injury.

In one embodiment, the acute kidney injury is a result of sepsis.

In one embodiment, the acute kidney injury is a result of ischemia reperfusion.

In one embodiment, the acute kidney injury is toxin-induced kidney injury.

In one embodiment, the acute kidney injury is contrast-induced kidney injury.

VI. Routes of Administration

A DPEP-1 binding agent as described herein (or a composition or medicament containing DPEP-1 binding agent as described herein) may be administered by any appropriate route. In some embodiments, the DPEP-1 binding agent is administered parenterally. In some embodiments, the parenteral administration is selected from intravenous, intradermal, inhalation, transdermal (topical), intraocular, intramuscular, subcutaneous, intramuscular, and/or transmucosal administration. In some embodiments, an DPEP-1 binding agent as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, a DPEP-1 binding agent as described herein is administered intravenously. In other embodiments, a DPEP-1 binding agent as described herein is administered by direct administration to a target tissue, such as heart or muscle (e.g., intramuscular), tumor (intratumorally), nervous system (e g., direct injection into the brain; intraventricularly; intrathecally). Alternatively, a DPEP-1 binding agent as described herein (or a composition or medicament containing a DPEP-1 binding agent as described herein) can be administered by inhalation, parenterally, intradermally, transdermally, or transmucosally (e.g., orally or nasally). More than one route can be used concurrently, if desired.

In some embodiments, a DPEP-1 binding agent as described herein is administered orally. In some embodiments, the present invention provides solid dosage forms of DPEP-1 binding agents as described herein for oral administration including (a) a DPEP-1 binding agent, (b) at least one pharmaceutically acceptable pH-lowering agent, (c) at least one absorption enhancer effective to promote bioavailability of the DPEP-1 binding agent, and (d) a protective vehicle. In some embodiments, the solid dosage form is a capsule or tablet.

VII. Dosing

An effective quantity of the compound of interest is employed in treatment. The dosage of compounds used in accordance with the invention varies depending on the compound and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

Various embodiments may include differing dosing regimen. In some embodiments, the DPEP-1 binding agent is administered via continuous infusion. In some embodiments, the continuous infusion is intravenous. In other embodiments, the continuous infusion is subcutaneous. Alternatively or additionally, in some embodiments, the DPEP-1 binding agent is administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

In one embodiment, the local dosage is administered at least once a day until a therapeutic result is achieved. The dosage can be administered twice a day, but more or less frequent dosing can be recommended by the clinician. Once a therapeutic result is achieved, the compound can be tapered or discontinued. Occasionally, side effects warrant discontinuation of therapy. An effective quantity of the compound of interest is employed in treatment. The dosage of compounds used in accordance with the invention varies depending on the compound and the condition being treated. The age, lean body weight, total weight, body surface area, and clinical condition of the recipient patient, and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

When employed as pharmaceuticals, the compounds of the present invention are administered in the form of pharmaceutical compositions and these pharmaceutical compositions represent further embodiments of the present invention. These compounds can be administered by a variety of routes including oral, rectal, transdermal, subcutaneous, intravenous, intramuscular, and intranasal, or via intratracheal instillation or aerosol inhalation.

The compounds of the invention are useful in reducing inflammation or modifying the inflammatory profile of a tissue, e g., into the liver manner of administration will be defined by the application of the compound and can be determined by routine methods of clinical testing to find the optimum dose.

In one embodiment, the dosage is between about 0.01 mg/kg to about 100 mg/kg of active peptide, between about 0.01 mg/kg to about 50 mg/kg, or between about 0.01 mg/kg to about 25 mg/kg.

In other embodiments, the dosage is between about 0.1 mg/kg to about 100 mg/kg, between about 0.1 mg/kg to about 50 mg/kg, between about 0.1 mg/kg to about 25 mg/kg, or between about 0.1 mg/kg to about 10 mg/kg.

In other embodiments, the dosage is between about 0.5 mg/kg to about 100 mg/kg, about 0.5 mg/kg to about 50 mg/kg, about 0.5 mg/kg to about 25 mg/kg, or about 0.5 mg/kg to about 10.0 mg/kg.

In other embodiments, the dosage is between about 1.0 mg/kg to about 25 mg/kg, between about 1.0 mg/kg to about 50 mg/kg, between about 1.0 mg/kg to about 70 mg/kg, between about 1.0 mg/kg to about 100 mg/kg, between about 5.0 mg/kg to about 25 mg/kg, between about 5.0 mg/kg to about 50 mg/kg, between about 5.0 mg/kg to about 70 mg/kg, between about 5.0 mg/kg to about 100 mg/kg, between about 10.0 mg/kg to about 25 mg/kg, between about 10.0 mg/kg to about 50 mg/kg, between about 10.0 mg/kg to about 70 mg/kg, or between about 10.0 mg/kg to about 100 mg/kg.

In another embodiment, the dosage is between about 50 gM and about 500 gM.

It will be understood, however, that the amount of the DPEP-1 binding agent actually administered will be determined by a physician, in the light of the relevant circumstances, including the condition to be treated, the chosen route of administration, the actual compound administered, the age, weight, and response of the individual patient, the severity of the patient's symptoms, and the like.

In various embodiments, compounds described herein, or salts thereof, are administered in amounts between about 0.001 and about 20 mg/kg body weight per day, between about 0.01 and about 10 mg/kg body weight per day, between about 0.1 and about 1000 gg/kg body weight per day, or between about 0.1 to about 100 gg/kg body weight per day. Routes of administration vary. For example, compounds described herein, or salts thereof, are administered in amounts between about 0.1 and about 1000 gg/kg body weight per day, or between about 0.1 to about 100 gg/kg body weight per day, by subcutaneous injection. By way of example, for a 50 kg human female subject, the daily dose of active ingredient is from about 5 to about 5000 gg, or from about 5 to about 5000 pg by subcutaneous injection. Different doses will be needed, depending on the route of administration, the compound potency, the pharmacokinetic profile and the applicable bioavailability observed, and the active agent and the disease being treated. In an alternate embodiment where the administration is by inhalation, the daily dose is from 1000 to about 20,000 pg, twice daily. In other mammals, such as horses, dogs, and cattle, higher doses may be required. This dosage may be delivered in a conventional pharmaceutical composition by a single administration, by multiple applications, or via controlled release, as needed to achieve the most effective results.

VIII. Kits

In some embodiments, the present invention further provides kits or other articles of manufacture which contain a DPEP-1 binding agent or pharmaceutical compositions described herein, as well as instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, the container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, the container may contain a single dose of a stable formulation containing a DPEP-1 binding agent. In various embodiments, a single dose of the stable formulation is present in a volume of less than about 15 ml, about 10 ml, about 5.0 ml, about 4.0 ml, about 3.5 ml, about 3.0 ml, about 2.5 ml, about 2.0 ml, about 1.5 ml, about 1.0 ml, or about 0.5 ml. Alternatively, the container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least about 1 mg/ml (e g., at least about 5 mg/ml, at least about 10 mg/ml, at least about 20 mg/ml, at least about 30 mg/ml, at least about 40 mg/ml, at least about 50 mg/ml, at least about 75 mg/ml, at least about 100 mg/ml) Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

IX. Screening Methods

In accordance with one aspect of the invention, the invention provides a method for screening for compounds that bind to DPEP-1.

In one embodiment, the screening method comprises a competitive binding assay using an LSALT or GFE peptide.

In one embodiment, the screening method comprises identifying a compound effective to decrease inflammation in a tissue of a patient comprising: (a) screening a library of test compounds for their ability to bind to DPEP-1 in the tissue; (b) selecting candidate test compounds that show selective binding affinity; (c) testing the candidate compounds for inflammation reducing activity, and (d) selecting a candidate compound if it decrease inflammation, thereby providing a compound effective to decrease inflammation.

For those library compounds that show a selective binding affinity to one of the target peptides in the library, e.g., at least a 10-100 fold increase in binding affinity over a random sequence peptide, the compound is further testing for its ability to reduce inflammation in a tissue, according to methods detailed below. Test compounds that are shown to reduce inflammation in a tissue are then identified as lead compounds for further compound testing and development.

In one embodiment, the tissue is lung tissue or liver tissue.

In one embodiment, a method is provided for identifying a compound effective to block leukocyte recruitment in the vasculature of a patient.

In one embodiment, the invention provides a method of identifying a compound effective to reduce inflammation in a tissue of a patient comprising: (a) screening a library of test compounds for their ability to bind to DPEP-1; (b) selecting compounds that show selective binding affinity, (c) testing the compounds for leukocyte recruitment inhibiting activity, and (d) selecting a compound if it reduces inflammation in a tissue.

In one embodiment, the tissue is lung tissue or liver tissue.

In one embodiment, the method further comprises the steps of (e) further testing the compound for its ability to block leukocyte recruitment in an animal bearing a solid tumor; and (f) selecting the compound if it block leukocyte recruitment in step (e).

In one embodiment, the method further comprises the steps of (e) further testing the compound for its ability to inhibit tumor metastasis in an animal bearing a solid tumor, and (f) selecting the compound if it inhibits tumor metastasis in step (e).

In one embodiment, the method further comprises the steps of (e) further testing the compound for its ability to inhibit tumor metastasis to the lungs and liver in an animal bearing a solid tumor known to metastasize the lungs or liver; and (f) selecting the compound if it inhibits tumor metastasis in step (e).

In one embodiment, the method further comprises the steps of (e) further testing the compound for its ability to treat sepsis in a patient; and (f) selecting the compound if it treats sepsis in step (e).

In one embodiment, the method further comprises the steps of (e) further testing the compound for its ability to treat bacterial sepsis in a patient; and (f) selecting the compound if it treats sepsis in step (e).

In one embodiment, the method further comprises the steps of (e) further testing the compound for its ability to treat acute kidney damage in a patient; and (f) selecting the compound if it treats acute kidney damage in step (e).

In one embodiment, step (a) in the method includes screening a library of test compounds for their ability to bind to DPEP-1.

All publications and patent applications mentioned in this specification are herein incorporated by reference to the same extent as if each independent publication or patent application is specifically and individually indicated to be incorporated by reference.

EXAMPLES

Example 1: Characterization of Renal Dipeptidase (DPEP-1) in the Kidney

Figure 1B:
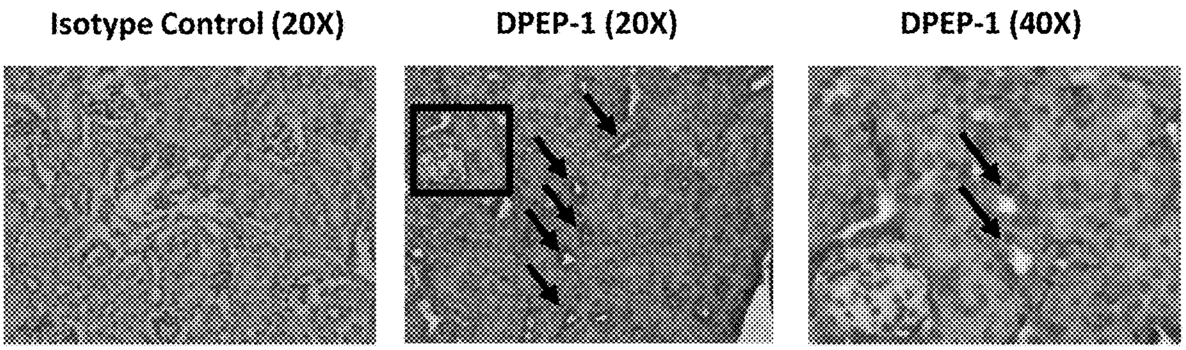
FIG. 1B provides representative photomicrographs of mouse kidney tissue was stained with DPEP-1 antibody and visualized using immunoperoxidase Arrows indicate tubules that are positive for DPEP-1, as indicated by dark brown staining.
Figure 1C:
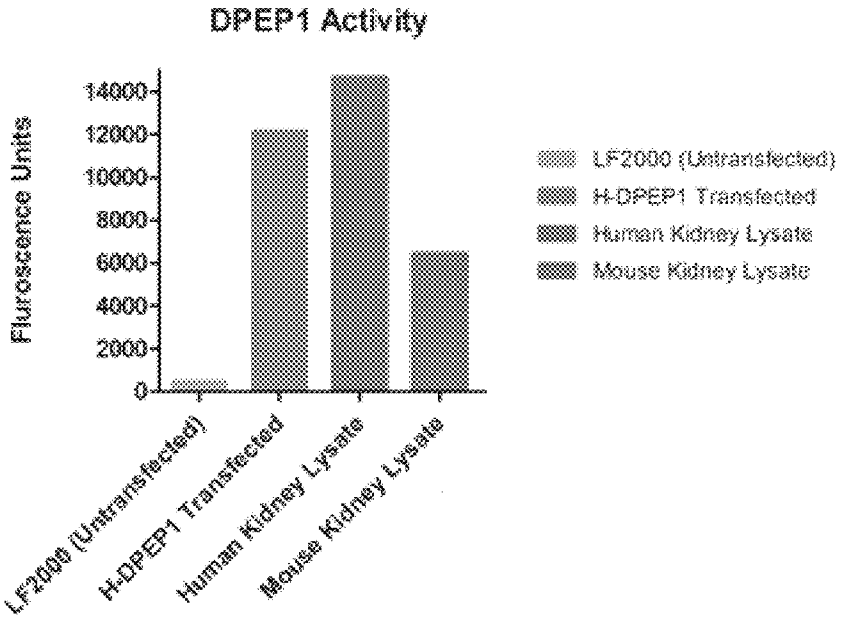
FIG. 1C provides a graph showing DPEP-1 enzymatic activity of total protein lysates prepared from untransfected COS-7 cells, COS-7 cells overexpressing DPEP-1, human kidney tissue, and mouse kidney tissue.

Renal tubular epithelial cells (TEC) were isolated and cultured from human kidney nephrectomies. Cells were then labeled with DPEP-1 and ZO-1 (a TEC surface marker) antibodies and imaged using confocal microscopy. Images were taken at 60× magnification. Representative photomicrographs are shown in FIG. 1A. Mouse kidney tissue was stained with DPEP-1 antibody and visualized using immunoperoxidase. Arrows indicate tubules that are positive for DPEP-1 as indicated by dark brown staining. Representative photomicrographs are shown in FIG. 1B. Total protein lysates were prepared from untransfected COS-7 cells, COS-7 cells overexpressing DPEP-1, human kidney tissue, and mouse kidney tissue. Lysates were then tested for DPEP-1 enzymatic activity by via fluorometric detection of the breakdown of glycine-dehydro-phenylalanine (Gly-D-Phe), a dipeptide substrate for DPEP-1. These results are shown graphically in FIG. 1C

Example 2: Endogenous DPEP-1 Activity In Vivo

Figure 2:
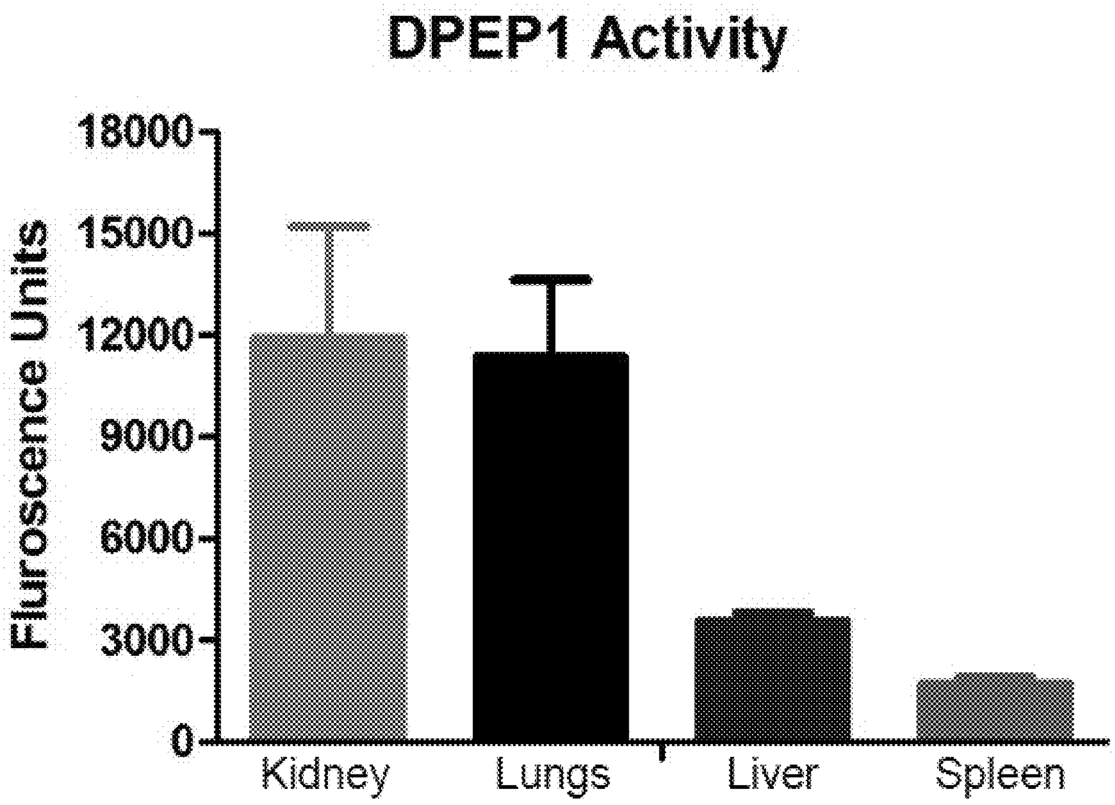
FIG. 2 provides a graph showing DPEP-1 enzymatic activity of total protein lysates isolated from Organs (Lungs, Liver, Spleen and Kidney) harvested from 8-10 weeks old C57/BL6 animals.

Organs (Lungs, Liver, Spleen and Kidney) were harvested from 8-10 weeks old C57/BL6 animals (Charles River). Proteins were isolated from tissues using RIPA/Octyl-glucoside in the absence of protease inhibitor cocktails using a tissue homogenizer 10 /\1 of the protein lysate from each condition/organ was used to perform DPEP-1 enzyme activity assay. These results are shown graphically in FIG. 2.

Example 3: Lung Expression of DPEP-1

Figure 3:
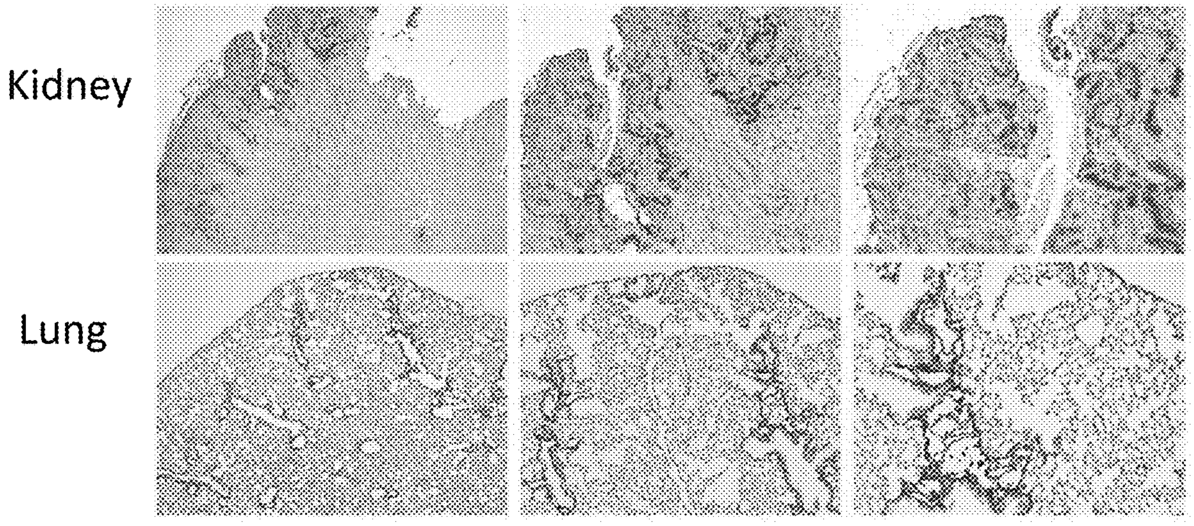
FIG. 3 provides representative photomicrographs of kidney and lung sections stained with a DPEP-1 specific antibody (brown (Abcam)] using the DAB method to assess DPEP-1 expression.

Organs (Lungs, and Kidney) were harvested from 8-10 weeks old C57/BL6 animals (Charles River) and tissues were paraffin embedded for histology. Kidney and lung sections were stained with a DPEP-1 specific antibody (brown (Abcam)] using the DAB method to assess DPEP-1 expression. Representative photomicrographs are shown in FIG. 3.

Figure 4A:
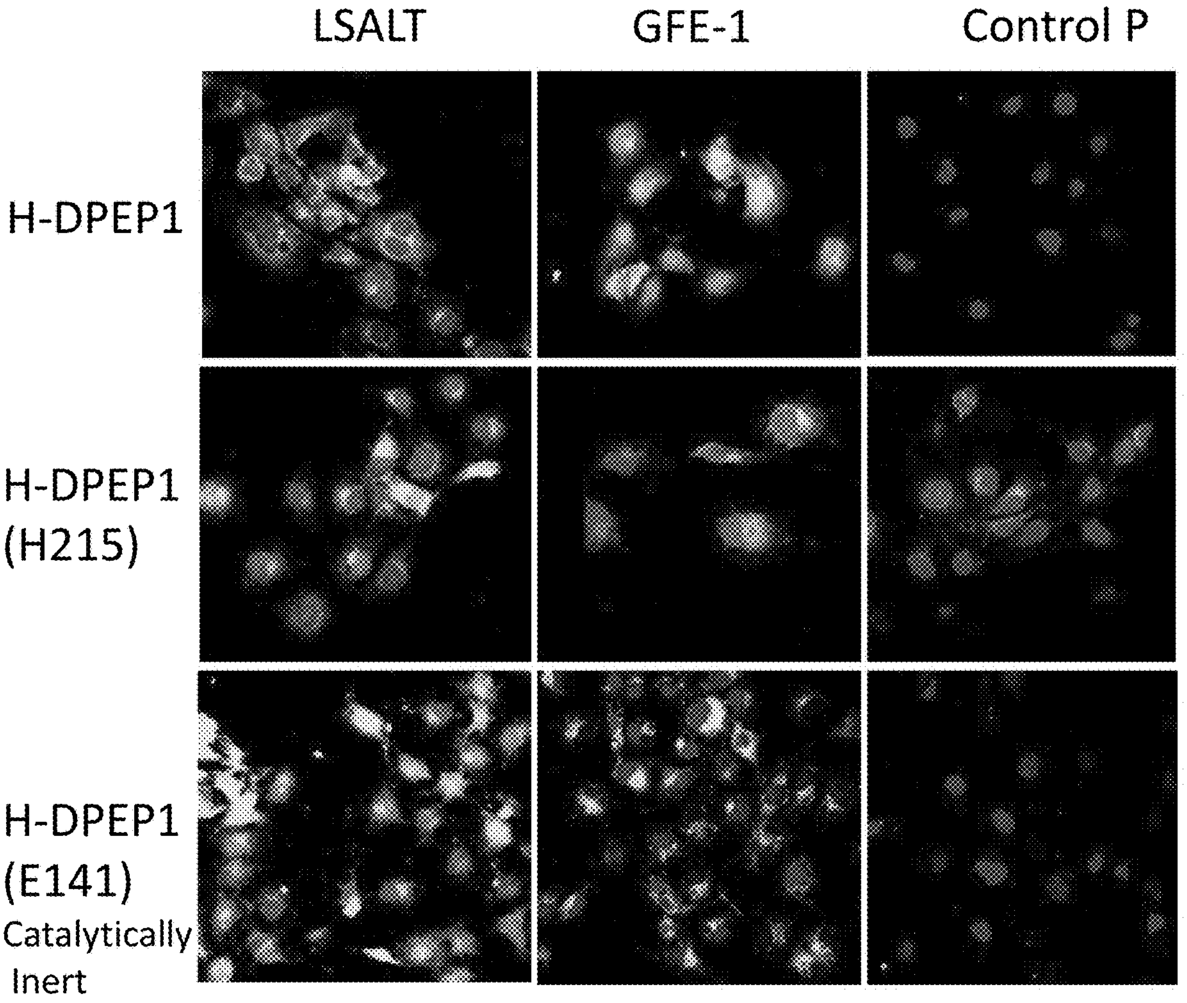
FIG. 4A provides representative photomicrographs of each experimental condition (n=3) are shown in FIG. 4A. These results are shown graphically in FIG. 4B. A photograph of the western blot analysis is shown in FIG. 4C.
Figure 4B:
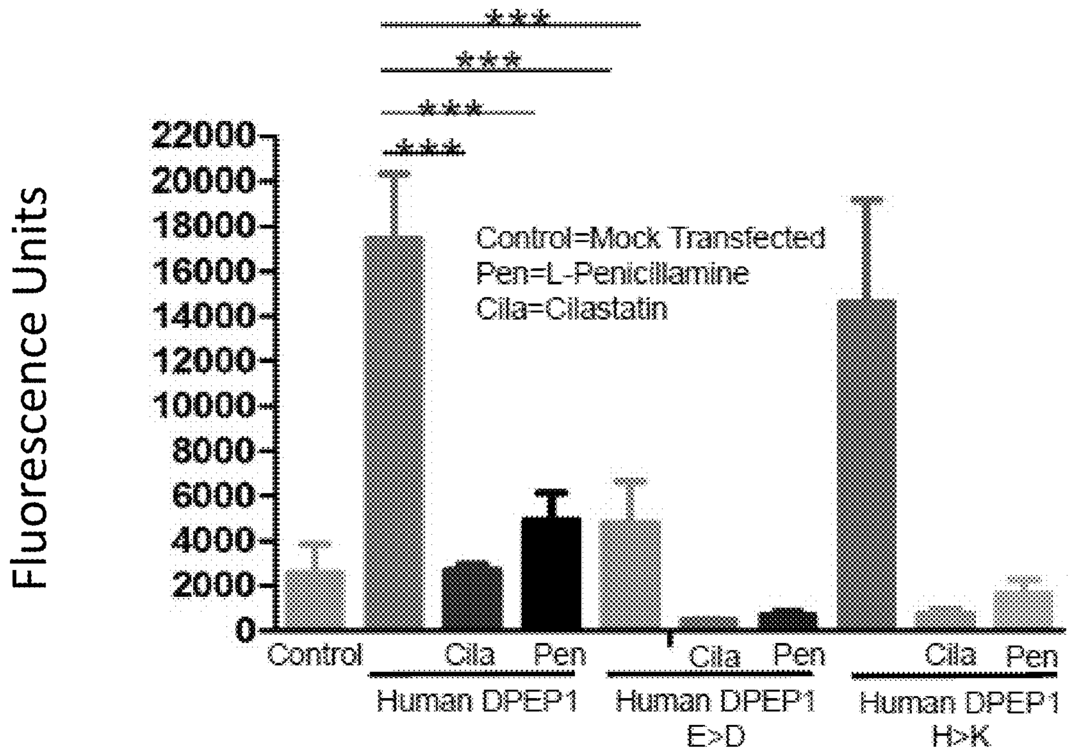
Figure 4C:
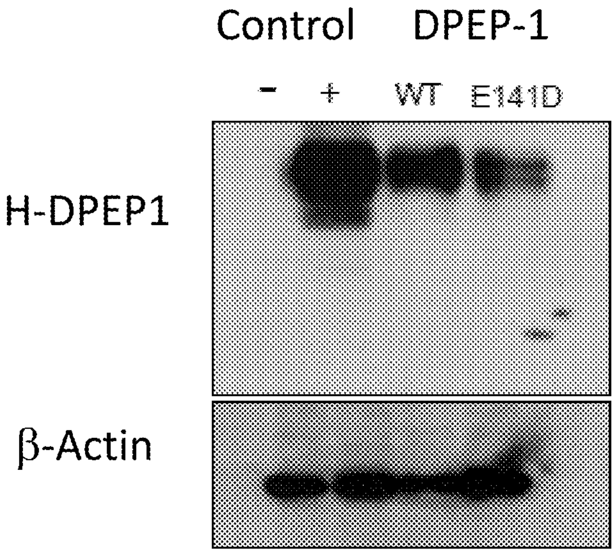

Example 4: Catalytic Activity of DPEP-1 is not Required for Binding In Vitro Cos-1 cells were transiently transfected with 3|ig of either the wild type membrane dipeptidase (DPEP-1) catalytically inert mutant (E>D) or mutant contol (H>K) corresponding to the human DPEP-1 gene using lipofectamine 2000 (Invitrogen) reagent. 24 hours after transfection, DPEP-1 expressing cells weer reseeded on 24 well collagen coated (neutralized) plates and allowed to grow for 24 hours at 37° C. 24 hours after seeding, media was removed and cells were washed with PBS Cells were blocked with FBS/NBSA/Tween in PBS for 30 minutes on ice. Cells were then washed with PBS and incubated with Alexa-488 (green) conjugated LSALT, GFE-1, control peptide or DPEP-1 antibody (1/100) (Sigma) on ice for 30 minutes. After incubation, cells were washed with PBS and stained with DAPI for 4 minutes on ice. Cells were again washed with PBS, fixed using 4% paraformaldehyde and immunofluorescence microscopy was performed to assess binding. Representative photomicrographs of each experimental condition (n=3) are shown in FIG. 4A. Proteins from human DPEP-1 transfected cells were isolated after 48 hours using octyl-glucoside/RIPA in the absence of protease inhibitors Membrane dipeptidase activity assay and the fluorometric detection of D-Phe was performed exactly as described earlier according to the principles originally established by Heywood and Hooper (1995). These results are shown graphically in FIG. 4B. Values shown are the mean±s.e.m, from six independent experiments; asterisks (*) indicate P<0.001 as compared with DPEP-1 transfected cells (one-way ANOVA with the Neuman-Keuls post-test)(n=5) Proteins from transfected cells were isolated after 48 hours using octyl-glucoside/RIPA lysis buffer and western blot analysis was performed to assess DPEP-1 expression using DPEP-1 antibody (Sigma). A photograph of the western blot analysis is shown in FIG. 4**C.

Example 5: Lsalt Bonds to Racine and Human DPEP-1

Figure 5A:
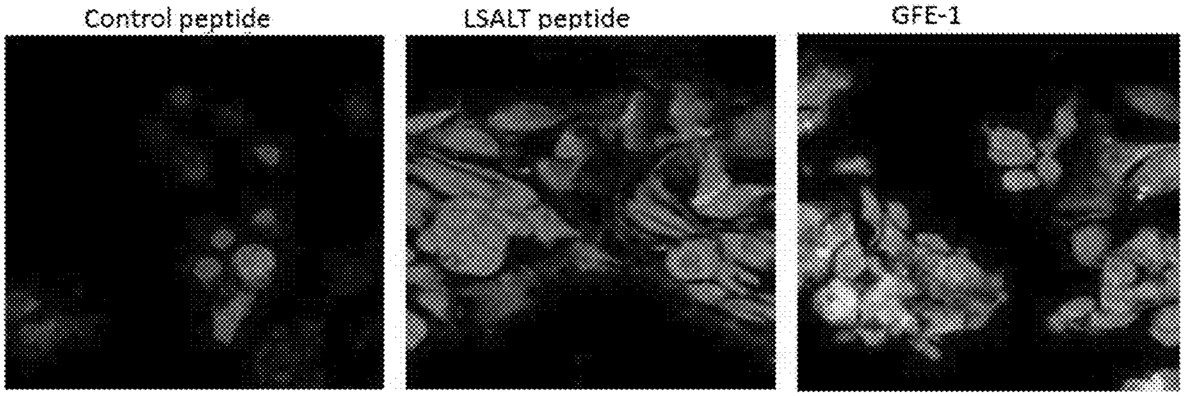
FIG. 5A and FIG. 5B provides representative photomicrographs of Cos-1 cells transiently transfected with membrane dipeptidase (DPEP-1) cDNA corresponding to the rat (FIG. 5A) or human DPEP-1 (FIG. 5B) gene. A photograph of the western blot is provided in FIG. 5C. A schematic of this procedure photograph of the resulting western blot are provided in FIG. 5D.
Figure 5B:
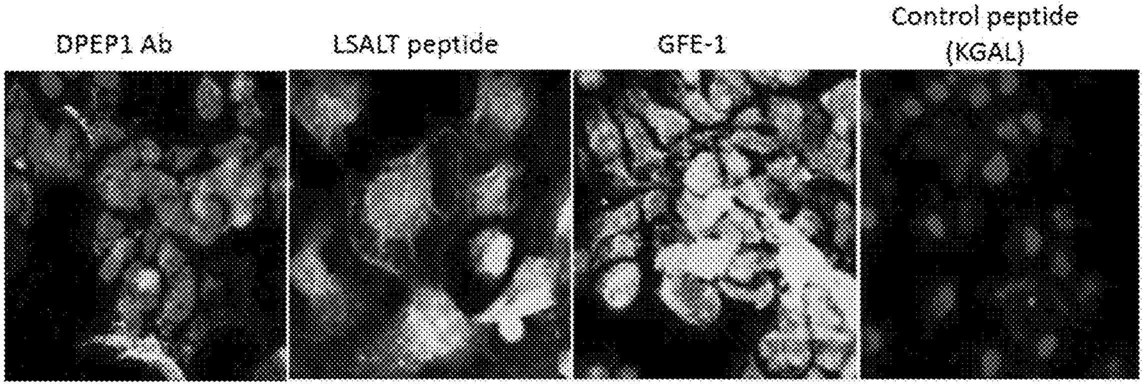
Figure 5C:
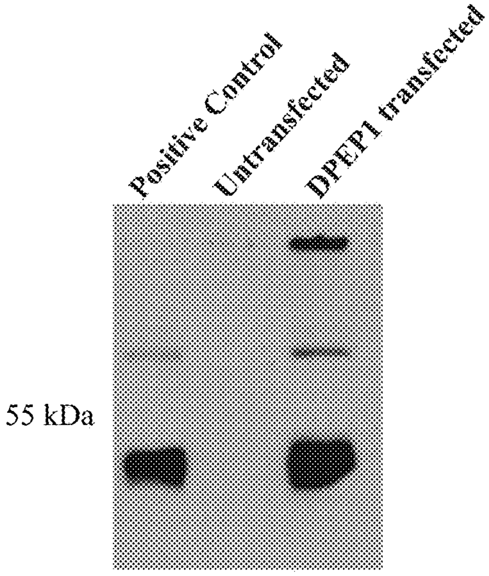
Figure 5D:
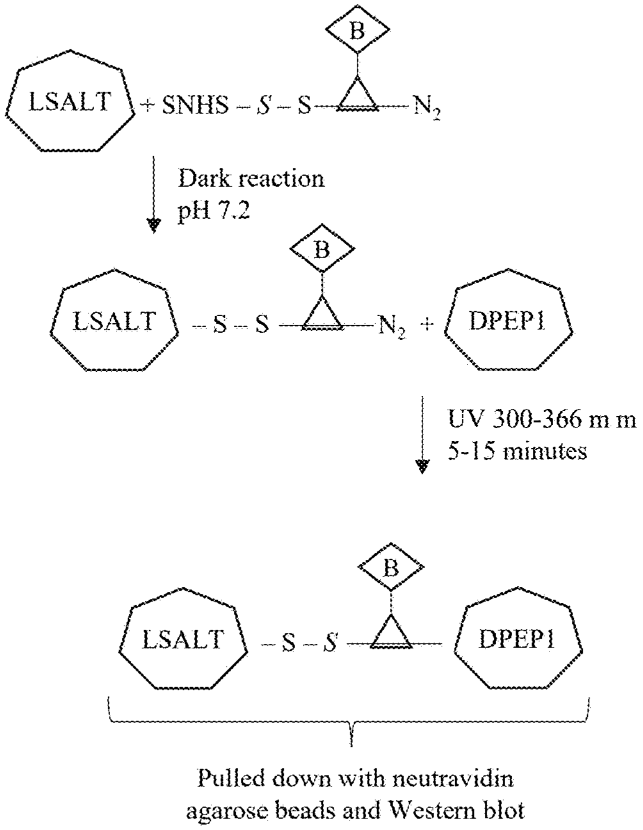
Figure 5D:
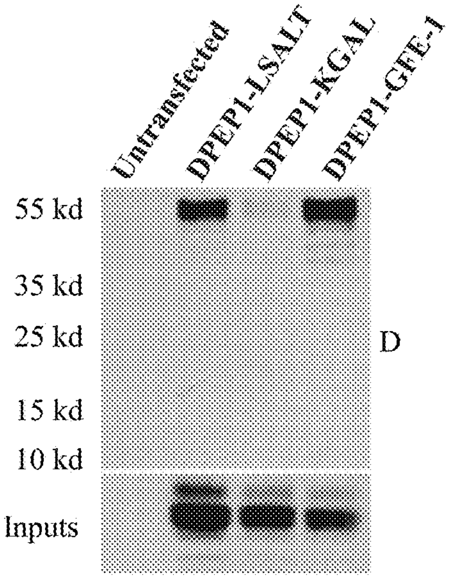

Cos-1 cells were transiently transfected with either 3 or 5|ig of membrane dipeptidase (DPEP-1) cDNA corresponding to the rat (Shown in FIG. 5A) or human DPEP-1 (Shown in FIG. 5B) gene using lipofectamine 2000 (Invitrogen) reagent in OptiMEM medium 24 hours after transfection, DPEP-1 expressing cells were re-seeded on collagen coated (neutralized) wells in 24 well plates and allowed to grow for 24 hours at 37°C. 24 hours after seeding, media was removed and cells were washed with PBS. Cells were blocked with FBS/NBSA/Tween in PBS for 30 minutes on ice. Cells were then washed with PBS and incubated with Alexa-488 (green) conjugated LSALT, GFE-1, control peptide or DPEP-1 antibody (1/100) (Sigma) on ice for 30 minutes. DPEP-1 antibody incubated cells were washed with PBS and incubated with fluorescently conjugated anti-rabbit secondary antibody (1/500 in PBS) for 30 minutes on ice. After incubation, cells were washed with PBS and stained with DAPI for 5 minutes on ice. Cells were then washed with PBS and fixed using 4% paraformaldehyde and immunofluorescent microscopy was performed to assess binding. Shown are representative photomicrographs of each experimental condition (n=5). Proteins from human DPEP-1 transfected cells were isolated after 48 hours using octyl-glucoside/RIPA lysis buffer and western blot analysis was performed to assess DPEP-1 expression using a DPEP-1 specific antibody (Sigma). A photograph of the western blot is provided in FIG. 5C. Cos-1 cells were transiently transfected with 3 pg of DPEP-1 encoding the human DPEP-1 gene. Transfected cells were serum starved in OptiMEM medium for 2 hours and treated with methyl-beta-cyclodextrin for 30 minutes. After incubation, cells were washed with PBS and treated with 10 mg/ml biotin transfer peptide (LSALT, GFE-1 or Control Peptide (KGAL)] for 10 minutes. Cells were then washed with PBS and biotin transfer was enabled by UV activation of the aryl azide groups for 15 minutes at 363 nm. Residual fluid was removed and monolayers were lysed either with octyl-glucoside/RIPA or 8M urea. Isolated supernatants were rotated with 50 pl of neutr-avidin agarose beads at 4° C. for 24 hours. Beads were washed with corresponding buffers, boiled in Laemmli buffer and analyzed by western blot using a DPEP-1 specific antibody (Proteintech). A schematic of this procedure and photograph of the resulting western blot are provided in FIG. 5D.

Example 6: Lsalt and Gfe-1 do not Bind to Human DPEP2 and DPEP-3 In Vitro

Figure 6A:
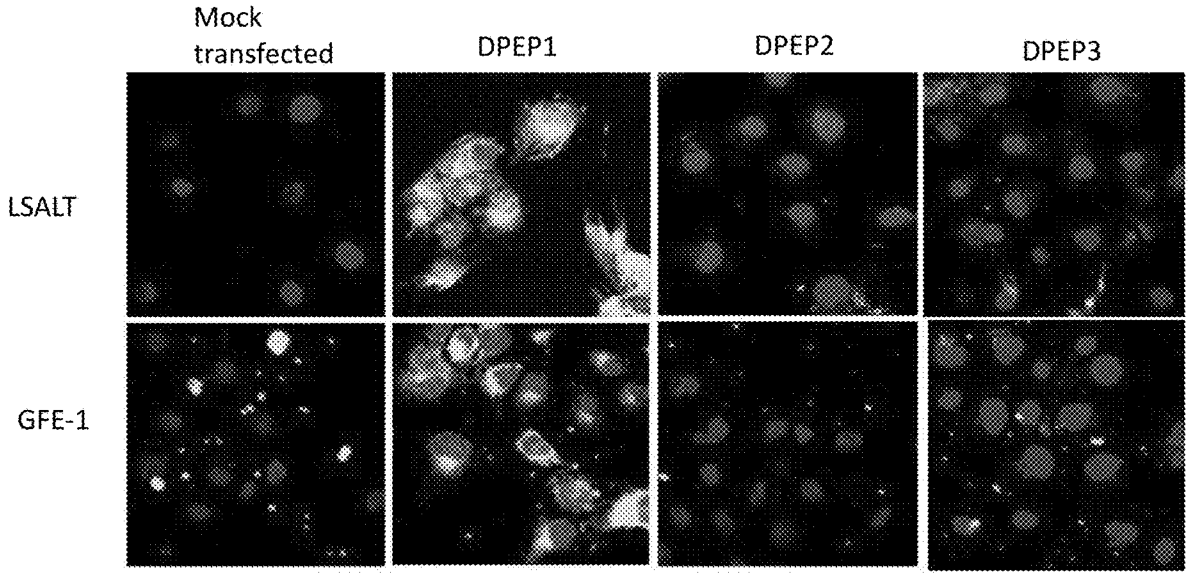
FIG. 6A provides representative photomicrographs of Cos-1 cells transiently transfected with human DPEP-1, DPEP-2, or DPEP-3 gene. Proteins from DPEP-1, DPEP2 and DPEP3 transfected cells were isolated and photographs of the western blots are shown in FIG. 6B.
Figure 6B:
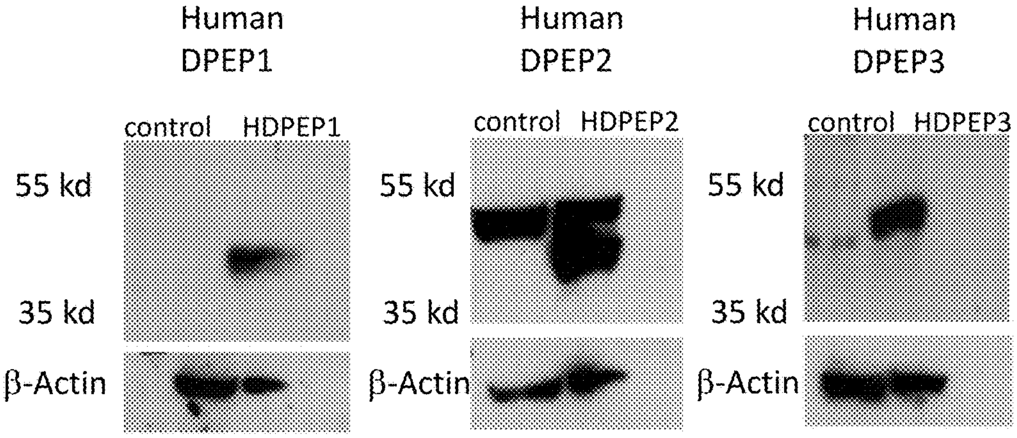

Cos-1 cells were transiently transfected with either 3 pg of human DPEP-1, DPEP2, or DPEP3 gene using lipofectamine 2000 (Invitrogen) reagent in OptiMEM medium. 24 hours after transfection, DPEP-1, DPEP2, or DPEP3 expressing cells were re-seeded on collagen coated (neutralized) wells in 24 well plates and allowed to grow for 24 hours at 37°° C. 24 hours after seeding, media was removed and cells were washed with PBS. Cells were blocked with FBS/NBSA/Tween in PBS for 30 minutes on ice. Cells were then washed with PBS and incubated with LSALT or GFE-1, conjugated with Alexa-488 (green). After incubation, cells were washed with PBS and stained with DAPI for 5 minutes on ice. Cells were then washed with PBS and fixed using 4% paraformaldehyde and immunofluorescence microscopy was performed to assess binding. Representative photomicrographs are shown for each experimental condition (n=3) in FIG. 6A. Proteins from DPEP-1. DPEP2 and DPEP3 transfected cells were isolated after 48 hours using octylglucoside/RIPA lysis buffer and western blot analysis was performed to assess DPEP-1, DPEP2 and DPEP3 protein expression using specific antibodies; DPEP-1 antibody (Sigma), DPEP2 (Abcam) and DPEP3 (Santacruz). Blots were stripped and reprobed with an anti-P-actin. Photographs of the western blots are shown in FIG. 6B.

Figure 7A:
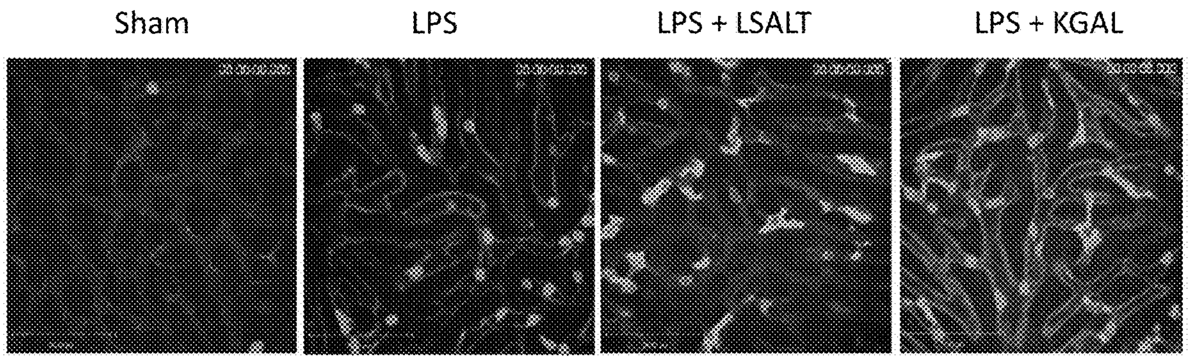
FIGS. 7A and 7B provide a graph showing GFE-1 and LSALT inhibit neutrophil adhesion in the hepatic sinusoids in the presence of LPS.
Figure 7B:
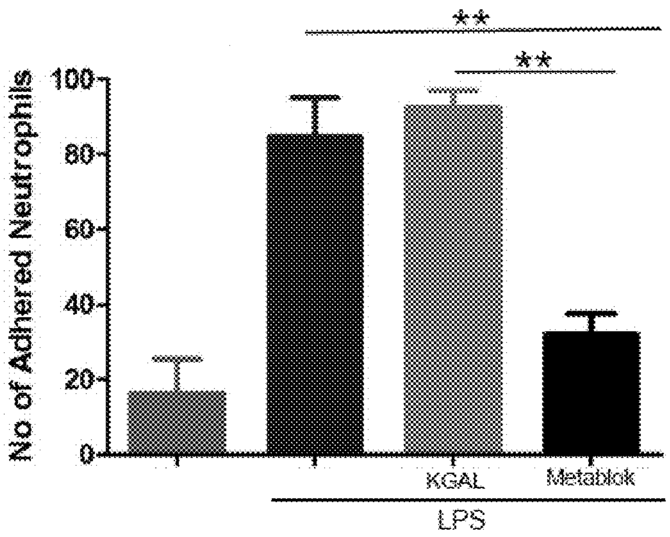

Example 7. Gfe-1 and Lsalt Inhibit Neutrophil Adhesion in the Hepatic Sinusoids in the Presence of Lps Six to ten week old LysMeGFP mice were injected with 1 mM dose of LSALT or GFE-1 peptides (intravenous) 5 minutes after the injection of 0.5 mg/kg of lipopolysaccharide (intraperitoneal). After 3 hours, animals were injected with ketamine and xylazine to provide general anesthesia. Fluorescently conjugated F4/80 and PECAM-1 antibodies were then administered via jugular vein cannulation and intravital spinning disk confocal microscopy was performed. The livers were imaged for an hour and the number of neutrophils were counted at different time points. Neutrophils which were stationary for >30 seconds in the liver sinusoids were counted as adherent cells. Data are representative of three independent experiments. An unpaired 2-tailed student's t-test was performed comparing LSALT, GFE-1 or control treated group against the LPS treated group (*p<0.05). The results are shown in FIG. 7.

Figure 8:
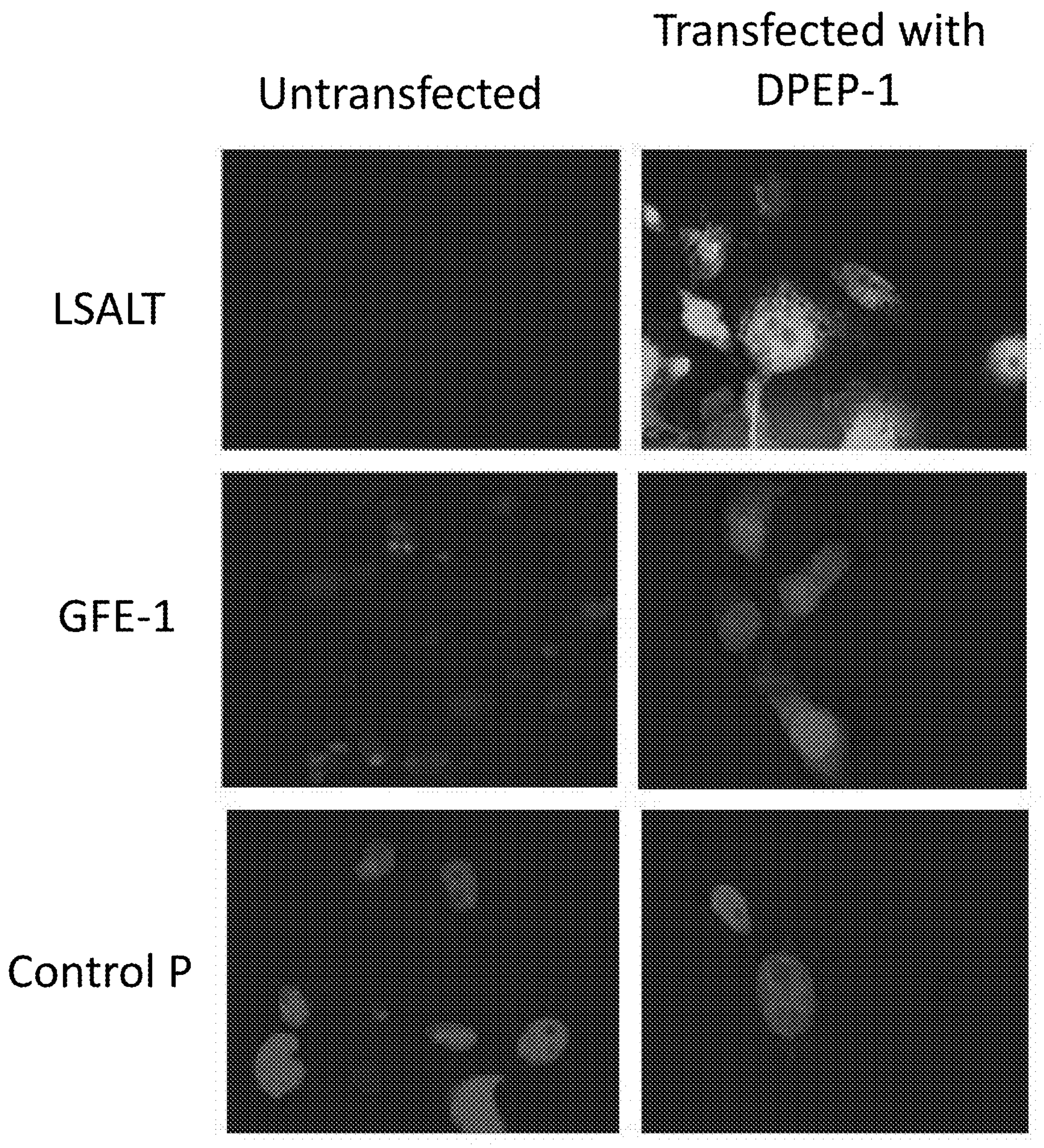
FIG. 8 provides photomicrographs showing expression of DPEP-1 enhanced the binding of LSALT and GFE-1 in Cos-7 cells.

Example 8: Expression of DPEP-1 Enhanced the Binding of Lsalt and Gfe-1 in Cos-7 Cells Cos-7 cells were transiently transfected with 5 g of renal rat membrane dipeptidase (DPEP-1) plasmid using lipofectamine 2000 (Invitrogen) reagent. 48 hours after transfection, media was removed and cells were washed with PBS. Cells were incubated with LSALT conjugated with Alexa-488 (Green), GFE-1 peptide conjugated with Alexa-568 (Red) or control peptide conjugated with Alexa-488 (Green) on ice for 30 minutes. Cells were washed and fixed using 4% paraformaldehyde and immunofluorescence microscopy was performed to assess binding. Shown are representative photomicrographs of each experimental condition (n=2). The results are shown in FIG. 8.

Example 9. Expression of DPEP-1 Enhanced the Binding of Lsalt to Cos-7 Cells

Figure 9:
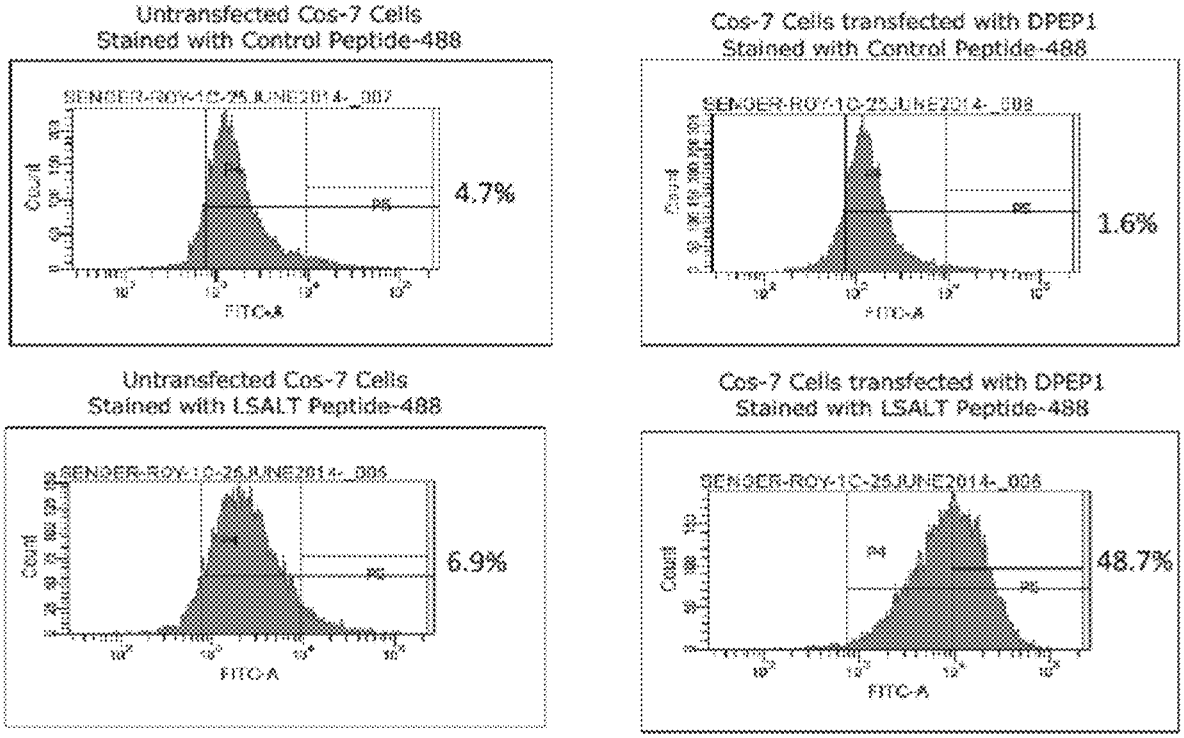
FIG. 9 provides single parameter histograms showing that expression of DPEP-1 enhanced the binding of LSALT to Cos-7 cells.

Cos-7 cells were transiently transfected with 5/\g of renal rat membrane dipeptidase (DPEP-1) plasmid using lipofectamine2000 (Invitrogen) reagent. 48 hours after transfection, cells were incubated with LSALT conjugated to Alexa-488 (green) on ice for 30 minutes. Cells were washed and flow cytometry was performed to assess binding Shown are single parameter histographs for each experimental condition (n=2). The results are shown in FIG. 9.

Figure 10A:
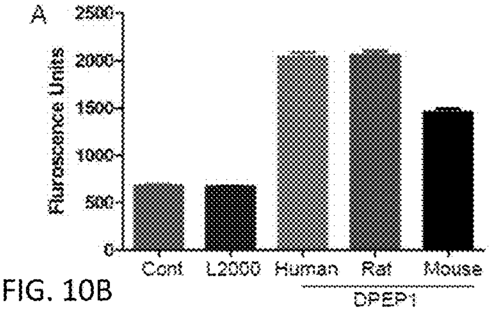
FIGS. 10A, 10B, and 10C provide a graph showing that LSALT does not inhibit membrane dipeptidase enzyme activity.
Figure 10B:
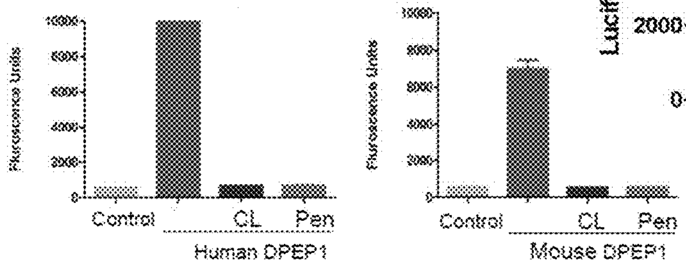
Figure 10C:
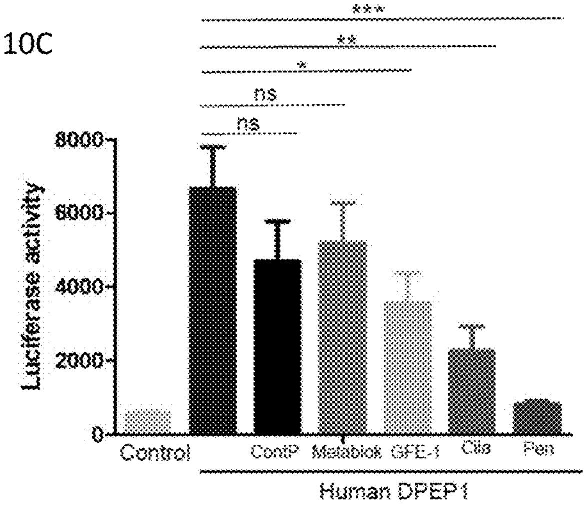

Example 10: Lsalt does not Inhibit Membrane Dipeptidase (DPEP-1) Enzyme Activity Cos-1 cells were transiently transfected with 3 pg of human membrane dipeptidase (DPEP-1) plasmid using lipofectamine 2000 (Invitrogen) reagent. 48 hours after transfection, media was removed and cells were washed with PBS. Proteins were isolated using octylglucoside in the absence of protease inhibitors. Membrane dipeptidase assay and the fluorimetric detection of D-Phe was performed exactly as described by Heywood and Hooper previously. In brief, proteins were first incubated with membrane dipeptidase substrate Gly-D-Phe either in the presence or absence of LSALT or GFE-1 peptide at 37° C. for 3 hours. The fluorescence signal generated from the conversion of D-Phe to 6,69-dihydroxy-(1,19-biphenyl)-3,39-diaceticacid in the presence of D-aminoacidoxidase and peroxidase was measured using a fluorescence plate reader. The results are shown in FIG. 10A-C.

Example 11: Inhibition of Renal Dipeptidase During Sepsis Reduces Inflammation

Figure 11A:
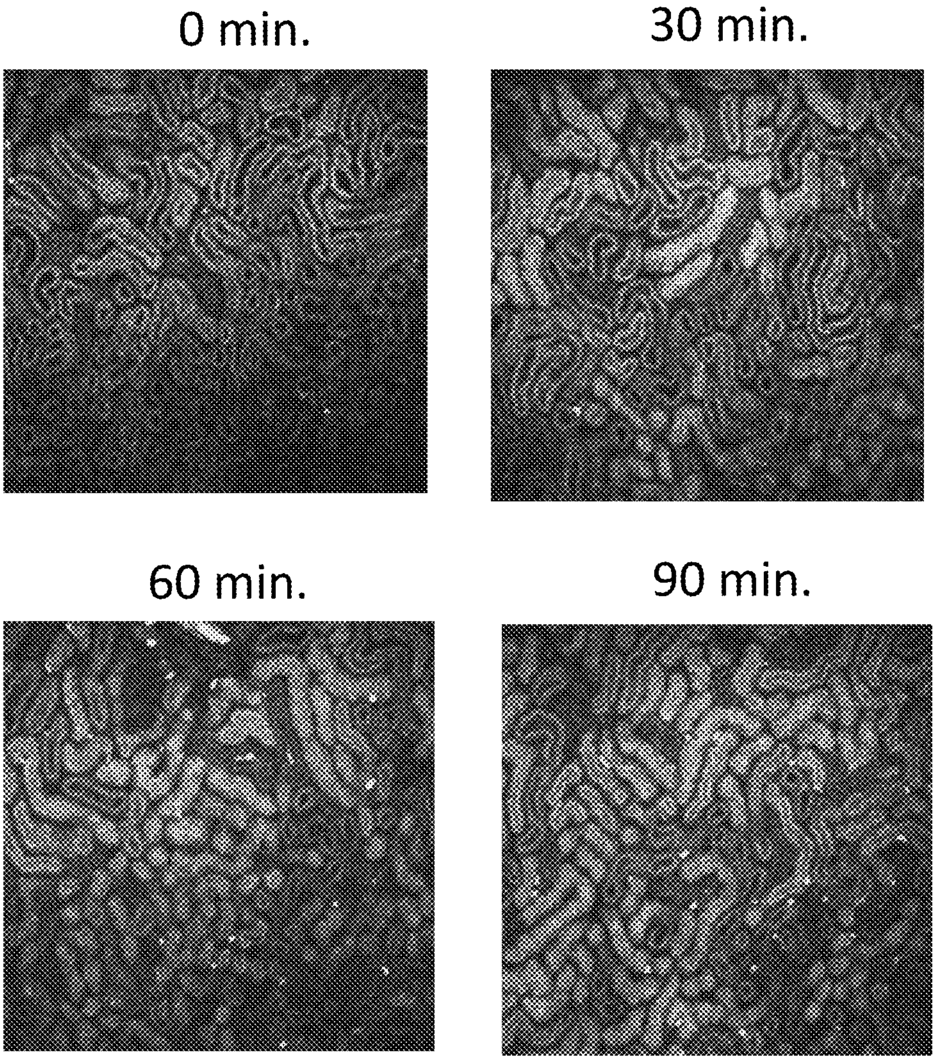
FIG. 11A to FIG. 11C provides representative photomicrographs of LysM (gfp/gfp) mice kidney subjected to LPS-induced sepsis and imaged every 30 min for up to 90 min (FIG. 11A).
Figure 11B:
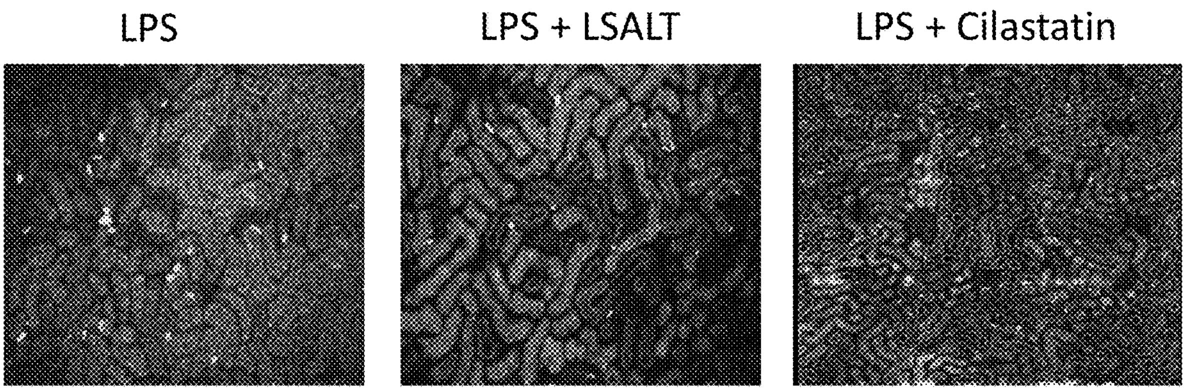
Figure 11C:
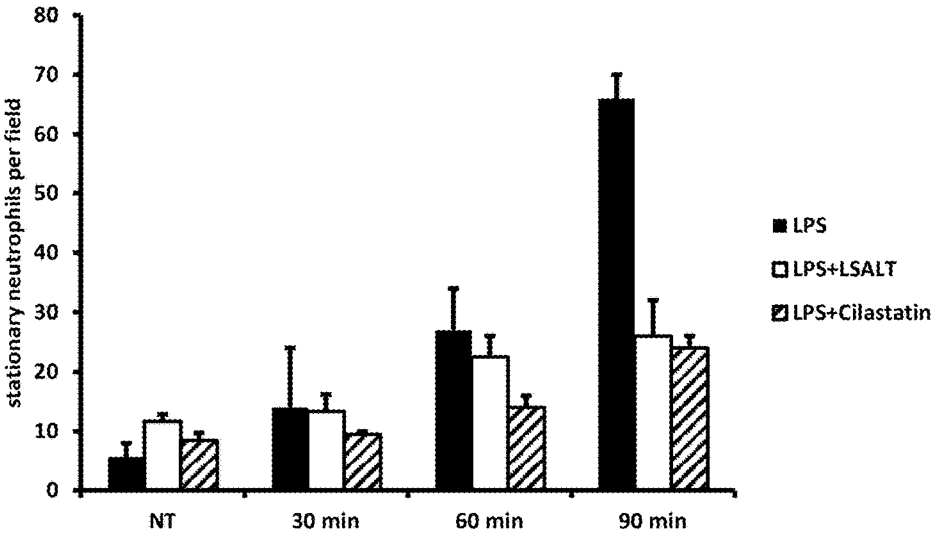

LysM (gfp/gfp) mice were subjected to sepsis via intravenous injection of lipopolysaccharide (LPS) at a dose of 5 mg/kg. The kidney was imaged using multiphoton microscopy every 30 min. for up to 90 min Inhibitors of dipeptidase were used intravenously to pretreat mice 10 min. before LPS injection. Photomicrographs are shown in FIG. 11A. FIG. 11B provides photomicrographic images of kidney before (NT) and after LPS (90 min.) with various inhibitors. Adherent neutrophils were seen in interstitial spaces after IRI. Neutrophils were quantified over a 90 min. time course after LPS injection with various DPEP-1 inhibitors, n=2-3/group, *: p<0.05. These results are shown graphically in FIG. 11C.

Figure 12A:
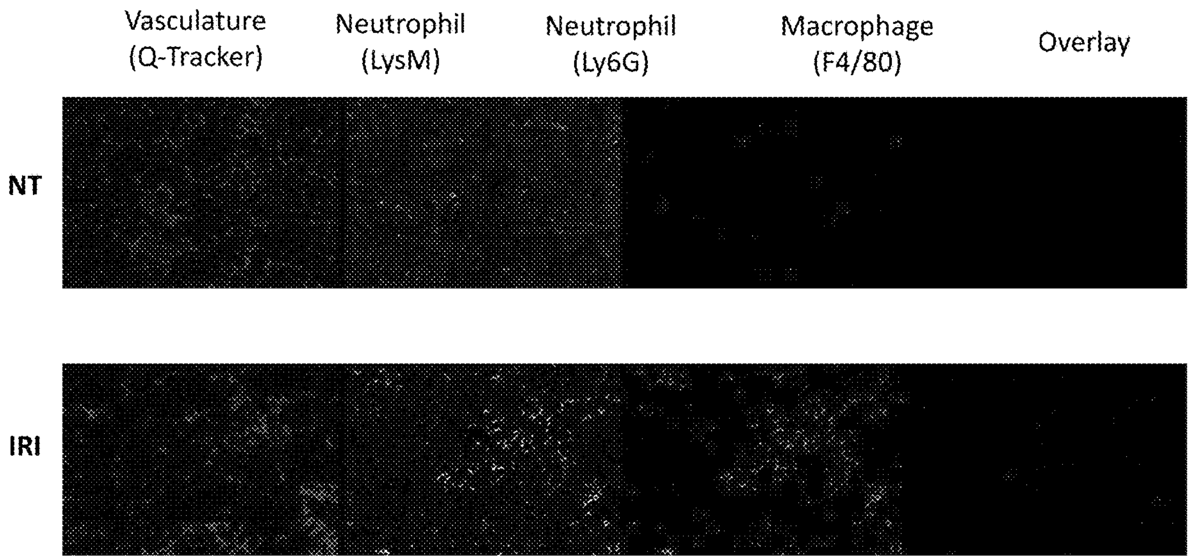
FIG. 12A provides representative photomicrographs of LysM (gfp/gfp) mice kidney subjected to 30 min. of unilateral renal ischemia and 120 min. of reperfusion and imaged using multiphoton microscopy. Inhibitors of dipeptidase were used to pretreat mice 10 min. before ischemia and labeling antibodies were injected intravenously before imaging. Images of kidney before (NT) and after IRI (120 min.) with various inhibitors are provided in FIG. 12B. Adherent neutrophils seen in interstitial spaces after IRI were quantified and shown graphically in FIG. 12C. Neutrophils were quantified after IRI (120 min.) with various inhibitors and shown graphically in FIG. 12D.
Figure 12B:
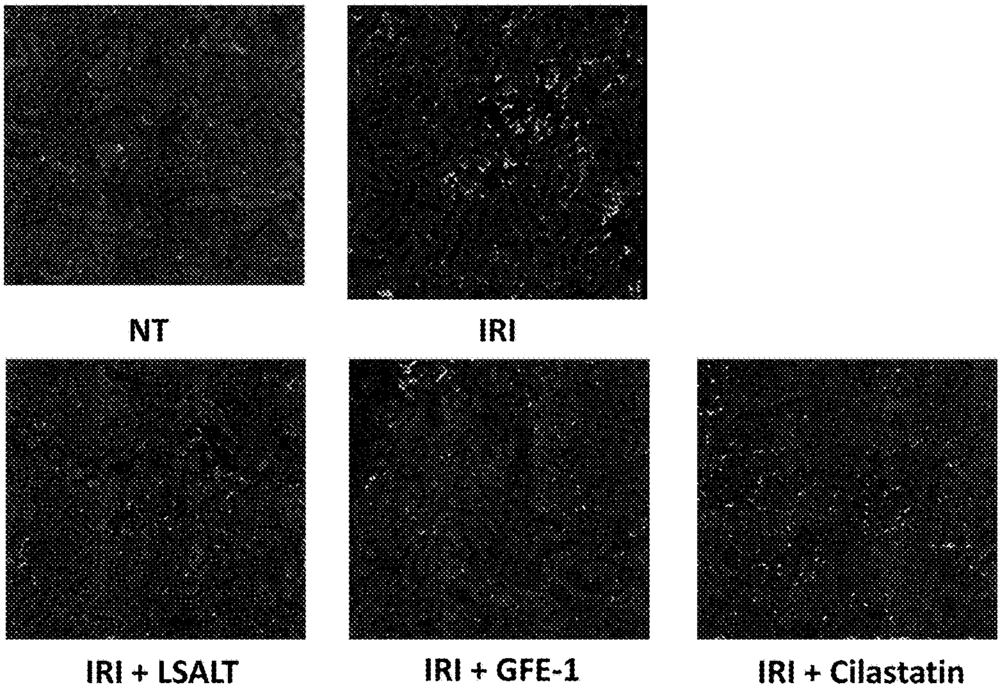
Figure 12C:
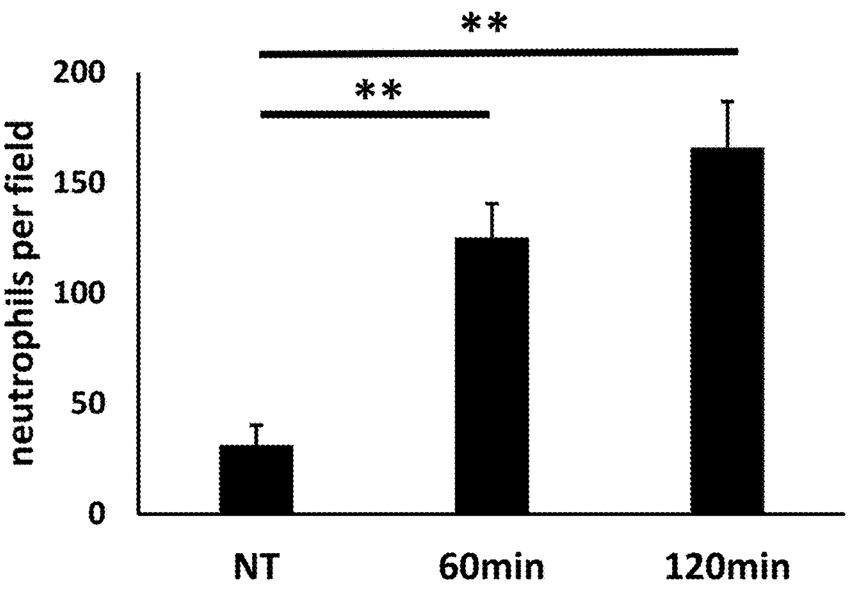
Figure 12D:
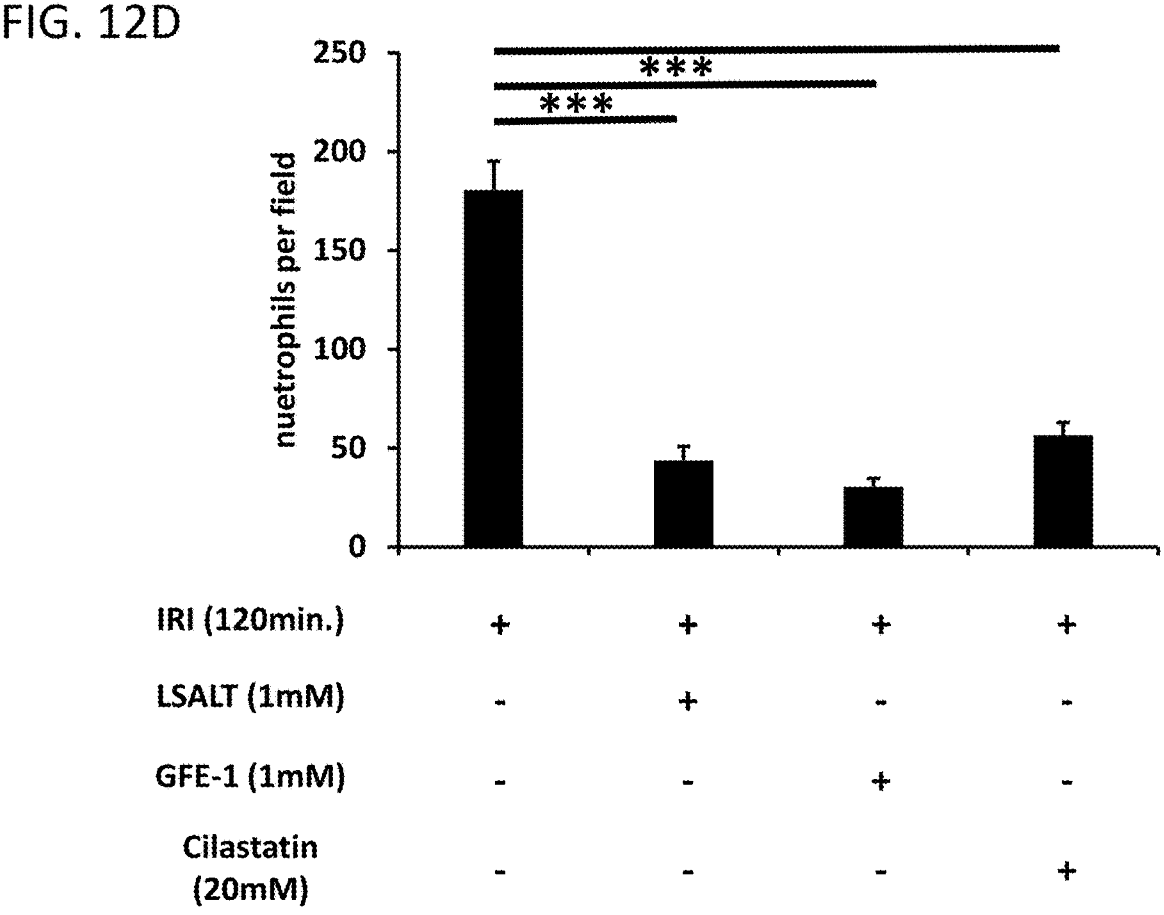

Example 12: Inhibition of Dipeptidase During Renal Ischemia Reperfusion Injury Reduces Inflammation LysM (gfp/gfp) mice were subjected to 30 min. of unilateral renal ischemia at 37° C. via vascular clamp and 120 min. of reperfusion and the affected kidney was imaged using multiphoton microscopy. Representative photomicrographs are shown in FIG. 12A. Inhibitors of dipeptidase were used to pretreat mice 10 min before ischemia. Labeling antibodies were injected intravenously before imaging. Images of kidney before (NT) and after IRI (120 min.) with various inhibitors are provided in FIG. 12B. Adherent neutrophils were seen in interstitial spaces after IRI. Neutrophils were quantified over a 120 min. time course and shown graphically in FIG. 12C (n=3/group, *: p<0.01). D) Neutrophils were quantified after IRI (120 min.) with various inhibitors and shown graphically in FIG. 12D (n=3-5/group, *: p<0.001).

Figure 13A:
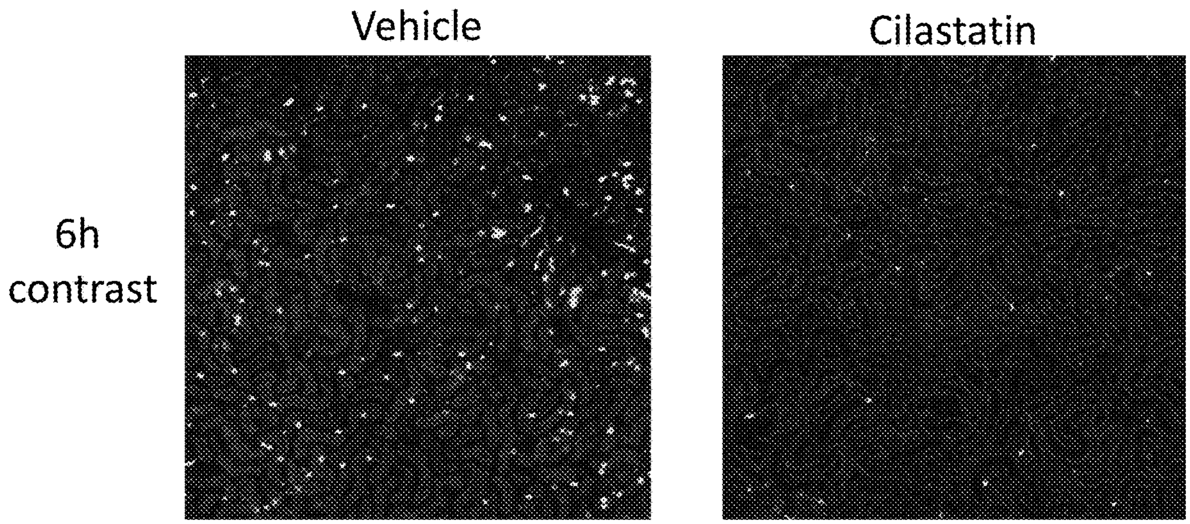
FIG. 13A provides representative photomicrographs of LysM (gfp/gfp) mice sensitized to acute renal injury by dehydration prior to intravenous injection of contrast Cilastatin (5 mM) was used intravenously to pretreat mice 10 min. before contrast injection and the kidney was imaged 6 hours post-injection of contrast using multiphoton microscopy. Neutrophils were quantified 6 hours after contrast and these results are shown graphically in FIG. 13B.
Figure 13B:
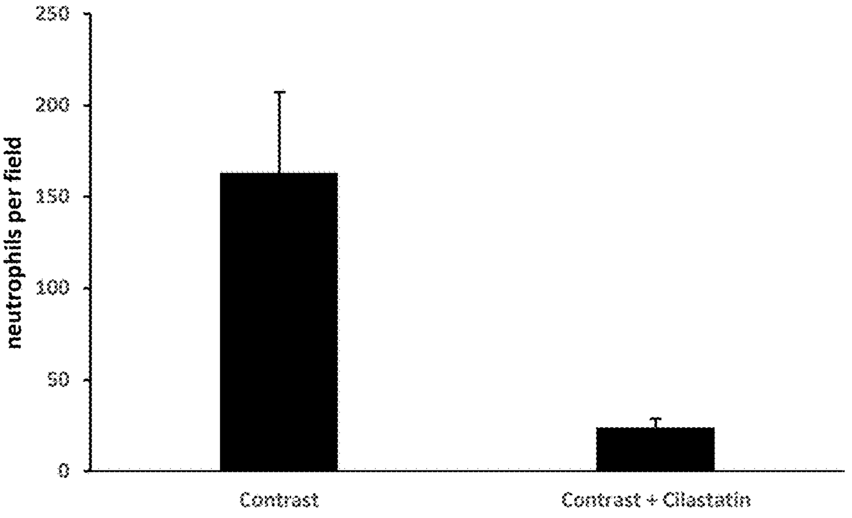

Example 13: Inhibition of Dipeptidase (DPEP-1) During Intravenous Contrast Reduces Inflammation LysM (gfp/gfp) mice were sensitized to acute renal injury by dehydration prior to intravenous injection of contrast (5 mL/kg). Cilastatin (5 mM) was used intravenously to pretreat mice 10 min. before contrast injection. Kidney was imaged 6 hours post-injection of contrast using multiphoton microscopy Representative photomicrograph is provided in FIG. 13A. Neutrophils were quantified 6 hours after contrast and these results are shown graphically in FIG. 13B.

Example 14: Inhibition of Inflammatory Mediators by DPEP-1 Binding

The following experiments were performed to assess if DPEP-1 binding by LSALT peptide had an effect on the level of specific serum cytokines in response to LPS.

6-8 weeks old SCID mice were given an intraperitoneal injection of LPS (0.5 mg/kg) 5 minutes prior to intravenous injection of LSALT peptide or a control peptide. 4 hours following injection of LPS, blood was collected by cardiac puncture and changes in plasma cytokine levels were assessed using Luminex Cytokine Arrays. Bar graphs show the levels of different inflammatory mediators released in the plasma in the presence or absence of LSALT peptide and control peptide. (FIG. 14A-FIG. 14G) LSALT peptide attenuates the levels of a number of different serum cytokines.

Figure 14A:
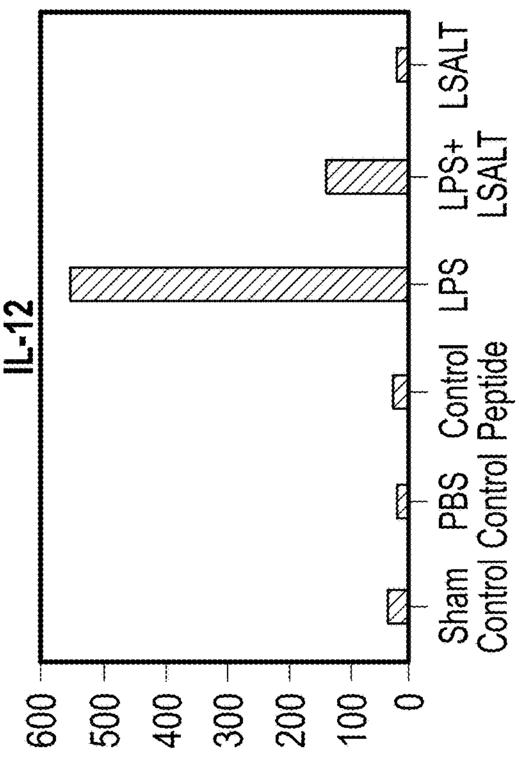
FIG. 14A-G provide graphs showing the reduction in inflammatory mediators induced by LPS in the presence of LSALT peptide.
Figure 14B:
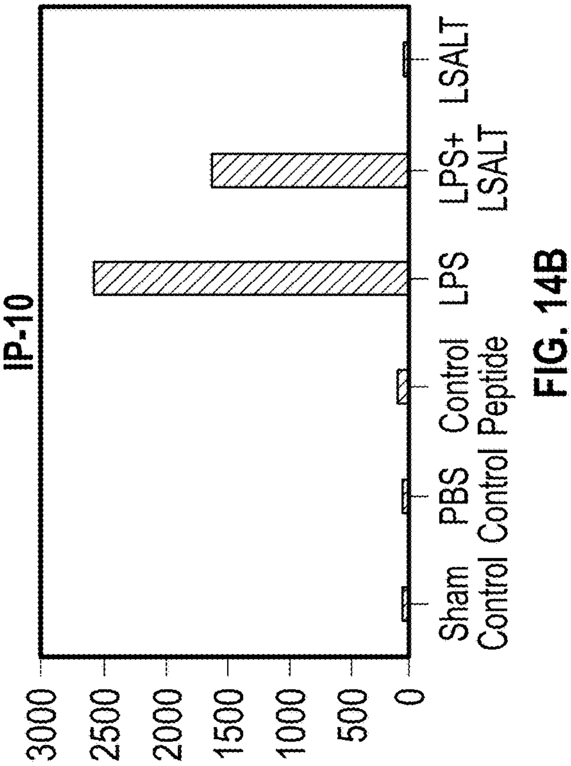
Figure 14C:
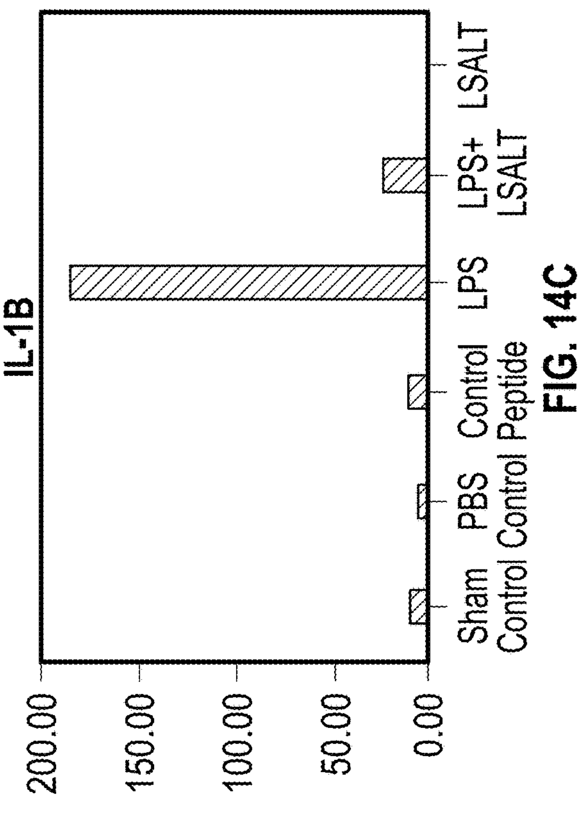
Figure 14D:
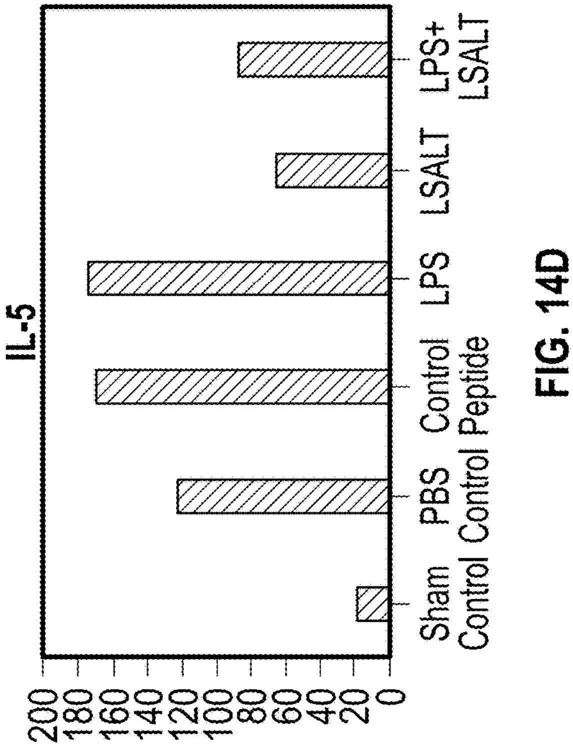
Figure 14E:
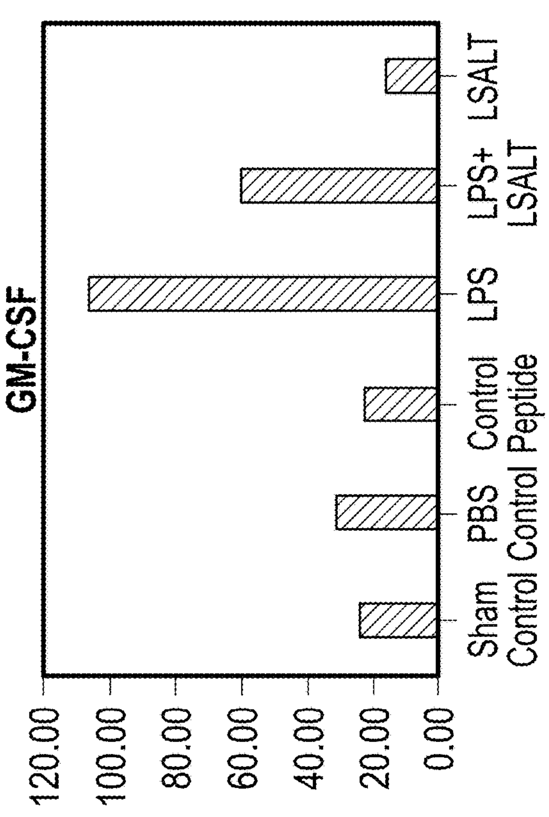
Figure 14F:
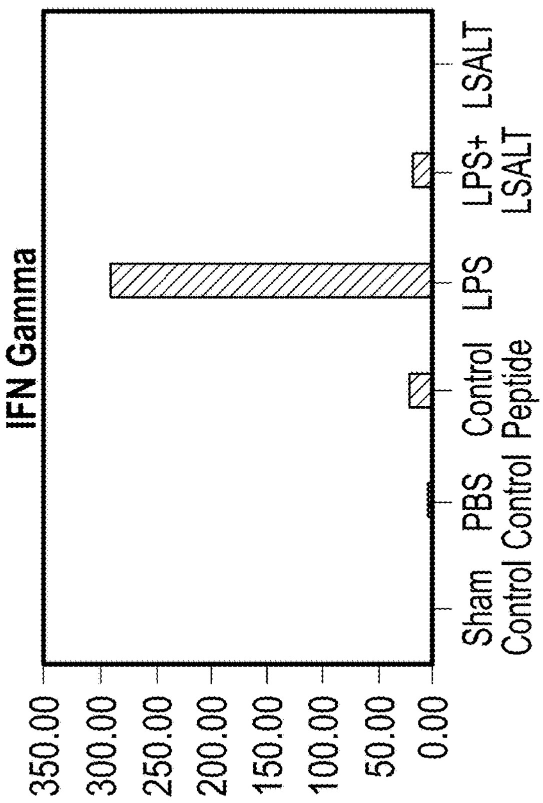
Figure 14G:
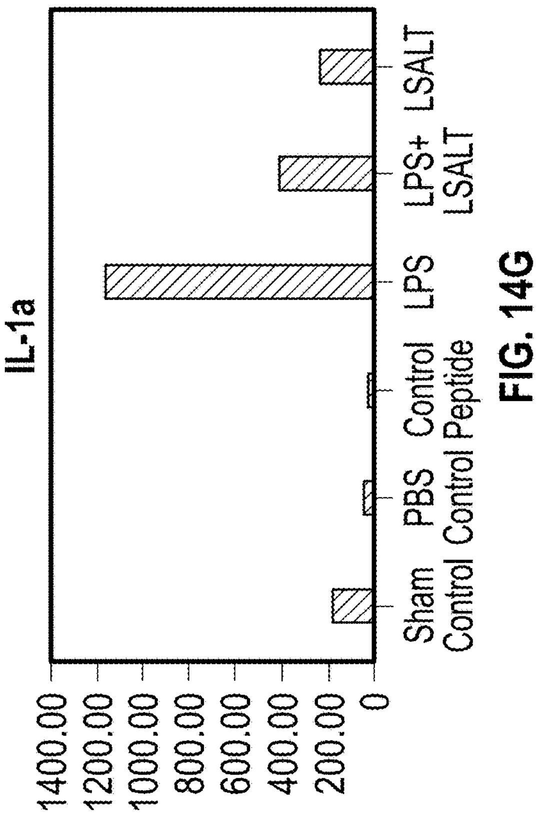
Figure 14H:
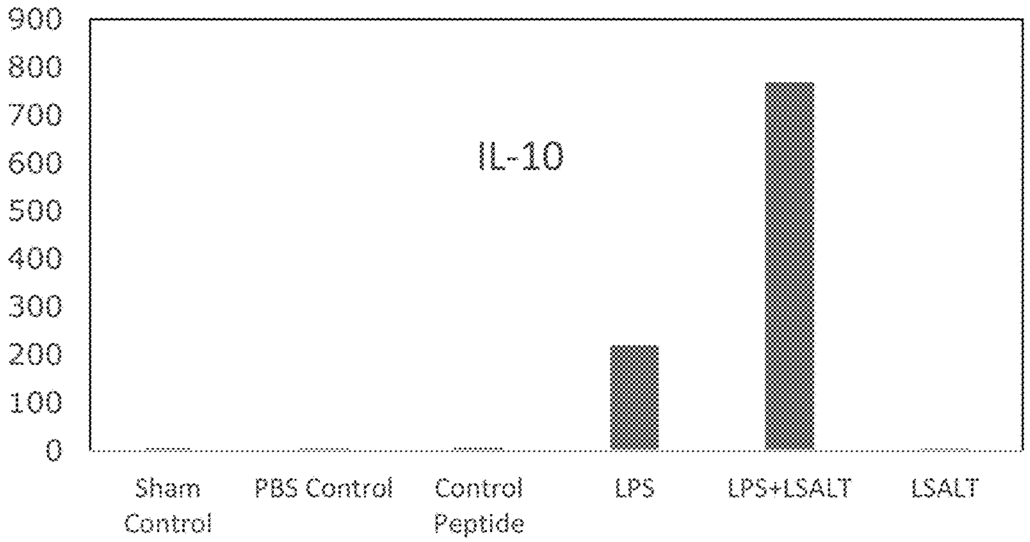
FIGS. 14H and I provides graphs showing the increase in IL-10 induced by LSALT peptide during LPS challenge.
Figure 14I:
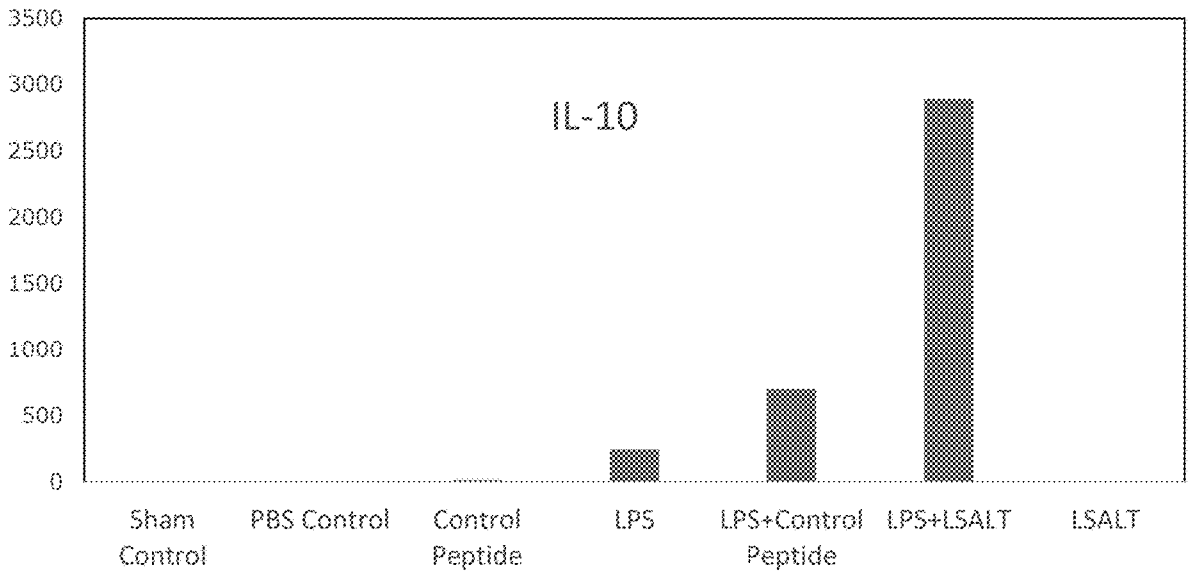

6-8 weeks old SCID mice were given an intraperitoneal injection of LPS (0.5 mg/kg) 5 minutes prior to intravenous injection of LSALT peptide or a control peptide. 4 hours following injection of LPS, blood was collected by cardiac puncture and changes in plasma cytokine levels were assessed using Luminex Cytokine Arrays. Bar graphs show the level of the anti-inflammatory cytokine IL-10 released in the plasma in LSALT peptide or control peptide in two independent experiments. (FIG. 14H and FIG. 14I) LSALT peptide increases the production of the anti-inflammatory mediator IL-10 in response to LPS.

Figure 15A:
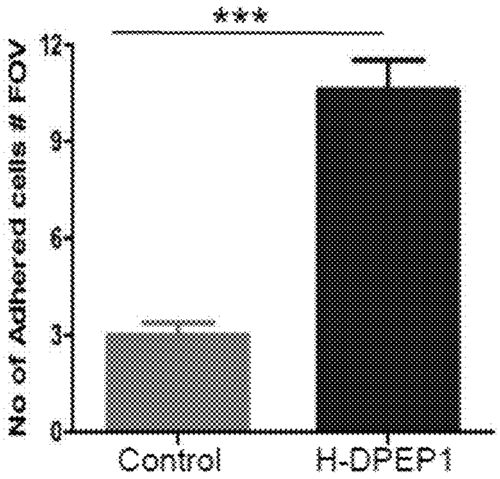
FIG. 15A provides a graph showing the number 70W melanoma cells bound/adhered transfected Cos-1 cells seeded on top of the DPEP-1 expressing Cos-1 monolayer. Proteins from DPEP-1 transfected cells were isolated and western blot analysis was performed to assess DPEP-1 expression. Photographs of western blots are shown in FIG. 15B.
Figure 15B:
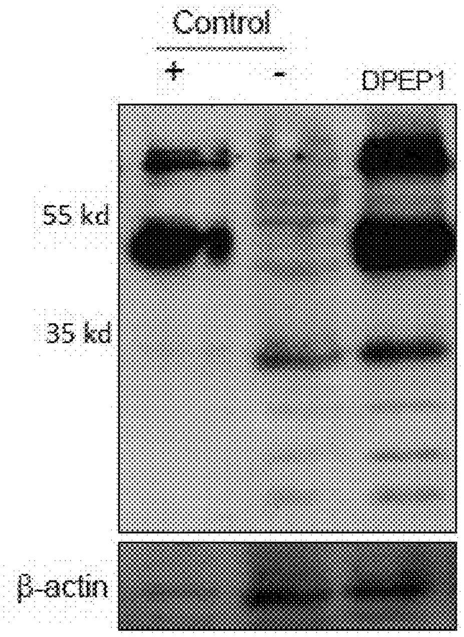
FIG. 15C shows the results of a membrane dipeptidase activity assay performed to compare the binding of 70 W melanoma cells to DPEP-1 transfected cells against the control of mock transfected cells.
Figure 15C:
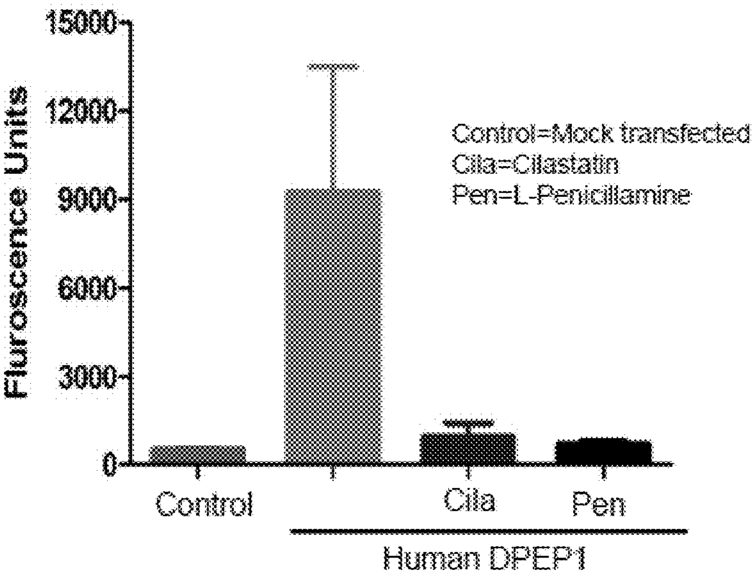

Example 15: 70W Human Melanoma Cells Bind to DPEP-1 Expressing Cos-1 Monolayer In Vitro Cos-1 cells were transfected with 3 pg of human DPEP-1 cDNA. Transfected cells were reseeded 24 hours after on 12 or 24 well places. 48 hours later, 70W melanoma cells expressing stable GFP-luciferase were harvested using Puck's EDTA and $10\times10^3$ cells were seeded on top of the DPEP-1 expressing Cos-1 monolayer. Cells were incubated for 4 hours at 37 C. After incubation cells were vigorously washed two times with PBS. Cells were then fixed using paraformaldehyde (4%). The number 70W melanoma cells bound/adhered were counted under 10× magnification over 10 different field of views using an inverted fluorescence microscope. These results are shown graphically in FIG. 15A. Proteins from DPEP-1 transfected cells were isolated after 48 hours using octyl-glucoside/RIPA lysis buffer and western blot analysis was performed to assess DPEP-1 expression using a DPEP-1 specific antibody (Proteintech). Photographs of western blots are shown in FIG. 15B. Membrane dipeptidase activity assay and the fluorometric detection of D-Phe was performed exactly as described by Heywood and Hooper (1995). A unpaired 2-tailed student's t-test was performed to compare the binding of 70W melanoma cells to DPEP-1 transfected cells against the control of mock transfected cells. These results are shown graphically in FIG. 15C. Values shown are from three independent experiments; asterisks (***) indicate P<0.001 as compared with mock transfected cells.

Figure 16:
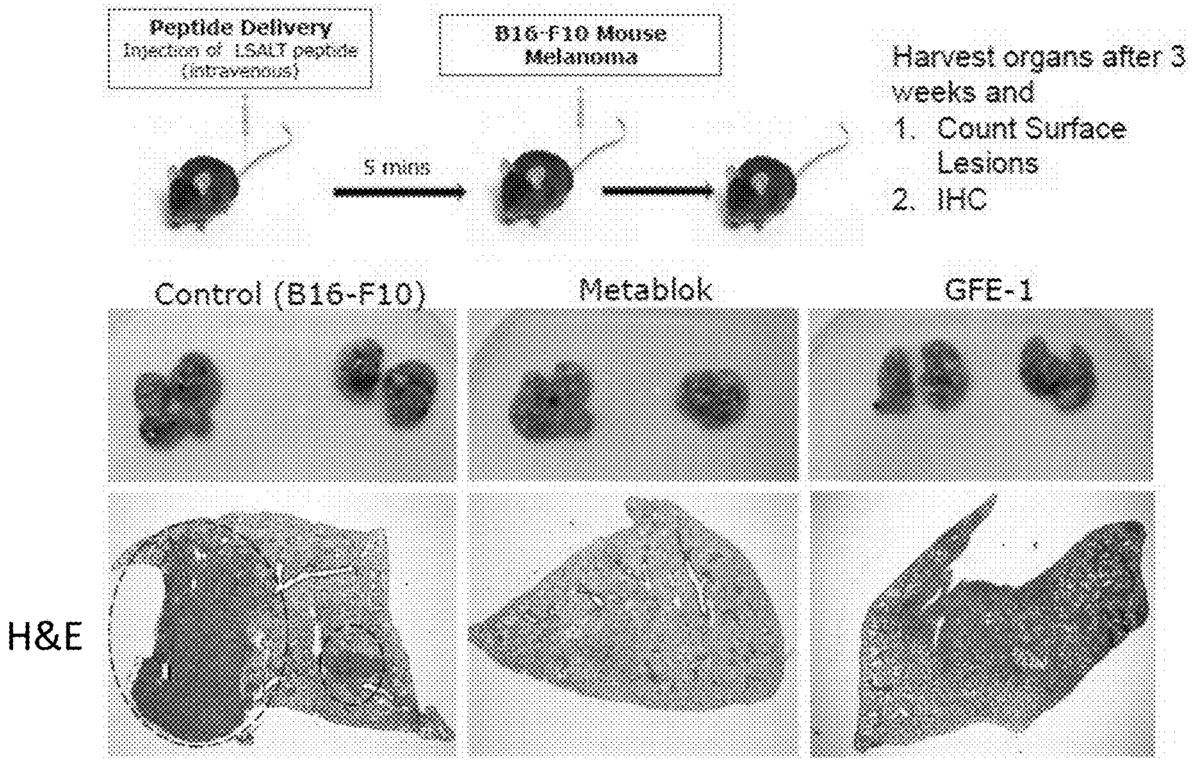
FIG. 16 provides representative photomicrographs of tissue explants of 8-10 weeks old C57-BL6 mice (Charles River) injected intravenously with 100,000 B16-F10 murine melanoma cells 5 minutes after the injection of either LSALT or GFE-1 peptide via intravenous tail injection.

Example 16: Lsalt Inhibits Melanoma-Lung Metastasis in a Syngeneic Animal Model In Vivo 8-10 weeks old C57-BL6 mice (Charles River) were injected intravenously with 100,000 B16-F10 murine melanoma cells 5 minutes after the injection of either LSALT or GFE-1 peptide (1 mM) via intravenous tail injection. Animals were sacrificed after 2 weeks and lungs were harvested. Tissues were processed for histology as described before and bematoxylin-eosin staining was performed to assess tumor burden. Photographs of tissue explants are shown in FIG. 16.

Example 17: Inhibition of Dipeptidase with an Aminophosphinic Acid Derivative During Renal Ischemia Reperfusion Injury Reduces Inflammation LysM (gfp/gfp) mice are subjected to 30 min. of unilateral renal ischemia at 37° C. via vascular clamp and 120 min. of reperfusion and the affected kidney is imaged using multiphoton microscopy. An aminophosphinic acid derivative is used to pretreat mice 10 min before ischemia. The aminophosphinic acid derivative has the formula.

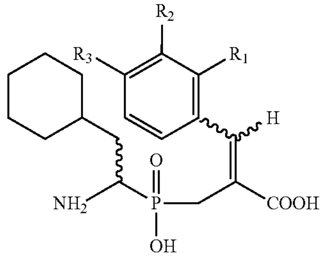

where R1 is H, R2 is H and R3 is F.

Labeling antibodies is injected intravenously before imaging Images of kidney before (NT) and after IRI (120 min.) with various inhibitors are obtained. Adherent neutrophils in interstitial spaces after IRI are observed. Neutrophils are quantified over a 120 min. time course.

Example 18: Inhibition of Dipeptidase (DPEP-1) with an Aminophosphinic Acid Derivative During Intravenous Contrast Reduces Inflammation LysM (gfp/gfp) mice are sensitized to acute renal injury by dehydration prior to intravenous injection of contrast (5 mL/kg). An aminophosphinic acid derivative is used intravenously to pretreat mice 10 min before contrast injection. Kidney is imaged 6 hours post-injection of contrast using multiphoton microscopy. Neutrophils are quantified 6 hours after contrast.

It will be appreciated how various changes and modifications may be made without departing from the invention.

The invention claimed is:

1. A method for treating inflammation or blocking leucocyte recruitment in a subject in need thereof, comprising administering an effective amount of a compound that binds to DPEP-1 to the subject, thereby treating inflammation or blocking leucocyte recruitment; wherein the compound that binds to DPEP-1 is selected from the group consisting of:

(a) cilastatin;

(b) a peptide that comprises a GFE tripeptide sequence selected from CGFECVRQCPERC (GFE-1) or CGFELETC (GFE-2);

(c) a compound that comprises a blocking antibody of DPEP-1; and (d) a compound that comprises an aminophosphinic acid derivative having the formula:

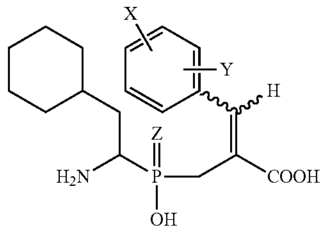

E & Z-isomers wherein X is selected from the group consisting of any halogen or $C_1$ to $C_6$ haloalkyl or $C_1$ to $C_6$ di- or trihaloalkyl or $C_1$ to $C_6$ alkyl, NH2, N($C_1$ to $C_6$ alkyl)$_2$, and NH($C_1$ to $C_6$ alkyl), $CF_3NR'$, or F, Cl, Br, $I^{125}$, I, $CF_3NR'$;

Y is selected from the group consisting of any halogen, H, $CH_3$, $OCH_3$, NH2, N($C_1$ to $C_6$ alkyl)$_2$, and NH($C_1$ to $C_6$ alkyl), NR' or $C_1$ to $C_6$ haloalkyl, or $C_1$ to $C_6$ alkoxy group or $C_1$ to $C_6$ di- or trihaloalkyl or $C_1$ to $C_6$ alkyl;

NR' is selected from $NH_2$, N($C_1$ to $C_6$ alkyl)$_2$, and NH($C_1$ to $C_6$ alkyl); and Z is selected from O or S.

2. The method of claim 1, wherein the compound is a peptide that comprises a GFE tripeptide sequence selected from CGFECVRQCPERC (GFE-1) or CGFELETC (GFE-2).

3. The method of claim 2, wherein the peptide is not conjugated to cilastatin.

4. The method of claim 1, wherein the compound comprises a blocking antibody of DPEP-1.

5. The method of claim 1, wherein the compound is cilastatin.

6. The method of claim 1, wherein the compound comprises an aminophosphinic acid derivative having the formula:

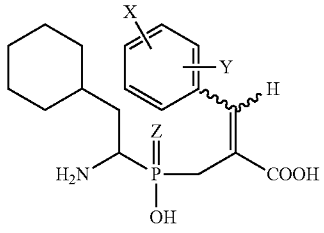

E & Z-isomers wherein X is selected from the group consisting of any halogen or $C_1$ to $C_6$ haloalkyl or $C_1$ to $C_6$ di- or trihaloalkyl or $C_1$ to $C_6$ alkyl, NH2, N($C_1$ to $C_6$ alkyl)$_2$, and NH($C_1$ to $C_6$ alkyl), $CF_3NR'$, or F, Cl, Br, $I^{125}$, I, $CF_3NR'$;

Y is selected from the group consisting of any halogen, H, $CH_3$, $OCH_3$, NH2, N($C_1$ to $C_6$ alkyl)$_2$, and NH($C_1$ to $C_6$ alkyl), NR' or $C_1$ to $C_6$ haloalkyl, or $C_1$ to $C_6$ alkoxy group or $C_1$ to $C_6$ di- or trihaloalkyl or $C_1$ to $C_6$ alkyl;

NR' is selected from $NH_2$, N($C_1$ to $C_6$ alkyl)$_2$, and NH($C_1$ to $C_6$ alkyl); and Z is selected from O or S.

7. The method of claim 1, wherein the compound is provided as a pharmaceutical composition.

8. The method of claim 7, wherein the pharmaceutical composition is suitable for parenteral or intravenous administration.

9. The method of claim 1, wherein the effective amount is between about 0.01 mg/kg and about 100 mg/kg.

10. The method of claim 1, wherein the inflammation is associated with acute kidney injury.

11. The method of claim 1, further comprising identifying the subject by performing a diagnostic test to determine a need for reduction in inflammation.

12. The method of claim 1, wherein the method treats or prevents leucocyte recruitment and inflammation during sepsis.

13. The method of claim 1, wherein the inflammation is characterized by a profile of inflammatory markers selected from IL-12, IP-10, IL-1b, IL-5, GM-CSF, IFN Gamma and IL-1a.

* * * * *

SEQUENCE LISTING

```
Sequence total quantity: 36
SEQ ID NO: 1            moltype = AA  length = 16
FEATURE                 Location/Qualifiers
source                  1..16
                        mol_type = protein
                        organism = Homo sapiens
SEQUENCE: 1
LSALTPSPSW LKYKAL                                                   16

SEQ ID NO: 2            moltype = AA  length = 13
FEATURE                 Location/Qualifiers
source                  1..13
                        mol_type = protein
                        organism = Homo sapiens
SEQUENCE: 2
CGFECVRQCP ERC                                                      13

SEQ ID NO: 3            moltype = AA  length = 8
FEATURE                 Location/Qualifiers
source                  1..8
                        mol_type = protein
                        organism = Homo sapiens
SEQUENCE: 3
CGFELETC                                                            8

SEQ ID NO: 4            moltype = AA  length = 17
FEATURE                 Location/Qualifiers
VARIANT                 1
                        note = MISC_FEATURE - X is any naturally-occurring amino
                         acid, unconventional amino acid or amino acid analog
source                  1..17
                        mol_type = protein
                        organism = Homo sapiens
SEQUENCE: 4
XLSALTPSPS WLKYKAL                                                  17

SEQ ID NO: 5            moltype = AA  length = 18
FEATURE                 Location/Qualifiers
VARIANT                 1..2
                        note = MISC_FEATURE - X is any naturally-occurring amino
                         acid, unconventional amino acid or amino acid analog
source                  1..18
                        mol_type = protein
                        organism = Homo sapiens
SEQUENCE: 5
XXLSALTPSP SWLKYKAL                                                 18

SEQ ID NO: 6            moltype = AA  length = 19
FEATURE                 Location/Qualifiers
VARIANT                 1..3
                        note = MISC_FEATURE - X is any naturally-occurring amino
                         acid, unconventional amino acid or amino acid analog
source                  1..19
                        mol_type = protein
                        organism = Homo sapiens
SEQUENCE: 6
XXXLSALTPS PSWLKYKAL                                                19

SEQ ID NO: 7            moltype = AA  length = 20
FEATURE                 Location/Qualifiers
VARIANT                 1..4
                        note = MISC_FEATURE - X is any naturally-occurring amino
                         acid, unconventional amino acid or amino acid analog
source                  1..20
                        mol_type = protein
                        organism = Homo sapiens
SEQUENCE: 7
XXXXLSALTP SPSWLKYKAL                                               20

SEQ ID NO: 8            moltype = AA  length = 17
FEATURE                 Location/Qualifiers
VARIANT                 17
                        note = misc_feature - Xaa can be any naturally occurring
                         amino acid
source                  1..17
                        mol_type = protein
                        organism = Homo sapiens
SEQUENCE: 8
```

-continued

```
LSALTPSPSW LKYKALX                                              17

SEQ ID NO: 9           moltype = AA  length = 18
FEATURE                Location/Qualifiers
VARIANT                17..18
                       note = misc_feature - Xaa can be any naturally occurring
                        amino acid
source                 1..18
                       mol_type = protein
                       organism = Homo sapiens
SEQUENCE: 9
LSALTPSPSW LKYKALXX                                             18

SEQ ID NO: 10          moltype = AA  length = 19
FEATURE                Location/Qualifiers
VARIANT                17..19
                       note = misc_feature - Xaa can be any naturally occurring
                        amino acid
source                 1..19
                       mol_type = protein
                       organism = Homo sapiens
SEQUENCE: 10
LSALTPSPSW LKYKALXXX                                            19

SEQ ID NO: 11          moltype = AA  length = 20
FEATURE                Location/Qualifiers
VARIANT                17..20
                       note = misc_feature - Xaa can be any naturally occurring
                        amino acid
source                 1..20
                       mol_type = protein
                       organism = Homo sapiens
SEQUENCE: 11
LSALTPSPSW LKYKALXXXX                                           20

SEQ ID NO: 12          moltype = AA  length = 18
FEATURE                Location/Qualifiers
VARIANT                1
                       note = MISC_FEATURE - X is any naturally-occurring amino
                        acid, unconventional amino acid or amino acid analog
VARIANT                18
                       note = MISC_FEATURE - X is any naturally-occurring amino
                        acid, unconventional amino acid or amino acid analog
source                 1..18
                       mol_type = protein
                       organism = Homo sapiens
SEQUENCE: 12
XLSALTPSPS WLKYKALX                                             18

SEQ ID NO: 13          moltype = AA  length = 19
FEATURE                Location/Qualifiers
VARIANT                1
                       note = MISC_FEATURE - X is any naturally-occurring amino
                        acid, unconventional amino acid or amino acid analog
VARIANT                18..19
                       note = MISC_FEATURE - X is any naturally-occurring amino
                        acid, unconventional amino acid or amino acid analog
source                 1..19
                       mol_type = protein
                       organism = Homo sapiens
SEQUENCE: 13
XLSALTPSPS WLKYKALXX                                            19

SEQ ID NO: 14          moltype = AA  length = 20
FEATURE                Location/Qualifiers
VARIANT                1
                       note = MISC_FEATURE - X is any naturally-occurring amino
                        acid, unconventional amino acid or amino acid analog
VARIANT                18..20
                       note = MISC_FEATURE - X is any naturally-occurring amino
                        acid, unconventional amino acid or amino acid analog
source                 1..20
                       mol_type = protein
                       organism = Homo sapiens
SEQUENCE: 14
XLSALTPSPS WLKYKALXXX                                           20

SEQ ID NO: 15          moltype = AA  length = 21
FEATURE                Location/Qualifiers
```

-continued

```
VARIANT                 1
                        note = MISC_FEATURE - X is any naturally-occurring amino
                         acid, unconventional amino acid or amino acid analog
VARIANT                 18..21
                        note = MISC_FEATURE - X is any naturally-occurring amino
                         acid, unconventional amino acid or amino acid analog
source                  1..21
                        mol_type = protein
                        organism = Homo sapiens
SEQUENCE: 15
XLSALTPSPS WLKYKALXXX X                                                    21

SEQ ID NO: 16           moltype = AA  length = 22
FEATURE                 Location/Qualifiers
VARIANT                 1
                        note = MISC_FEATURE - X is any naturally-occurring amino
                         acid, unconventional amino acid or amino acid analog
VARIANT                 18..22
                        note = MISC_FEATURE - X is any naturally-occurring amino
                         acid, unconventional amino acid or amino acid analog
source                  1..22
                        mol_type = protein
                        organism = Homo sapiens
SEQUENCE: 16
XLSALTPSPS WLKYKALXXX XX                                                   22

SEQ ID NO: 17           moltype = AA  length = 19
FEATURE                 Location/Qualifiers
VARIANT                 1..2
                        note = MISC_FEATURE - X is any naturally-occurring amino
                         acid, unconventional amino acid or amino acid analog
VARIANT                 19
                        note = MISC_FEATURE - X is any naturally-occurring amino
                         acid, unconventional amino acid or amino acid analog
source                  1..19
                        mol_type = protein
                        organism = Homo sapiens
SEQUENCE: 17
XXLSALTPSP SWLKYKALX                                                       19

SEQ ID NO: 18           moltype = AA  length = 19
FEATURE                 Location/Qualifiers
VARIANT                 1..2
                        note = MISC_FEATURE - X is any naturally-occurring amino
                         acid, unconventional amino acid or amino acid analog
VARIANT                 18..19
                        note = MISC_FEATURE - X is any naturally-occurring amino
                         acid, unconventional amino acid or amino acid analog
source                  1..19
                        mol_type = protein
                        organism = Homo sapiens
SEQUENCE: 18
XXLSALTPSP SWLKYKAXX                                                       19

SEQ ID NO: 19           moltype = AA  length = 21
FEATURE                 Location/Qualifiers
VARIANT                 1..2
                        note = MISC_FEATURE - X is any naturally-occurring amino
                         acid, unconventional amino acid or amino acid analog
VARIANT                 19..20
                        note = MISC_FEATURE - X is any naturally-occurring amino
                         acid, unconventional amino acid or amino acid analog
VARIANT                 21
                        note = misc_feature - Xaa can be any naturally occurring
                         amino acid
source                  1..21
                        mol_type = protein
                        organism = Homo sapiens
SEQUENCE: 19
XXLSALTPSP SWLKYKALXX X                                                    21

SEQ ID NO: 20           moltype = AA  length = 22
FEATURE                 Location/Qualifiers
VARIANT                 1..2
                        note = MISC_FEATURE - X is any naturally-occurring amino
                         acid, unconventional amino acid or amino acid analog
VARIANT                 19..22
                        note = MISC_FEATURE - X is any naturally-occurring amino
                         acid, unconventional amino acid or amino acid analog
```

-continued

```
source                  1..22
                        mol_type = protein
                        organism = Homo sapiens
SEQUENCE: 20
XXLSALTPSP SWLKYKALXX XX                                            22

SEQ ID NO: 21           moltype = AA  length = 23
FEATURE                 Location/Qualifiers
VARIANT                 1..2
                        note = MISC_FEATURE - X is any naturally-occurring amino
                         acid, unconventional amino acid or amino acid analog
VARIANT                 19..23
                        note = MISC_FEATURE - X is any naturally-occurring amino
                         acid, unconventional amino acid or amino acid analog
source                  1..23
                        mol_type = protein
                        organism = Homo sapiens
SEQUENCE: 21
XXLSALTPSP SWLKYKALXX XXX                                           23

SEQ ID NO: 22           moltype = AA  length = 20
FEATURE                 Location/Qualifiers
VARIANT                 1..3
                        note = MISC_FEATURE - X is any naturally-occurring amino
                         acid, unconventional amino acid or amino acid analog
VARIANT                 20
                        note = MISC_FEATURE - X is any naturally-occurring amino
                         acid, unconventional amino acid or amino acid analog
source                  1..20
                        mol_type = protein
                        organism = Homo sapiens
SEQUENCE: 22
XXXLSALTPS PSWLKYKALX                                               20

SEQ ID NO: 23           moltype = AA  length = 21
FEATURE                 Location/Qualifiers
VARIANT                 1..3
                        note = MISC_FEATURE - X is any naturally-occurring amino
                         acid, unconventional amino acid or amino acid analog
VARIANT                 20..21
                        note = MISC_FEATURE - X is any naturally-occurring amino
                         acid, unconventional amino acid or amino acid analog
source                  1..21
                        mol_type = protein
                        organism = Homo sapiens
SEQUENCE: 23
XXXLSALTPS PSWLKYKALX X                                             21

SEQ ID NO: 24           moltype = AA  length = 22
FEATURE                 Location/Qualifiers
VARIANT                 1..3
                        note = MISC_FEATURE - X is any naturally-occurring amino
                         acid, unconventional amino acid or amino acid analog
VARIANT                 20..22
                        note = MISC_FEATURE - X is any naturally-occurring amino
                         acid, unconventional amino acid or amino acid analog
source                  1..22
                        mol_type = protein
                        organism = Homo sapiens
SEQUENCE: 24
XXXLSALTPS PSWLKYKALX XX                                            22

SEQ ID NO: 25           moltype = AA  length = 23
FEATURE                 Location/Qualifiers
VARIANT                 1..3
                        note = MISC_FEATURE - X is any naturally-occurring amino
                         acid, unconventional amino acid or amino acid analog
VARIANT                 20..23
                        note = MISC_FEATURE - X is any naturally-occurring amino
                         acid, unconventional amino acid or amino acid analog
source                  1..23
                        mol_type = protein
                        organism = Homo sapiens
SEQUENCE: 25
XXXLSALTPS PSWLKYKALX XXX                                           23

SEQ ID NO: 26           moltype = AA  length = 24
FEATURE                 Location/Qualifiers
VARIANT                 1..3
```

```
                      note = MISC_FEATURE - X is any naturally-occurring amino
                       acid, unconventional amino acid or amino acid analog
VARIANT               20..24
                      note = MISC_FEATURE - X is any naturally-occurring amino
                       acid, unconventional amino acid or amino acid analog
source                1..24
                      mol_type = protein
                      organism = Homo sapiens
SEQUENCE: 26
XXXLSALTPS PSWLKYKALX XXXX                                        24

SEQ ID NO: 27         moltype = AA  length = 21
FEATURE               Location/Qualifiers
VARIANT               1..4
                      note = MISC_FEATURE - X is any naturally-occurring amino
                       acid, unconventional amino acid or amino acid analog
VARIANT               21
                      note = MISC_FEATURE - X is any naturally-occurring amino
                       acid, unconventional amino acid or amino acid analog
source                1..21
                      mol_type = protein
                      organism = Homo sapiens
SEQUENCE: 27
XXXXLSALTP SPSWLKYKAL X                                           21

SEQ ID NO: 28         moltype = AA  length = 22
FEATURE               Location/Qualifiers
VARIANT               1..4
                      note = MISC_FEATURE - X is any naturally-occurring amino
                       acid, unconventional amino acid or amino acid analog
VARIANT               21..22
                      note = MISC_FEATURE - X is any naturally-occurring amino
                       acid, unconventional amino acid or amino acid analog
source                1..22
                      mol_type = protein
                      organism = Homo sapiens
SEQUENCE: 28
XXXXLSALTP SPSWLKYKAL XX                                          22

SEQ ID NO: 29         moltype = AA  length = 23
FEATURE               Location/Qualifiers
VARIANT               1..4
                      note = MISC_FEATURE - X is any naturally-occurring amino
                       acid, unconventional amino acid or amino acid analog
VARIANT               21..23
                      note = MISC_FEATURE - X is any naturally-occurring amino
                       acid, unconventional amino acid or amino acid analog
source                1..23
                      mol_type = protein
                      organism = Homo sapiens
SEQUENCE: 29
XXXXLSALTP SPSWLKYKAL XXX                                         23

SEQ ID NO: 30         moltype = AA  length = 24
FEATURE               Location/Qualifiers
VARIANT               1..4
                      note = MISC_FEATURE - X is any naturally-occurring amino
                       acid, unconventional amino acid or amino acid analog
VARIANT               21..24
                      note = MISC_FEATURE - X is any naturally-occurring amino
                       acid, unconventional amino acid or amino acid analog
source                1..24
                      mol_type = protein
                      organism = Homo sapiens
SEQUENCE: 30
XXXXLSALTP SPSWLKYKAL XXXX                                        24

SEQ ID NO: 31         moltype = AA  length = 25
FEATURE               Location/Qualifiers
VARIANT               1..4
                      note = MISC_FEATURE - X is any naturally-occurring amino
                       acid, unconventional amino acid or amino acid analog
VARIANT               21..25
                      note = MISC_FEATURE - X is any naturally-occurring amino
                       acid, unconventional amino acid or amino acid analog
source                1..25
                      mol_type = protein
                      organism = Homo sapiens
SEQUENCE: 31
```

-continued

```
XXXXLSALTP SPSWLKYKAL XXXXX                                        25

SEQ ID NO: 32          moltype = AA  length = 22
FEATURE                Location/Qualifiers
VARIANT                1..5
                       note = MISC_FEATURE - X is any naturally-occurring amino
                        acid, unconventional amino acid or amino acid analog
VARIANT                22
                       note = MISC_FEATURE - X is any naturally-occurring amino
                        acid, unconventional amino acid or amino acid analog
source                 1..22
                       mol_type = protein
                       organism = Homo sapiens
SEQUENCE: 32
XXXXXLSALT PSPSWLKYKA LX                                           22

SEQ ID NO: 33          moltype = AA  length = 23
FEATURE                Location/Qualifiers
VARIANT                1..5
                       note = MISC_FEATURE - X is any naturally-occurring amino
                        acid, unconventional amino acid or amino acid analog
VARIANT                22..23
                       note = MISC_FEATURE - X is any naturally-occurring amino
                        acid, unconventional amino acid or amino acid analog
source                 1..23
                       mol_type = protein
                       organism = Homo sapiens
SEQUENCE: 33
XXXXXLSALT PSPSWLKYKA LXX                                          23

SEQ ID NO: 34          moltype = AA  length = 24
FEATURE                Location/Qualifiers
VARIANT                1..5
                       note = MISC_FEATURE - X is any naturally-occurring amino
                        acid, unconventional amino acid or amino acid analog
VARIANT                22..24
                       note = MISC_FEATURE - X is any naturally-occurring amino
                        acid, unconventional amino acid or amino acid analog
source                 1..24
                       mol_type = protein
                       organism = Homo sapiens
SEQUENCE: 34
XXXXXLSALT PSPSWLKYKA LXXX                                         24

SEQ ID NO: 35          moltype = AA  length = 25
FEATURE                Location/Qualifiers
VARIANT                1..5
                       note = MISC_FEATURE - X is any naturally-occurring amino
                        acid, unconventional amino acid or amino acid analog
VARIANT                22..25
                       note = MISC_FEATURE - X is any naturally-occurring amino
                        acid, unconventional amino acid or amino acid analog
source                 1..25
                       mol_type = protein
                       organism = Homo sapiens
SEQUENCE: 35
XXXXXLSALT PSPSWLKYKA LXXXX                                        25

SEQ ID NO: 36          moltype = AA  length = 26
FEATURE                Location/Qualifiers
VARIANT                1..5
                       note = MISC_FEATURE - X is any naturally-occurring amino
                        acid, unconventional amino acid or amino acid analog
VARIANT                22..26
                       note = MISC_FEATURE - X is any naturally-occurring amino
                        acid, unconventional amino acid or amino acid analog
source                 1..26
                       mol_type = protein
                       organism = Homo sapiens
SEQUENCE: 36
XXXXXLSALT PSPSWLKYKA LXXXXX                                       26
```